(12) United States Patent
Scheinberg

(10) Patent No.: US 11,033,613 B2
(45) Date of Patent: Jun. 15, 2021

(54) METHODS AND COMPOSITIONS FOR TREATING CANCER

(71) Applicant: Memorial Sloan Kettering Cancer Center, New York, NY (US)

(72) Inventor: David Scheinberg, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 115 days.

(21) Appl. No.: 15/777,514

(22) PCT Filed: Nov. 18, 2016

(86) PCT No.: PCT/US2016/062865
§ 371 (c)(1),
(2) Date: May 18, 2018

(87) PCT Pub. No.: WO2017/087857
PCT Pub. Date: May 26, 2017

(65) Prior Publication Data
US 2018/0339030 A1  Nov. 29, 2018

Related U.S. Application Data

(60) Provisional application No. 62/258,134, filed on Nov. 20, 2015.

(51) Int. Cl.
| | | |
|---|---|---|
| *A61K 39/00* | (2006.01) | |
| *C07K 14/47* | (2006.01) | |
| *C07K 14/82* | (2006.01) | |
| *A61K 39/395* | (2006.01) | |
| *A61P 35/00* | (2006.01) | |

(52) U.S. Cl.
CPC .......... *A61K 39/00* (2013.01); *A61K 39/0011* (2013.01); *A61K 39/001153* (2018.08); *A61K 39/3955* (2013.01); *C07K 14/47* (2013.01); *C07K 14/4748* (2013.01); *C07K 14/82* (2013.01); *A61K 2039/505* (2013.01); *A61K 2039/5154* (2013.01); *A61K 2039/5158* (2013.01); *A61K 2039/54* (2013.01); *A61K 2039/55505* (2013.01); *A61K 2039/55522* (2013.01); *A61K 2039/892* (2018.08); *A61P 35/00* (2018.01)

(58) Field of Classification Search
None
See application file for complete search history.

(56) References Cited

U.S. PATENT DOCUMENTS

| | | | |
|---|---|---|---|
| 4,722,848 A | 2/1988 | Paoletti et al. | |
| 5,440,013 A | 8/1995 | Kahn | |
| 5,837,249 A | 11/1998 | Heber-Katz et al. | |
| 7,030,212 B1 | 4/2006 | Sugiyama et al. | |
| 7,063,854 B1 | 6/2006 | Gaiger et al. | |
| 7,115,272 B1 | 10/2006 | Gaiger et al. | |
| 7,144,581 B2 | 12/2006 | Gaiger et al. | |
| 7,323,181 B2 | 1/2008 | Gaiger et al. | |
| 7,329,410 B1 | 2/2008 | Gaiger et al. | |
| 7,368,119 B2 | 5/2008 | Gaiger et al. | |
| 7,380,871 B2 | 6/2008 | Froeschle et al. | |
| 7,517,950 B2 | 4/2009 | Sugiyama et al. | |
| 7,553,494 B2 | 6/2009 | Gaiger et al. | |
| 7,598,221 B2 * | 10/2009 | Scheinberg | A61P 35/02 514/1.1 |
| 7,608,685 B1 | 10/2009 | Sugiyama et al. | |
| 7,655,249 B2 | 2/2010 | Gaiger et al. | |
| 7,662,386 B2 | 2/2010 | Gaiger et al. | |
| 7,666,985 B2 | 2/2010 | Sugiyama et al. | |
| 7,807,792 B2 | 10/2010 | Sugiyama et al. | |
| 7,901,693 B2 | 3/2011 | Gaiger et al. | |
| 7,915,393 B2 | 3/2011 | Gaiger et al. | |
| 2003/0082194 A1 | 5/2003 | Bazan et al. | |
| 2006/0084609 A1 | 4/2006 | Scheinberg et al. | |
| 2007/0128207 A1 | 6/2007 | Sugiyama | |
| 2008/0070835 A1 | 3/2008 | Sugiyama | |

(Continued)

FOREIGN PATENT DOCUMENTS

| | | |
|---|---|---|
| EP | 3299028 A1 | 3/2018 |
| WO | WO 1995/04064 | 2/1995 |

(Continued)

OTHER PUBLICATIONS

Brahmer et al. (Cancer Immunol. Res., 1: 85-91, 2013).*
Hamanishi et al. (Journal of Clinical Oncology, 32, (No. 15_suppl): 5511, May 20, 2014).*
Krug et al. (Cancer Immunol Immunother, 59(10): 1467-1479, 2010).*
PCT/US2016/062865 International Search report dated Mar. 27, 2017.

(Continued)

*Primary Examiner* — Nelson B Moseley, II

(74) *Attorney, Agent, or Firm* — Mark S. Cohen; Pearl Cohen; Zedek Latzer Baratz LLP

(57) ABSTRACT

This invention provides methods of treating, reducing the incidence of, and inducing immune responses to a WT1-expressing cancer, by administering a combination of at least one WT1 peptide, or cytotoxic T cells (CTLs) against a WT1-expressing cancer, and at least one checkpoint inhibitor. The at least one WT1 peptide can be administered to the subject by administering one or more agents to the subject resulting in delivery of one or more WT1 peptides and induction of an immune response against the WT1-expressing cancer. Examples of these WT1 delivery agents include: (i) an isolated WT1 peptide, (ii) a nucleic acid encoding the at least one WT1 peptide, and (iii) an immune cell comprising or presenting the at least one WT1 peptide or nucleic acid encoding the at least one WT1 peptide.

12 Claims, No Drawings

Specification includes a Sequence Listing.

(56) References Cited

U.S. PATENT DOCUMENTS

| | | | |
|---|---|---|---|
| 2009/0143291 A1 | 6/2009 | Sugiyama et al. | |
| 2010/0092522 A1 | 4/2010 | Scheinberg et al. | |
| 2010/0111986 A1* | 5/2010 | Scheinberg | A61K 39/0011 424/185.1 |
| 2010/0166738 A1 | 7/2010 | Gaiger et al. | |
| 2011/0070251 A1 | 3/2011 | Sugiyama | |
| 2011/0136141 A1 | 6/2011 | Adamczyk et al. | |
| 2015/0258186 A1 | 9/2015 | Florkiewicz | |
| 2018/0140691 A1 | 5/2018 | Takasu et al. | |

FOREIGN PATENT DOCUMENTS

| | | |
|---|---|---|
| WO | WO 1996/23060 | 8/1996 |
| WO | WO 2001/025273 A2 | 4/2001 |
| WO | WO 2003/037060 | 5/2003 |
| WO | WO 2005/053618 | 6/2005 |
| WO | WO 2007/047763 | 4/2007 |
| WO | WO 2007/047764 | 4/2007 |
| WO | WO 2007/120673 | 10/2007 |
| WO | WO 2013/106834 | 7/2013 |
| WO | WO 2014/113490 | 7/2014 |
| WO | WO 2014/144885 | 9/2014 |
| WO | WO 2015/061752 | 4/2015 |
| WO | WO 2015/069770 | 5/2015 |
| WO | WO 2015/103602 | 7/2015 |
| WO | WO2016186177 | 11/2016 |

OTHER PUBLICATIONS

Allavena et al., Intraperitoneal recombinant gamma-interferon in patients with recurrent ascitic ovarian carcinoma: modulation of cytotoxicity and cytokine production in tumor-associated effectors and of major histocompatibility antigen expression on tumor cells. Cancer Res, 1990. 50(22): p. 7318-23.
Altschul et al. "Gapped BLAST and PSI-BLAST: a new generation of protein database search programs." Nucleic acids research 25.17 (1997): 3389-3402.
Berek, J.S., et al., Randomized, placebo-controlled study of oregovomab for consolidation of clinical remission in patients with advanced ovarian cancer. J Clin Oncol, 2004. 22(17): p. 3507-16.
Boczkowski, David, et al. "Dendritic cells pulsed with RNA are potent antigen-presenting cells in vitro and in vivo." Journal of Experimental Medicine 184.2 (1996): 465-472.
Brahmer, J.R., et al., Safety and activity of anti-PD-L1 antibody in patients with advanced cancer. N Engl J Med, 2012. 366(26): p. 2455-65.
Chaise et al., "DNA vaccination induces WT1-specific T-cell responses with potential clinical relevance," Blood, 2008, 112(7):2956-2964.
Diefenbach et al., Safety and immunogenicity study of NY-ESO-1b peptide and montanide ISA-51 vaccination of patients with epithelial ovarian cancer in high-risk first remission. Clin Cancer Res, 2008. 14(9): p. 2740-8.
Duraiswamy et al., Dual blockade of PD-1 and CTLA-4 combined with tumor vaccine effectively restores T-cell rejection function in tumors. Cancer Res, 2013. 73(12): p. 3591-603.
Fikes JD, Sette A,. Design of multi-epitope, analogue-based cancer vaccines, Expert Opin Biol Ther. Sep. 2003;3(6):985-93.
Fioretti et al., DNA Vaccines: Developing New Strategies Against Cancer, Journal of Biomedicine and Biotechnology, 2010, 2010(938):174378.
Freeman et al., Engagement of the PD-1 immunoinhibitory receptor by a novel B7 family member leads to negative regulation of lymphocyte activation. J Exp Med, 2000. 192(7): p. 1027-34.
Gazit et al. "Chemo-adoptive immunotherapy of nude mice implanted with human colorectal carcinoma and melanoma cell lines." Cancer Immunology, Immunotherapy 35.2 (1992): 135-144.
Hamanishi et al., Programmed cell death 1 ligand 1 and tumor-infiltrating CD8+ T lymphocytes are prognostic factors of human ovarian cancer. Proc Natl Acad Sci U S A, 2007. 104(9): p. 3360-5.

Harrison M.L., et al., Duration of second or greater complete clinical remission in ovarian cancer: exploring potential endpoints for clinical trials. Gynecol Oncol, 2007. 106(3): p. 469-75.
Hodi F.S., et al., Immunologic and clinical effects of antibody blockade of cytotoxic T lymphocyte-associated antigen 4 in previously vaccinated cancer patients. Proc Natl Acad Sci U S A, 2008. 105(8): p. 3005-10.
Hwang, W.T., et al., Prognostic significance of tumor-infiltrating T cells in ovarian cancer: a meta-analysis. Gynecol Oncol, 2012. 124(2): p. 192-8.
Iasonos, A., et al., Identifying clinical improvement in consolidation single-arm phase 2 trials in patients with ovarian cancer in second or greater clinical remission. Int J Gynecol Cancer, 2012. 22(1): p. 63-9.
International Search Report from PCT/US2016/062865 dated Mar. 27, 2017.
International Preliminary Report on Patentability from PCT/US2018/062385 dated May 31, 2018.
Keiholz, U., et al., A clinical and immunologic phase 2 trial of Wilms tumor gene product 1 (WT1) peptide vaccination in patients with AML and MDS. Blood, 2009. 113(26): p. 6541-8.
Keir, M.E., et al., PD-1 and its ligands in tolerance and immunity. Annu Rev Immunol, 2008. 26: p. 677-704.
Krug, L.M., et al., WT1 peptide vaccinations induce CD4 and CD8 T cell immune responses in patients with mesothelioma and non-small cell lung cancer. Cancer Immunol Immunotherapy, 2010. 59(10): p. 1467-79.
Letsch, A., et al., Effect of vaccination of leukemia patients with a MHC class I peptide of Wilms tumor gene 1 (WT1) peptide with unspecific T helper stimulation on WT1-specific IgM responses and on IgG responses. J Clin Oncol, 2008. 26: p. Abstr 3054.
Maslak et al. "Vaccination with synthetic analog peptides derived from WT1 oncoprotein induces T-cell responses in patients with complete remission from acute myeloid leukemia." *Blood* 116.2 (2010): 171-179.
Matsuzaki, J., et al., Tumor-infiltrating NY-ESO-1-specific CD8+ T cells are negatively regulated by LAG-3 and PD-1 in human ovarian cancer. Proc Natl Acad Sci U S A, 2010. 107(17): p. 7875-80.
May, R.J., et al., Peptide epitopes from the Wilms' tumor 1 oncoprotein stimulate CD4+ and CD8+ T cells that recognize and kill human malignant mesothelioma tumor cells. Clin Cancer Res, 2007. 13(15 Pt 1): p. 4547-55.
Mu, C.Y., et al., High expression of PD-L1 in lung cancer may contribute to poor prognosis and tumor cells immune escape through suppressing tumor infiltrating dendritic cells maturation. Med Oncol, 2011. 28(3): p. 682-8.
Ohno S., et al., Wilms' tumor 1 (WT1) peptide immunotherapy for gynecological malignancy. Anticancer Res, 2009. 29(11): p. 4779-84.
Oji et al. "Expression of the Wilms' tumor gene WT1 in solid tumors and its involvement in tumor cell growth." *Japanese journal of cancer research* 90.2 (1999): 194-204.
Oka et al. "Induction of WT1 (Wilms' tumor gene)-specific cytotoxic T lymphocytes by WT1 peptide vaccine and the resultant cancer regression." *Proceedings of the National Academy of Sciences* 101.38 (2004): 13885-13890.
Page et al. "Immune modulation in cancer with antibodies." *Annual review of medicine* 65 (2014): 185-202.
Paglia et al. "Murine dendritic cells loaded in vitro with soluble protein prime cytotoxic T lymphocytes against tumor antigen in vivo." *Journal of Experimental Medicine* 183.1 (1996): 317-322.
Pardoll Drew M. "The blockade, of immune checkpoints in cancer immunotherapy." *Nature Reviews Cancer* 12.4 (2012): 252.
Quezada et al. "CTLA4 blockade and GM-CSF combination immunotherapy alters the intratumor balance of effector and regulatory T cells." *The Journal of clinical investigation* 116.7 (2006): 1935-1945.
Riether et al. "Blocking programmed cell death 1 in combination with adoptive cytotoxic T-cell transfer eradicates chronic myelogenous leukemia stem cells." *Leukemia* 29.8 (2015): 1781.
Schaed et al. "T-cell responses against tyrosinase 368-376 (370D) peptide in HLA∗A0201+ melanoma patients: randomized trial comparing incomplete Freund's adjuvant, granulocyte macrophage

(56) References Cited

OTHER PUBLICATIONS colony-stimulating factor, and QS-21 as immunological adjuvants." *Clinical Cancer Research* 8.5 (2002): 967-972.
Scharnhorst et al "Internal translation initiation generates novel WT1 protein isoforms with distinct biological properties." *Journal of B*iological Chemistry 274.33 (1999): 23456-23462. Siegel, R., and D. Naishadham. "Jemal A (2012) Cancer statistics." *CA Cancer. Clin* 62 (2012): 10-29.
Stather et al, "130: High PD-1 Levels at baseline are associated with unfavourable clinical outcome in a Wilms Tumour Gene 1 (Wt1) Peptide Vaccination setting in Leukaemia patients" Abstract; Society for Immunotherapy of Cancer, 26th Annual Meeting, Jan. 2011, North Bethesda MD.
Supplementary European Search Report from EP16867262 dated May 28, 2019.
Wahren B. et al., "DNA Vaccines: Recent Developments and the Future," Vaccines, 2014, 2:785-796.
Wolchok et. al., Development of ipilimumab: a novel immunotherapeutic approach for the treatment of advanced melanoma. Annals of the New York Academy of Sciences, 2013. 1291(1): p. 1-13.
Office Action dated May 12, 2020 for corresponding EP application No. EP16867262.4.
Berger Raanan et al: "Phase I safety and pharmacokinetic study of CT-011, a humanized antibody interacting with PD-1, in patients with advanced hematologic malignancies.", Clinical Cancer Research: An Official Journal of the American Association for Cancer Research May 15, 2008, vol. 14, No. 10, May 15, 2008 (May 15, 2008), pp. 3044-3051.
Keilholz Ulrich et al: "A clinical and immunologic phase 2 trial of Wilms tumor gene product 1 (WT1) peptide vaccination in patients with AML and MDS", Blood, vol. 113, No. 26, Jun. 25, 2009 (Jun. 25, 2009), pp. 6541-6548.
Schnorfeil Frauke M et al: "T cells are functionally not impaired in AML: increased PD-1 expression is only seen at time of relapse and correlates with a shift towards the memory T cell compartment.", Journal of Hematology & Oncology Jul. 30, 2015, vol. 8, Jul. 30, 2015 (Jul. 30, 2015), p. 93.
Hamanishi et al., 2014, Efficacy and Safety of Anti-PD-1 Antibody (Nivolumab: BMS-936558, ONO-4538) in Patients with Platinum-Resistant Ovarian Cancer, Journal of Clinical Oncology, 32, (No. 15_suppl): 5511, May 20, 2014.
Hodi et al, 2010, Improved Survival with Ipilimumab in Patients with Metastatic Melanoma, N Engl J Med 2010;363:711-23).
Sanderson et al., Autoimmunity in a Phase I Trial of a Fully Human Anti-Cytotoxic T-lymphocyte antigen-4 Monoclonal Antibody With Multiple Melanoma Peptides and Montanide ISA 51 for Patients With Resected Stages III and IV Melanoma, 2005, J Clin Oncol 23:741-750.
Sarnaik et al., 2011, Extended Dose Ipilimumab with a Peptide Vaccine: Immune Correlates Associated with Clinical Benefit in Patients with Resected High-Risk Stage IIIc/IV Melanoma, Clin Cancer Res 17:896-906.
Weber et al., 2013, Safety, Efficacy, and Biomarkers of Nivolumab With Vaccine in Ipilimumab-Refractory or -Naive Melanoma, J. Clin. Oncol. 31 (34), 4311-4318.
Madan RA, et al., 2012. Ipilimumab and a poxviral vaccine targeting prostate-specific antigen in metastatic castration-resistant prostate cancer: a phase 1 dose-escalation trial. Lancet Oncol. 13(5):501-508.
Lawson et al., 2015, Randomized, Placebo-Controlled, Phase III Trial of Yeast-Derived Granulocyte-Macrophage Colony-Stimulating Factor (GM-CSF) Versus Peptide Vaccination Versus GM-CSF Plus Peptide Vaccination Versus Placebo in Patients With No Evidence of Disease After Complete Surgical Resection of Locally Advanced and/or Stage IV Melanoma: A Trial of the Eastern Cooperative Oncology Group—American College of Radiology Imaging Network Cancer Research Group (E4697), J Clin Oncol 33:4066-4076). O'Caerbhaill et al., 2018, A phase I study of concomitant galinpepimut-S (GPS) in combination with nivolumab (nivo) in patients (pts) with WT1+ ovarian cancer (OC) in second or third remission, J. Olin. Oncol. 36, No. 15_suppl:5553.
Harrison et al., 2007, Duration of Second or Greater Complete Clinical Remission in Ovarian Cancer: Exploring Potential Endpoints for Clinical Trials, Gynecol Oncol 106:469-475.
Parmar et al., 2003, Paclitaxel plus platinum-based chemotherapy versus conventional platinum-based chemotherapy in women with relapsed ovarian cancer: the ICON4/AGO-OVAR—2.2 trial. Lancet 361:2099-2106.
Pujade-Laurraine et al., 2014, Bevacizurnab Combined With Chemotherapy for Platinum-Resistant Recurrent Ovarian Cancer: The AURELIA Open-Label Randomized Phase III Trial, J Clin Oncol 32:1302-1308.
Aghajanian et al., 2012, OCEANS: A Randomized, Double-Blind, Placebo-Controlled Phase III Trial of Chemotherapy With or Without Bevacizumab in Patients With Platinum-Sensitive Recurrent Epithelial Ovarian, Primary Peritoneal, or Fallopian Tube Cancer, J Clin Oncol 30:2039-2045.
SELLAS Life Sciences Group, R&D Day 2019 Presentation, Nov. 15, 2019, https://s22.q4cdn.com/485546146/files/doc_presentations/2019/11/15/SELLAS-KOL-Symposium-Presentation-11.15.pdf.
Office Action dated Oct. 27, 2020 for corresponding JP application No. 2018-526090.
Lim, K.P. et al., J Immunother, 2011, vol. 34, No. 9, pp. 704.
Brahmer JR, et al. J Clin Oncol 2010, 28:3167-3175."Phase I Study of Single-Agent Anti—Programmed Death-1 (MDX-1106) in Refractory Solid Tumors: Safety, Clinical Activity, Pharmacodynamics, and Immunologic Correlates".
Kong et al. Frontier in Immunology 2014 vol. 5 Article 2 "Opportunistic autoimmune disorders potentiated by immune-checkpoint inhibitors anti-CTLA-4 and anti-PD-1".
Simeone E, et al. Expert Rev Respir Med. Jan. 2020;14(1):5-13. "Nivolumab for the treatment of small cell lungcancer".
Tsujikawa T et al. Clin Cancer Res. Jul. 15, 2020;26(14):3578-3588."Evaluation of Cyclophosphamide/GVAX Pancreas Followed by Listeria-mesothelin (CRS-207) With or Without Nivolumab in Patients with Pancreatic Cancer".
Varga et al., 2019 Gynecology Oncology 152 243-250 "Pembrolizumab in patients with programmed death ligand 1—positive advanced ovarian cancer: Analysis of KEYNOTE-028".
SELLAS Announces Promising Initial Clinical Data for Galinpepimut-S (GPS) in Combination with Checkpoint Inhibitors in Two Solid Tumor Indications Nasdaq_SLS.
O'Caerbhaill et al., 2018, "A phase I study of concomitant galinpepimut-S (GPS) in combination with nivolumab (nivo) in patients (pts) with WT1+ ovarian cancer (OC) in second or third remission" J. Clin. Oncol. 36, No. 15_suppl:5553.
Zamarin et al. "Randomized Phase II Trial of Nivolumab Versus Nivolumab and Ipilimumab for Recurrent or Persistent Ovarian Cancer: An NRG Oncology Study" Journal of Clinical Oncology (2020), vol. 38, issue 16, pp. 1814-1824, downloaded Mar. 22, 2021.

\* cited by examiner

SEQUENCE LISTING

<160> NUMBER OF SEQ ID NOS: 204

<210> SEQ ID NO 1
<211> LENGTH: 19
<212> TYPE: PRT
<213> ORGANISM: Homo sapiens

<400> SEQUENCE: 1

Arg Ser Asp Glu Leu Val Arg His His Asn Met His Gln Arg Asn Met
1               5                   10                  15

Thr Lys Leu

<210> SEQ ID NO 2
<211> LENGTH: 22
<212> TYPE: PRT
<213> ORGANISM: Homo sapiens

<400> SEQUENCE: 2

Pro Gly Cys Asn Lys Arg Tyr Phe Lys Leu Ser His Leu Gln Met His
1               5                   10                  15

Ser Arg Lys His Thr Gly
            20

<210> SEQ ID NO 3
<211> LENGTH: 15
<212> TYPE: PRT
<213> ORGANISM: Homo sapiens

<400> SEQUENCE: 3

Leu Val Arg His His Asn Met His Gln Arg Asn Met Thr Lys Leu
1               5                   10                  15

<210> SEQ ID NO 4
<211> LENGTH: 15
<212> TYPE: PRT
<213> ORGANISM: Homo sapiens

<400> SEQUENCE: 4

Asn Lys Arg Tyr Phe Lys Leu Ser His Leu Gln Met His Ser Arg
1               5                   10                  15

<210> SEQ ID NO 5
<211> LENGTH: 19
<212> TYPE: PRT
<213> ORGANISM: Homo sapiens

<400> SEQUENCE: 5

Ser Gly Gln Ala Arg Met Phe Pro Asn Ala Pro Tyr Leu Pro Ser Cys
1               5                   10                  15

Leu Glu Ser

<210> SEQ ID NO 6
<211> LENGTH: 15
<212> TYPE: PRT
<213> ORGANISM: Homo sapiens

<400> SEQUENCE: 6

Gln Ala Arg Met Phe Pro Asn Ala Pro Tyr Leu Pro Ser Cys Leu
1               5                   10                  15

<210> SEQ ID NO 7
<211> LENGTH: 9
<212> TYPE: PRT

<213> ORGANISM: Homo sapiens

<400> SEQUENCE: 7

Arg Met Phe Pro Asn Ala Pro Tyr Leu
1               5

<210> SEQ ID NO 8
<211> LENGTH: 9
<212> TYPE: PRT
<213> ORGANISM: Homo sapiens

<400> SEQUENCE: 8

Ser Leu Gly Glu Gln Gln Tyr Ser Val
1               5

<210> SEQ ID NO 9
<211> LENGTH: 9
<212> TYPE: PRT
<213> ORGANISM: Homo sapiens

<400> SEQUENCE: 9

Ala Leu Leu Pro Ala Val Pro Ser Leu
1               5

<210> SEQ ID NO 10
<211> LENGTH: 9
<212> TYPE: PRT
<213> ORGANISM: Homo sapiens

<400> SEQUENCE: 10

Asn Leu Gly Ala Thr Leu Lys Gly Val
1               5

<210> SEQ ID NO 11
<211> LENGTH: 9
<212> TYPE: PRT
<213> ORGANISM: Homo sapiens

<400> SEQUENCE: 11

Asp Leu Asn Ala Leu Leu Pro Ala Val
1               5

<210> SEQ ID NO 12
<211> LENGTH: 9
<212> TYPE: PRT
<213> ORGANISM: Homo sapiens

<400> SEQUENCE: 12

Gly Val Phe Arg Gly Ile Gln Asp Val
1               5

<210> SEQ ID NO 13
<211> LENGTH: 9
<212> TYPE: PRT
<213> ORGANISM: Homo sapiens

<400> SEQUENCE: 13

Lys Arg Tyr Phe Lys Leu Ser His Leu
1               5

<210> SEQ ID NO 14
<211> LENGTH: 9
<212> TYPE: PRT
<213> ORGANISM: Homo sapiens

```
<400> SEQUENCE: 14

Ala Leu Leu Leu Arg Thr Pro Tyr Ser
1               5

<210> SEQ ID NO 15
<211> LENGTH: 9
<212> TYPE: PRT
<213> ORGANISM: Homo sapiens

<400> SEQUENCE: 15

Cys Met Thr Trp Met Gln Met Asn Leu
1               5

<210> SEQ ID NO 16
<211> LENGTH: 9
<212> TYPE: PRT
<213> ORGANISM: Homo sapiens

<400> SEQUENCE: 16

Asn Met His Gln Arg Asn Met Thr Lys
1               5

<210> SEQ ID NO 17
<211> LENGTH: 9
<212> TYPE: PRT
<213> ORGANISM: Homo sapiens

<400> SEQUENCE: 17

Gln Met Asn Leu Gly Ala Thr Leu Lys
1               5

<210> SEQ ID NO 18
<211> LENGTH: 10
<212> TYPE: PRT
<213> ORGANISM: Homo sapiens

<400> SEQUENCE: 18

Phe Met Cys Ala Tyr Pro Gly Cys Asn Lys
1               5                   10

<210> SEQ ID NO 19
<211> LENGTH: 10
<212> TYPE: PRT
<213> ORGANISM: Homo sapiens

<400> SEQUENCE: 19

Lys Leu Ser His Leu Gln Met His Ser Arg
1               5                   10

<210> SEQ ID NO 20
<211> LENGTH: 9
<212> TYPE: PRT
<213> ORGANISM: Homo sapiens

<400> SEQUENCE: 20

Asn Gln Met Asn Leu Gly Ala Thr Leu
1               5

<210> SEQ ID NO 21
<211> LENGTH: 9
<212> TYPE: PRT
<213> ORGANISM: Mutated Homo sapiens

<400> SEQUENCE: 21
```

```
Asn Leu Met Asn Leu Gly Ala Thr Leu
1               5
```

<210> SEQ ID NO 22
<211> LENGTH: 9
<212> TYPE: PRT
<213> ORGANISM: Mutated Homo sapiens

<400> SEQUENCE: 22

```
Asn Tyr Met Asn Leu Gly Ala Thr Leu
1               5
```

<210> SEQ ID NO 23
<211> LENGTH: 15
<212> TYPE: PRT
<213> ORGANISM: Homo sapiens

<400> SEQUENCE: 23

```
Cys Met Thr Trp Asn Gln Met Asn Leu Gly Ala Thr Leu Lys Gly
1               5                   10                  15
```

<210> SEQ ID NO 24
<211> LENGTH: 15
<212> TYPE: PRT
<213> ORGANISM: Mutated Homo sapiens

<400> SEQUENCE: 24

```
Cys Met Thr Trp Asn Leu Met Asn Leu Gly Ala Thr Leu Lys Gly
1               5                   10                  15
```

<210> SEQ ID NO 25
<211> LENGTH: 15
<212> TYPE: PRT
<213> ORGANISM: Homo sapiens

<400> SEQUENCE: 25

```
Trp Asn Gln Met Asn Leu Gly Ala Thr Leu Lys Gly Val Ala Ala
1               5                   10                  15
```

<210> SEQ ID NO 26
<211> LENGTH: 15
<212> TYPE: PRT
<213> ORGANISM: Mutated Homo sapiens

<400> SEQUENCE: 26

```
Trp Asn Leu Met Asn Leu Gly Ala Thr Leu Lys Gly Val Ala Ala
1               5                   10                  15
```

<210> SEQ ID NO 27
<211> LENGTH: 15
<212> TYPE: PRT
<213> ORGANISM: Homo sapiens

<400> SEQUENCE: 27

```
Met Thr Trp Asn Gln Met Asn Leu Gly Ala Thr Leu Lys Gly Val
1               5                   10                  15
```

<210> SEQ ID NO 28
<211> LENGTH: 15
<212> TYPE: PRT
<213> ORGANISM: Homo sapiens

<400> SEQUENCE: 28

```
Thr Trp Asn Gln Met Asn Leu Gly Ala Thr Leu Lys Gly Val Ala
1               5                   10                  15
```

```
<210> SEQ ID NO 29
<211> LENGTH: 15
<212> TYPE: PRT
<213> ORGANISM: Homo sapiens

<400> SEQUENCE: 29

Cys Met Thr Trp Asn Leu Met Asn Leu Gly Ala Thr Leu Lys Gly
1               5                   10                  15

<210> SEQ ID NO 30
<211> LENGTH: 15
<212> TYPE: PRT
<213> ORGANISM: Mutated Homo sapiens

<400> SEQUENCE: 30

Met Thr Trp Asn Leu Met Asn Leu Gly Ala Thr Leu Lys Gly Val
1               5                   10                  15

<210> SEQ ID NO 31
<211> LENGTH: 15
<212> TYPE: PRT
<213> ORGANISM: Mutated Homo sapiens

<400> SEQUENCE: 31

Thr Trp Asn Leu Met Asn Leu Gly Ala Thr Leu Lys Gly Val Ala
1               5                   10                  15

<210> SEQ ID NO 32
<211> LENGTH: 15
<212> TYPE: PRT
<213> ORGANISM: Mutated Homo sapiens

<400> SEQUENCE: 32

Trp Asn Leu Met Asn Leu Gly Ala Thr Leu Lys Gly Val Ala Ala
1               5                   10                  15

<210> SEQ ID NO 33
<211> LENGTH: 15
<212> TYPE: PRT
<213> ORGANISM: Homo sapiens

<400> SEQUENCE: 33

Met Thr Trp Asn Tyr Met Asn Leu Gly Ala Thr Leu Lys Gly Val
1               5                   10                  15

<210> SEQ ID NO 34
<211> LENGTH: 15
<212> TYPE: PRT
<213> ORGANISM: Mutated Homo sapiens

<400> SEQUENCE: 34

Thr Trp Asn Tyr Met Asn Leu Gly Ala Thr Leu Lys Gly Val Ala
1               5                   10                  15

<210> SEQ ID NO 35
<211> LENGTH: 17
<212> TYPE: PRT
<213> ORGANISM: Homo sapiens

<400> SEQUENCE: 35

Cys Met Thr Trp Asn Gln Met Asn Leu Gly Ala Thr Leu Lys Gly Val
1               5                   10                  15

Ala
```

<210> SEQ ID NO 36
<211> LENGTH: 9
<212> TYPE: PRT
<213> ORGANISM: Homo sapiens

<400> SEQUENCE: 36

Trp Asn Gln Met Asn Leu Gly Ala Thr
1               5

<210> SEQ ID NO 37
<211> LENGTH: 9
<212> TYPE: PRT
<213> ORGANISM: Homo sapiens

<400> SEQUENCE: 37

Thr Trp Asn Gln Met Asn Leu Gly Ala
1               5

<210> SEQ ID NO 38
<211> LENGTH: 9
<212> TYPE: PRT
<213> ORGANISM: Homo sapiens

<400> SEQUENCE: 38

Met Thr Trp Asn Gln Met Asn Leu Gly
1               5

<210> SEQ ID NO 39
<211> LENGTH: 17
<212> TYPE: PRT
<213> ORGANISM: Mutated Homo sapiens

<400> SEQUENCE: 39

Cys Met Thr Trp Asn Leu Met Asn Leu Gly Ala Thr Leu Lys Gly Val
1               5                   10                  15

Ala

<210> SEQ ID NO 40
<211> LENGTH: 9
<212> TYPE: PRT
<213> ORGANISM: Mutated Homo sapiens

<400> SEQUENCE: 40

Trp Asn Leu Met Asn Leu Gly Ala Thr
1               5

<210> SEQ ID NO 41
<211> LENGTH: 9
<212> TYPE: PRT
<213> ORGANISM: Mutated Homo sapiens

<400> SEQUENCE: 41

Met Asn Leu Gly Ala Thr Leu Lys Gly
1               5

<210> SEQ ID NO 42
<211> LENGTH: 9
<212> TYPE: PRT
<213> ORGANISM: Homo sapiens

<400> SEQUENCE: 42

Met Thr Trp Asn Gln Met Asn Leu Gly
1               5

<210> SEQ ID NO 43
<211> LENGTH: 17
<212> TYPE: PRT
<213> ORGANISM: Mutated Homo sapiens

<400> SEQUENCE: 43

Cys Met Thr Trp Asn Tyr Met Asn Leu Gly Ala Thr Leu Lys Gly Val
1               5                   10                  15

Ala

<210> SEQ ID NO 44
<211> LENGTH: 9
<212> TYPE: PRT
<213> ORGANISM: Homo sapiens

<400> SEQUENCE: 44

Met Asn Leu Gly Ala Thr Leu Lys Gly
1               5

<210> SEQ ID NO 45
<211> LENGTH: 9
<212> TYPE: PRT
<213> ORGANISM: Homo sapiens

<400> SEQUENCE: 45

Met Thr Trp Asn Gln Met Asn Leu Gly
1               5

<210> SEQ ID NO 46
<211> LENGTH: 9
<212> TYPE: PRT
<213> ORGANISM: Homo sapiens

<400> SEQUENCE: 46

Gly Ala Leu Arg Asn Pro Thr Ala Cys
1               5

<210> SEQ ID NO 47
<211> LENGTH: 9
<212> TYPE: PRT
<213> ORGANISM: Homo sapiens

<400> SEQUENCE: 47

Gly Tyr Leu Arg Asn Pro Thr Ala Cys
1               5

<210> SEQ ID NO 48
<211> LENGTH: 9
<212> TYPE: PRT
<213> ORGANISM: Homo sapiens

<400> SEQUENCE: 48

Gly Ala Leu Arg Asn Pro Thr Ala Leu
1               5

<210> SEQ ID NO 49
<211> LENGTH: 9
<212> TYPE: PRT
<213> ORGANISM: Homo sapiens

<400> SEQUENCE: 49

Gly Leu Leu Arg Asn Pro Thr Ala Cys
1               5

```
<210> SEQ ID NO 50
<211> LENGTH: 9
<212> TYPE: PRT
<213> ORGANISM: Homo sapiens

<400> SEQUENCE: 50

Arg Gln Arg Pro His Pro Gly Ala Leu
1               5

<210> SEQ ID NO 51
<211> LENGTH: 9
<212> TYPE: PRT
<213> ORGANISM: Homo sapiens

<400> SEQUENCE: 51

Arg Tyr Arg Pro His Pro Gly Ala Leu
1               5

<210> SEQ ID NO 52
<211> LENGTH: 9
<212> TYPE: PRT
<213> ORGANISM: Homo sapiens

<400> SEQUENCE: 52

Tyr Gln Arg Pro His Pro Gly Ala Leu
1               5

<210> SEQ ID NO 53
<211> LENGTH: 9
<212> TYPE: PRT
<213> ORGANISM: Homo sapiens

<400> SEQUENCE: 53

Arg Leu Arg Pro His Pro Gly Ala Leu
1               5

<210> SEQ ID NO 54
<211> LENGTH: 9
<212> TYPE: PRT
<213> ORGANISM: Homo sapiens

<400> SEQUENCE: 54

Arg Ile Arg Pro His Pro Gly Ala Leu
1               5

<210> SEQ ID NO 55
<211> LENGTH: 9
<212> TYPE: PRT
<213> ORGANISM: Homo sapiens

<400> SEQUENCE: 55

Gly Ala Leu Arg Asn Pro Thr Ala Cys
1               5

<210> SEQ ID NO 56
<211> LENGTH: 9
<212> TYPE: PRT
<213> ORGANISM: Homo sapiens

<400> SEQUENCE: 56

Gly Ala Leu Arg Asn Pro Thr Ala Leu
1               5
```

<210> SEQ ID NO 57
<211> LENGTH: 9
<212> TYPE: PRT
<213> ORGANISM: Homo sapiens

<400> SEQUENCE: 57

Arg Gln Arg Pro His Pro Gly Ala Leu
1               5

<210> SEQ ID NO 58
<211> LENGTH: 9
<212> TYPE: PRT
<213> ORGANISM: Homo sapiens

<400> SEQUENCE: 58

Arg Leu Arg Pro His Pro Gly Ala Leu
1               5

<210> SEQ ID NO 59
<211> LENGTH: 9
<212> TYPE: PRT
<213> ORGANISM: Homo sapiens

<400> SEQUENCE: 59

Arg Ile Arg Pro His Pro Gly Ala Leu
1               5

<210> SEQ ID NO 60
<211> LENGTH: 15
<212> TYPE: PRT
<213> ORGANISM: Homo sapiens

<400> SEQUENCE: 60

Gln Phe Pro Asn His Ser Phe Lys His Glu Asp Pro Met Gly Gln
1               5                   10                  15

<210> SEQ ID NO 61
<211> LENGTH: 15
<212> TYPE: PRT
<213> ORGANISM: Homo sapiens

<400> SEQUENCE: 61

Gln Phe Pro Asn His Ser Phe Lys His Glu Asp Pro Met Gly Gln
1               5                   10                  15

<210> SEQ ID NO 62
<211> LENGTH: 9
<212> TYPE: PRT
<213> ORGANISM: Homo sapiens

<400> SEQUENCE: 62

His Ser Phe Lys His Glu Asp Pro Met
1               5

<210> SEQ ID NO 63
<211> LENGTH: 9
<212> TYPE: PRT
<213> ORGANISM: Homo sapiens

<400> SEQUENCE: 63

His Ser Phe Lys His Glu Asp Pro Tyr
1               5

<210> SEQ ID NO 64
<211> LENGTH: 9

```
<212> TYPE: PRT
<213> ORGANISM: Homo sapiens

<400> SEQUENCE: 64

His Ser Phe Lys His Glu Asp Pro Lys
1               5

<210> SEQ ID NO 65
<211> LENGTH: 15
<212> TYPE: PRT
<213> ORGANISM: Homo sapiens

<400> SEQUENCE: 65

Lys Arg Pro Phe Met Cys Ala Tyr Pro Gly Cys Tyr Lys Arg Tyr
1               5                   10                  15

<210> SEQ ID NO 66
<211> LENGTH: 15
<212> TYPE: PRT
<213> ORGANISM: Homo sapiens

<400> SEQUENCE: 66

Ser Glu Lys Arg Pro Phe Met Cys Ala Tyr Pro Gly Cys Asn Lys
1               5                   10                  15

<210> SEQ ID NO 67
<211> LENGTH: 13
<212> TYPE: PRT
<213> ORGANISM: Homo sapiens

<400> SEQUENCE: 67

Lys Arg Pro Phe Met Cys Ala Tyr Pro Gly Cys Asn Lys
1               5                   10

<210> SEQ ID NO 68
<211> LENGTH: 9
<212> TYPE: PRT
<213> ORGANISM: Homo sapiens

<400> SEQUENCE: 68

Phe Met Cys Ala Tyr Pro Gly Cys Asn
1               5

<210> SEQ ID NO 69
<211> LENGTH: 9
<212> TYPE: PRT
<213> ORGANISM: Homo sapiens

<400> SEQUENCE: 69

Phe Met Cys Ala Tyr Pro Gly Cys Tyr
1               5

<210> SEQ ID NO 70
<211> LENGTH: 9
<212> TYPE: PRT
<213> ORGANISM: Homo sapiens

<400> SEQUENCE: 70

Phe Met Cys Ala Tyr Pro Gly Cys Lys
1               5

<210> SEQ ID NO 71
<211> LENGTH: 9
<212> TYPE: PRT
<213> ORGANISM: Homo sapiens
```

<400> SEQUENCE: 71

Arg Gln Arg Pro His Pro Gly Ala Leu
1               5

<210> SEQ ID NO 72
<211> LENGTH: 9
<212> TYPE: PRT
<213> ORGANISM: Homo sapiens

<400> SEQUENCE: 72

Gly Ala Leu Arg Asn Pro Thr Ala Cys
1               5

<210> SEQ ID NO 73
<211> LENGTH: 9
<212> TYPE: PRT
<213> ORGANISM: Homo sapiens

<400> SEQUENCE: 73

Pro Leu Pro His Phe Pro Pro Ser Leu
1               5

<210> SEQ ID NO 74
<211> LENGTH: 9
<212> TYPE: PRT
<213> ORGANISM: Homo sapiens

<400> SEQUENCE: 74

His Phe Pro Pro Ser Leu Pro Pro Thr
1               5

<210> SEQ ID NO 75
<211> LENGTH: 9
<212> TYPE: PRT
<213> ORGANISM: Homo sapiens

<400> SEQUENCE: 75

Thr His Ser Pro Thr His Pro Pro Arg
1               5

<210> SEQ ID NO 76
<211> LENGTH: 9
<212> TYPE: PRT
<213> ORGANISM: Homo sapiens

<400> SEQUENCE: 76

Ala Ile Leu Asp Phe Leu Leu Leu Gln
1               5

<210> SEQ ID NO 77
<211> LENGTH: 9
<212> TYPE: PRT
<213> ORGANISM: Homo sapiens

<400> SEQUENCE: 77

Pro Gly Cys Leu Gln Gln Pro Glu Gln
1               5

<210> SEQ ID NO 78
<211> LENGTH: 11
<212> TYPE: PRT
<213> ORGANISM: Homo sapiens

<400> SEQUENCE: 78

Pro Gly Cys Leu Gln Gln Pro Glu Gln Gly
1               5                   10

<210> SEQ ID NO 79
<211> LENGTH: 9
<212> TYPE: PRT
<213> ORGANISM: Homo sapiens

<400> SEQUENCE: 79

Lys Leu Gly Ala Ala Glu Ala Ser Ala
1               5

<210> SEQ ID NO 80
<211> LENGTH: 9
<212> TYPE: PRT
<213> ORGANISM: Homo sapiens

<400> SEQUENCE: 80

Ala Ser Gly Ser Glu Pro Gln Gln Met
1               5

<210> SEQ ID NO 81
<211> LENGTH: 10
<212> TYPE: PRT
<213> ORGANISM: Homo sapiens

<400> SEQUENCE: 81

Arg Asp Leu Asn Ala Leu Leu Pro Ala Val
1               5                   10

<210> SEQ ID NO 82
<211> LENGTH: 10
<212> TYPE: PRT
<213> ORGANISM: Homo sapiens

<400> SEQUENCE: 82

Gly Gly Cys Ala Leu Pro Val Ser Gly Ala
1               5                   10

<210> SEQ ID NO 83
<211> LENGTH: 9
<212> TYPE: PRT
<213> ORGANISM: Homo sapiens

<400> SEQUENCE: 83

Gly Ala Ala Gln Trp Ala Pro Val Leu
1               5

<210> SEQ ID NO 84
<211> LENGTH: 9
<212> TYPE: PRT
<213> ORGANISM: Homo sapiens

<400> SEQUENCE: 84

Leu Asp Phe Ala Pro Pro Gly Ala Ser
1               5

<210> SEQ ID NO 85
<211> LENGTH: 11
<212> TYPE: PRT
<213> ORGANISM: Homo sapiens

<400> SEQUENCE: 85

Leu Asp Phe Ala Pro Pro Gly Ala Ser Ala Tyr

<210> SEQ ID NO 86
<211> LENGTH: 9
<212> TYPE: PRT
<213> ORGANISM: Homo sapiens

<400> SEQUENCE: 86

Ser Ala Tyr Gly Ser Leu Gly Gly Pro
1               5

<210> SEQ ID NO 87
<211> LENGTH: 9
<212> TYPE: PRT
<213> ORGANISM: Homo sapiens

<400> SEQUENCE: 87

Pro Ala Pro Pro Pro Pro Pro Pro Pro
1               5

<210> SEQ ID NO 88
<211> LENGTH: 9
<212> TYPE: PRT
<213> ORGANISM: Homo sapiens

<400> SEQUENCE: 88

Ala Cys Arg Tyr Gly Pro Phe Gly Pro
1               5

<210> SEQ ID NO 89
<211> LENGTH: 9
<212> TYPE: PRT
<213> ORGANISM: Homo sapiens

<400> SEQUENCE: 89

Ser Gly Gln Ala Arg Met Phe Pro Asn
1               5

<210> SEQ ID NO 90
<211> LENGTH: 9
<212> TYPE: PRT
<213> ORGANISM: Homo sapiens

<400> SEQUENCE: 90

Arg Met Phe Pro Asn Ala Pro Tyr Leu
1               5

<210> SEQ ID NO 91
<211> LENGTH: 9
<212> TYPE: PRT
<213> ORGANISM: Homo sapiens

<400> SEQUENCE: 91

Pro Ser Cys Leu Glu Ser Gln Pro Ala
1               5

<210> SEQ ID NO 92
<211> LENGTH: 9
<212> TYPE: PRT
<213> ORGANISM: Homo sapiens

<400> SEQUENCE: 92

Asn Gln Gly Tyr Ser Thr Val Thr Phe
1               5

<210> SEQ ID NO 93
<211> LENGTH: 9
<212> TYPE: PRT
<213> ORGANISM: Homo sapiens

<400> SEQUENCE: 93

His His Ala Ala Gln Phe Pro Asn His
1               5

<210> SEQ ID NO 94
<211> LENGTH: 9
<212> TYPE: PRT
<213> ORGANISM: Homo sapiens

<400> SEQUENCE: 94

His Ser Phe Lys His Glu Asp Pro Met
1               5

<210> SEQ ID NO 95
<211> LENGTH: 9
<212> TYPE: PRT
<213> ORGANISM: Homo sapiens

<400> SEQUENCE: 95

Cys His Thr Pro Thr Asp Ser Cys Thr
1               5

<210> SEQ ID NO 96
<211> LENGTH: 9
<212> TYPE: PRT
<213> ORGANISM: Homo sapiens

<400> SEQUENCE: 96

Cys Thr Gly Ser Gln Ala Leu Leu Leu
1               5

<210> SEQ ID NO 97
<211> LENGTH: 9
<212> TYPE: PRT
<213> ORGANISM: Homo sapiens

<400> SEQUENCE: 97

Thr Asp Ser Cys Thr Gly Ser Gln Ala
1               5

<210> SEQ ID NO 98
<211> LENGTH: 9
<212> TYPE: PRT
<213> ORGANISM: Homo sapiens

<400> SEQUENCE: 98

Arg Thr Pro Tyr Ser Ser Asp Asn Leu
1               5

<210> SEQ ID NO 99
<211> LENGTH: 10
<212> TYPE: PRT
<213> ORGANISM: Homo sapiens

<400> SEQUENCE: 99

Asn Leu Tyr Gln Met Thr Ser Gln Leu Glu
1               5                   10

<210> SEQ ID NO 100

<211> LENGTH: 9
<212> TYPE: PRT
<213> ORGANISM: Homo sapiens

<400> SEQUENCE: 100

Trp Asn Gln Met Asn Leu Gly Ala Thr
1               5

<210> SEQ ID NO 101
<211> LENGTH: 9
<212> TYPE: PRT
<213> ORGANISM: Mutated Homo sapiens

<400> SEQUENCE: 101

Asn Gln Met Asn Leu Gly Ala Thr Leu
1               5

<210> SEQ ID NO 102
<211> LENGTH: 11
<212> TYPE: PRT
<213> ORGANISM: Homo sapiens

<400> SEQUENCE: 102

Trp Asn Gln Met Asn Leu Gly Ala Thr Leu Lys
1               5                   10

<210> SEQ ID NO 103
<211> LENGTH: 15
<212> TYPE: PRT
<213> ORGANISM: Homo sapiens

<400> SEQUENCE: 103

Cys Met Thr Trp Asn Gln Met Asn Leu Gly Ala Thr Leu Lys Gly
1               5                   10                  15

<210> SEQ ID NO 104
<211> LENGTH: 9
<212> TYPE: PRT
<213> ORGANISM: Homo sapiens

<400> SEQUENCE: 104

Asn Leu Gly Ala Thr Leu Lys Gly Val
1               5

<210> SEQ ID NO 105
<211> LENGTH: 10
<212> TYPE: PRT
<213> ORGANISM: Homo sapiens

<400> SEQUENCE: 105

Leu Gly Ala Thr Leu Lys Gly Val Ala Ala
1               5                   10

<210> SEQ ID NO 106
<211> LENGTH: 8
<212> TYPE: PRT
<213> ORGANISM: Homo sapiens

<400> SEQUENCE: 106

Thr Leu Gly Val Ala Ala Gly Ser
1               5

<210> SEQ ID NO 107
<211> LENGTH: 9
<212> TYPE: PRT

<213> ORGANISM: Homo sapiens

<400> SEQUENCE: 107

Gly Tyr Glu Ser Asp Asn His Thr Thr
1               5

<210> SEQ ID NO 108
<211> LENGTH: 10
<212> TYPE: PRT
<213> ORGANISM: Homo sapiens

<400> SEQUENCE: 108

Phe Met Cys Ala Tyr Pro Gly Cys Asn Lys
1               5                   10

<210> SEQ ID NO 109
<211> LENGTH: 11
<212> TYPE: PRT
<213> ORGANISM: Homo sapiens

<400> SEQUENCE: 109

Lys Arg Pro Phe Met Cys Ala Tyr Pro Gly Cys
1               5                   10

<210> SEQ ID NO 110
<211> LENGTH: 9
<212> TYPE: PRT
<213> ORGANISM: Homo sapiens

<400> SEQUENCE: 110

Arg Lys Phe Ser Arg Ser Asp His Leu
1               5

<210> SEQ ID NO 111
<211> LENGTH: 10
<212> TYPE: PRT
<213> ORGANISM: Homo sapiens

<400> SEQUENCE: 111

Leu Lys Thr His Thr Thr Arg Thr His Thr
1               5                   10

<210> SEQ ID NO 112
<211> LENGTH: 10
<212> TYPE: PRT
<213> ORGANISM: Homo sapiens

<400> SEQUENCE: 112

Asn Met His Gln Arg Asn His Thr Lys Leu
1               5                   10

<210> SEQ ID NO 113
<211> LENGTH: 9
<212> TYPE: PRT
<213> ORGANISM: Homo sapiens

<400> SEQUENCE: 113

Leu Leu Ala Ala Ile Leu Asp Phe Leu
1               5

<210> SEQ ID NO 114
<211> LENGTH: 10
<212> TYPE: PRT
<213> ORGANISM: Homo sapiens

```
<400> SEQUENCE: 114

Cys Leu Gln Gln Pro Glu Gln Gln Gly Val
1               5                   10

<210> SEQ ID NO 115
<211> LENGTH: 9
<212> TYPE: PRT
<213> ORGANISM: Homo sapiens

<400> SEQUENCE: 115

Asp Leu Asn Ala Leu Leu Pro Ala Val
1               5

<210> SEQ ID NO 116
<211> LENGTH: 9
<212> TYPE: PRT
<213> ORGANISM: Homo sapiens

<400> SEQUENCE: 116

Ala Leu Leu Pro Ala Val Pro Ser Leu
1               5

<210> SEQ ID NO 117
<211> LENGTH: 9
<212> TYPE: PRT
<213> ORGANISM: Homo sapiens

<400> SEQUENCE: 117

Val Leu Asp Phe Ala Pro Pro Gly Ala
1               5

<210> SEQ ID NO 118
<211> LENGTH: 9
<212> TYPE: PRT
<213> ORGANISM: Homo sapiens

<400> SEQUENCE: 118

Cys Met Thr Trp Asn Gln Met Asn Leu
1               5

<210> SEQ ID NO 119
<211> LENGTH: 10
<212> TYPE: PRT
<213> ORGANISM: Homo sapiens

<400> SEQUENCE: 119

Gln Ala Arg Met Phe Pro Asn Ala Pro Tyr
1               5                   10

<210> SEQ ID NO 120
<211> LENGTH: 10
<212> TYPE: PRT
<213> ORGANISM: Homo sapiens

<400> SEQUENCE: 120

Ala Leu Arg Asn Pro Thr Ala Cys Pro Leu
1               5                   10

<210> SEQ ID NO 121
<211> LENGTH: 9
<212> TYPE: PRT
<213> ORGANISM: Homo sapiens

<400> SEQUENCE: 121
```

Tyr Pro Gly Cys Asn Lys Arg Tyr Phe
1               5

<210> SEQ ID NO 122
<211> LENGTH: 15
<212> TYPE: PRT
<213> ORGANISM: Homo sapiens

<400> SEQUENCE: 122

Ala Pro Val Leu Asp Phe Ala Pro Pro Gly Ala Ser Ala Tyr Gly
1               5                   10                  15

<210> SEQ ID NO 123
<211> LENGTH: 9
<212> TYPE: PRT
<213> ORGANISM: Mutated Homo sapiens

<400> SEQUENCE: 123

Tyr Met Phe Pro Asn Ala Pro Tyr Leu
1               5

<210> SEQ ID NO 124
<211> LENGTH: 19
<212> TYPE: PRT
<213> ORGANISM: Mutated Homo sapiens

<400> SEQUENCE: 124

Ser Gly Gln Ala Tyr Met Phe Pro Asn Ala Pro Tyr Leu Pro Ser Cys
1               5                   10                  15

Leu Glu Ser

<210> SEQ ID NO 125
<211> LENGTH: 15
<212> TYPE: PRT
<213> ORGANISM: Mutated Homo sapiens

<400> SEQUENCE: 125

Gln Ala Tyr Met Phe Pro Asn Ala Pro Tyr Leu Pro Ser Cys Leu
1               5                   10                  15

<210> SEQ ID NO 126
<211> LENGTH: 9
<212> TYPE: PRT
<213> ORGANISM: Homo sapiens

<400> SEQUENCE: 126

Tyr Leu Gly Glu Gln Gln Tyr Ser Val
1               5

<210> SEQ ID NO 127
<211> LENGTH: 9
<212> TYPE: PRT
<213> ORGANISM: Homo sapiens

<400> SEQUENCE: 127

Tyr Leu Leu Pro Ala Val Pro Ser Leu
1               5

<210> SEQ ID NO 128
<211> LENGTH: 9
<212> TYPE: PRT
<213> ORGANISM: Homo sapiens

<400> SEQUENCE: 128

Tyr Leu Gly Ala Thr Leu Lys Gly Val
1               5

<210> SEQ ID NO 129
<211> LENGTH: 9
<212> TYPE: PRT
<213> ORGANISM: Homo sapiens

<400> SEQUENCE: 129

Tyr Leu Asn Ala Leu Leu Pro Ala Val
1               5

<210> SEQ ID NO 130
<211> LENGTH: 9
<212> TYPE: PRT
<213> ORGANISM: Homo sapiens

<400> SEQUENCE: 130

Gly Leu Arg Arg Gly Ile Gln Asp Val
1               5

<210> SEQ ID NO 131
<211> LENGTH: 9
<212> TYPE: PRT
<213> ORGANISM: Homo sapiens

<400> SEQUENCE: 131

Lys Leu Tyr Phe Lys Leu Ser His Leu
1               5

<210> SEQ ID NO 132
<211> LENGTH: 9
<212> TYPE: PRT
<213> ORGANISM: Homo sapiens

<400> SEQUENCE: 132

Ala Leu Leu Leu Arg Thr Pro Tyr Val
1               5

<210> SEQ ID NO 133
<211> LENGTH: 9
<212> TYPE: PRT
<213> ORGANISM: Homo sapiens

<400> SEQUENCE: 133

Tyr Met Thr Trp Asn Gln Met Asn Leu
1               5

<210> SEQ ID NO 134
<211> LENGTH: 9
<212> TYPE: PRT
<213> ORGANISM: Homo sapiens

<400> SEQUENCE: 134

Asn Met Tyr Gln Arg Asn Met Thr Lys
1               5

<210> SEQ ID NO 135
<211> LENGTH: 9
<212> TYPE: PRT
<213> ORGANISM: Homo sapiens

<400> SEQUENCE: 135

Asn Met His Gln Arg Val Met Thr Lys
1               5

```
<210> SEQ ID NO 136
<211> LENGTH: 9
<212> TYPE: PRT
<213> ORGANISM: Homo sapiens

<400> SEQUENCE: 136

Asn Met Tyr Gln Arg Val Met Thr Lys
1               5

<210> SEQ ID NO 137
<211> LENGTH: 9
<212> TYPE: PRT
<213> ORGANISM: Homo sapiens

<400> SEQUENCE: 137

Gln Met Tyr Leu Gly Ala Thr Leu Lys
1               5

<210> SEQ ID NO 138
<211> LENGTH: 9
<212> TYPE: PRT
<213> ORGANISM: Homo sapiens

<400> SEQUENCE: 138

Gln Met Asn Leu Gly Val Thr Leu Lys
1               5

<210> SEQ ID NO 139
<211> LENGTH: 9
<212> TYPE: PRT
<213> ORGANISM: Homo sapiens

<400> SEQUENCE: 139

Gln Met Tyr Leu Gly Val Thr Leu Lys
1               5

<210> SEQ ID NO 140
<211> LENGTH: 10
<212> TYPE: PRT
<213> ORGANISM: Homo sapiens

<400> SEQUENCE: 140

Phe Met Tyr Ala Tyr Pro Gly Cys Asn Lys
1               5                   10

<210> SEQ ID NO 141
<211> LENGTH: 10
<212> TYPE: PRT
<213> ORGANISM: Homo sapiens

<400> SEQUENCE: 141

Phe Met Cys Ala Tyr Pro Phe Cys Asn Lys
1               5                   10

<210> SEQ ID NO 142
<211> LENGTH: 10
<212> TYPE: PRT
<213> ORGANISM: Homo sapiens

<400> SEQUENCE: 142

Phe Met Tyr Ala Tyr Pro Phe Cys Asn Lys
1               5                   10
```

<210> SEQ ID NO 143
<211> LENGTH: 10
<212> TYPE: PRT
<213> ORGANISM: Homo sapiens

<400> SEQUENCE: 143

Lys Leu Tyr His Leu Gln Met His Ser Arg
1               5                   10

<210> SEQ ID NO 144
<211> LENGTH: 10
<212> TYPE: PRT
<213> ORGANISM: Homo sapiens

<400> SEQUENCE: 144

Lys Leu Ser His Leu Gln Met His Ser Lys
1               5                   10

<210> SEQ ID NO 145
<211> LENGTH: 10
<212> TYPE: PRT
<213> ORGANISM: Homo sapiens

<400> SEQUENCE: 145

Lys Leu Tyr His Leu Gln Met His Ser Lys
1               5                   10

<210> SEQ ID NO 146
<211> LENGTH: 9
<212> TYPE: PRT
<213> ORGANISM: Homo sapiens

<400> SEQUENCE: 146

Asn Gln Met Asn Leu Gly Ala Thr Leu
1               5

<210> SEQ ID NO 147
<211> LENGTH: 9
<212> TYPE: PRT
<213> ORGANISM: Homo sapiens

<400> SEQUENCE: 147

Asn Leu Met Asn Leu Gly Ala Thr Leu
1               5

<210> SEQ ID NO 148
<211> LENGTH: 9
<212> TYPE: PRT
<213> ORGANISM: Homo sapiens

<400> SEQUENCE: 148

Asn Tyr Met Asn Leu Gly Ala Thr Leu
1               5

<210> SEQ ID NO 149
<211> LENGTH: 15
<212> TYPE: PRT
<213> ORGANISM: Homo sapiens

<400> SEQUENCE: 149

Cys Met Thr Trp Asn Gln Met Asn Leu Gly Ala Thr Leu Lys Gly
1               5                   10                  15

<210> SEQ ID NO 150
<211> LENGTH: 15

```
<212> TYPE: PRT
<213> ORGANISM: Homo sapiens

<400> SEQUENCE: 150

Cys Met Thr Trp Asn Leu Met Asn Leu Gly Ala Thr Leu Lys Gly
1               5                   10                  15

<210> SEQ ID NO 151
<211> LENGTH: 15
<212> TYPE: PRT
<213> ORGANISM: Homo sapiens

<400> SEQUENCE: 151

Trp Asn Leu Met Asn Leu Gly Ala Thr Leu Lys Gly Val Ala Ala
1               5                   10                  15

<210> SEQ ID NO 152
<211> LENGTH: 15
<212> TYPE: PRT
<213> ORGANISM: Homo sapiens

<400> SEQUENCE: 152

Trp Asn Gln Met Asn Leu Gly Ala Thr Leu Lys Gly Val Ala Ala
1               5                   10                  15

<210> SEQ ID NO 153
<211> LENGTH: 15
<212> TYPE: PRT
<213> ORGANISM: Homo sapiens

<400> SEQUENCE: 153

Met Thr Trp Asn Gln Met Asn Leu Gly Ala Thr Leu Lys Gly Val
1               5                   10                  15

<210> SEQ ID NO 154
<211> LENGTH: 15
<212> TYPE: PRT
<213> ORGANISM: Homo sapiens

<400> SEQUENCE: 154

Thr Trp Asn Gln Met Asn Leu Gly Ala Thr Leu Lys Gly Val Ala
1               5                   10                  15

<210> SEQ ID NO 155
<211> LENGTH: 15
<212> TYPE: PRT
<213> ORGANISM: Homo sapiens

<400> SEQUENCE: 155

Cys Met Thr Trp Asn Leu Met Asn Leu Gly Ala Thr Leu Lys Gly
1               5                   10                  15

<210> SEQ ID NO 156
<211> LENGTH: 15
<212> TYPE: PRT
<213> ORGANISM: Homo sapiens

<400> SEQUENCE: 156

Met Thr Trp Asn Leu Met Asn Leu Gly Ala Thr Leu Lys Gly Val
1               5                   10                  15

<210> SEQ ID NO 157
<211> LENGTH: 15
<212> TYPE: PRT
<213> ORGANISM: Homo sapiens
```

```
<400> SEQUENCE: 157

Thr Trp Asn Leu Met Asn Leu Gly Ala Thr Leu Lys Gly Val Ala
1               5                   10                  15

<210> SEQ ID NO 158
<211> LENGTH: 15
<212> TYPE: PRT
<213> ORGANISM: Homo sapiens

<400> SEQUENCE: 158

Trp Asn Leu Met Asn Leu Gly Ala Thr Leu Lys Gly Val Ala Ala
1               5                   10                  15

<210> SEQ ID NO 159
<211> LENGTH: 15
<212> TYPE: PRT
<213> ORGANISM: Homo sapiens

<400> SEQUENCE: 159

Met Thr Trp Asn Tyr Met Asn Leu Gly Ala Thr Leu Lys Gly Val
1               5                   10                  15

<210> SEQ ID NO 160
<211> LENGTH: 15
<212> TYPE: PRT
<213> ORGANISM: Homo sapiens

<400> SEQUENCE: 160

Thr Trp Asn Tyr Met Asn Leu Gly Ala Thr Leu Lys Gly Val Ala
1               5                   10                  15

<210> SEQ ID NO 161
<211> LENGTH: 17
<212> TYPE: PRT
<213> ORGANISM: Homo sapiens

<400> SEQUENCE: 161

Cys Met Thr Trp Asn Gln Met Asn Leu Gly Ala Thr Leu Lys Gly Val
1               5                   10                  15

Ala

<210> SEQ ID NO 162
<211> LENGTH: 9
<212> TYPE: PRT
<213> ORGANISM: Homo sapiens

<400> SEQUENCE: 162

Trp Asn Gln Met Asn Leu Gly Ala Thr
1               5

<210> SEQ ID NO 163
<211> LENGTH: 9
<212> TYPE: PRT
<213> ORGANISM: Homo sapiens

<400> SEQUENCE: 163

Thr Trp Asn Gln Met Asn Leu Gly Ala
1               5

<210> SEQ ID NO 164
<211> LENGTH: 9
<212> TYPE: PRT
<213> ORGANISM: Homo sapiens
```

<400> SEQUENCE: 164

Met Thr Trp Asn Gln Met Asn Leu Gly
1               5

<210> SEQ ID NO 165
<211> LENGTH: 17
<212> TYPE: PRT
<213> ORGANISM: Homo sapiens

<400> SEQUENCE: 165

Cys Met Thr Trp Asn Leu Met Asn Leu Gly Ala Thr Leu Lys Gly Val
1               5                   10                  15

Ala

<210> SEQ ID NO 166
<211> LENGTH: 9
<212> TYPE: PRT
<213> ORGANISM: Homo sapiens

<400> SEQUENCE: 166

Trp Asn Leu Met Asn Leu Gly Ala Thr
1               5

<210> SEQ ID NO 167
<211> LENGTH: 9
<212> TYPE: PRT
<213> ORGANISM: Homo sapiens

<400> SEQUENCE: 167

Met Asn Leu Gly Ala Thr Leu Lys Gly
1               5

<210> SEQ ID NO 168
<211> LENGTH: 9
<212> TYPE: PRT
<213> ORGANISM: Homo sapiens

<400> SEQUENCE: 168

Met Thr Trp Asn Gln Met Asn Leu Gly
1               5

<210> SEQ ID NO 169
<211> LENGTH: 17
<212> TYPE: PRT
<213> ORGANISM: Homo sapiens

<400> SEQUENCE: 169

Cys Met Thr Trp Asn Tyr Met Asn Leu Gly Ala Thr Leu Lys Gly Val
1               5                   10                  15

Ala

<210> SEQ ID NO 170
<211> LENGTH: 9
<212> TYPE: PRT
<213> ORGANISM: Homo sapiens

<400> SEQUENCE: 170

Met Asn Leu Gly Ala Thr Leu Lys Gly
1               5

<210> SEQ ID NO 171
<211> LENGTH: 9

<212> TYPE: PRT
<213> ORGANISM: Homo sapiens

<400> SEQUENCE: 171

Met Thr Trp Asn Gln Met Asn Leu Gly
1               5

<210> SEQ ID NO 172
<211> LENGTH: 9
<212> TYPE: PRT
<213> ORGANISM: Homo sapiens

<400> SEQUENCE: 172

Gly Ala Leu Arg Asn Pro Thr Ala Cys
1               5

<210> SEQ ID NO 173
<211> LENGTH: 9
<212> TYPE: PRT
<213> ORGANISM: Homo sapiens

<400> SEQUENCE: 173

Gly Tyr Leu Arg Asn Pro Thr Ala Cys
1               5

<210> SEQ ID NO 174
<211> LENGTH: 9
<212> TYPE: PRT
<213> ORGANISM: Homo sapiens

<400> SEQUENCE: 174

Gly Ala Leu Arg Asn Pro Thr Ala Leu
1               5

<210> SEQ ID NO 175
<211> LENGTH: 9
<212> TYPE: PRT
<213> ORGANISM: Homo sapiens

<400> SEQUENCE: 175

Tyr Ala Leu Arg Asn Pro Thr Ala Cys
1               5

<210> SEQ ID NO 176
<211> LENGTH: 9
<212> TYPE: PRT
<213> ORGANISM: Homo sapiens

<400> SEQUENCE: 176

Gly Leu Leu Arg Asn Pro Thr Ala Cys
1               5

<210> SEQ ID NO 177
<211> LENGTH: 9
<212> TYPE: PRT
<213> ORGANISM: Homo sapiens

<400> SEQUENCE: 177

Arg Gln Arg Pro His Pro Gly Ala Leu
1               5

<210> SEQ ID NO 178
<211> LENGTH: 9
<212> TYPE: PRT
<213> ORGANISM: Homo sapiens

<400> SEQUENCE: 178

Arg Tyr Arg Pro His Pro Gly Ala Leu
1               5

<210> SEQ ID NO 179
<211> LENGTH: 9
<212> TYPE: PRT
<213> ORGANISM: Homo sapiens

<400> SEQUENCE: 179

Tyr Gln Arg Pro His Pro Gly Ala Leu
1               5

<210> SEQ ID NO 180
<211> LENGTH: 9
<212> TYPE: PRT
<213> ORGANISM: Homo sapiens

<400> SEQUENCE: 180

Arg Leu Arg Pro His Pro Gly Ala Leu
1               5

<210> SEQ ID NO 181
<211> LENGTH: 9
<212> TYPE: PRT
<213> ORGANISM: Homo sapiens

<400> SEQUENCE: 181

Arg Ile Arg Pro His Pro Gly Ala Leu
1               5

<210> SEQ ID NO 182
<211> LENGTH: 9
<212> TYPE: PRT
<213> ORGANISM: Homo sapiens

<400> SEQUENCE: 182

Gly Ala Leu Arg Asn Pro Thr Ala Cys
1               5

<210> SEQ ID NO 183
<211> LENGTH: 9
<212> TYPE: PRT
<213> ORGANISM: Homo sapiens

<400> SEQUENCE: 183

Gly Ala Leu Arg Asn Pro Thr Ala Leu
1               5

<210> SEQ ID NO 184
<211> LENGTH: 9
<212> TYPE: PRT
<213> ORGANISM: Homo sapiens

<400> SEQUENCE: 184

Arg Gln Arg Pro His Pro Gly Ala Leu
1               5

<210> SEQ ID NO 185
<211> LENGTH: 9
<212> TYPE: PRT
<213> ORGANISM: Homo sapiens

<400> SEQUENCE: 185

```
Arg Leu Arg Pro His Pro Gly Ala Leu
1               5

<210> SEQ ID NO 186
<211> LENGTH: 9
<212> TYPE: PRT
<213> ORGANISM: Homo sapiens

<400> SEQUENCE: 186

Arg Ile Arg Pro His Pro Gly Ala Leu
1               5

<210> SEQ ID NO 187
<211> LENGTH: 15
<212> TYPE: PRT
<213> ORGANISM: Homo sapiens

<400> SEQUENCE: 187

Gln Phe Pro Asn His Ser Phe Lys His Glu Asp Pro Met Gly Gln
1               5                   10                  15

<210> SEQ ID NO 188
<211> LENGTH: 15
<212> TYPE: PRT
<213> ORGANISM: Homo sapiens

<400> SEQUENCE: 188

Gln Phe Pro Asn His Ser Phe Lys His Glu Asp Pro Met Gly Gln
1               5                   10                  15

<210> SEQ ID NO 189
<211> LENGTH: 9
<212> TYPE: PRT
<213> ORGANISM: Homo sapiens

<400> SEQUENCE: 189

His Ser Phe Lys His Glu Asp Pro Met
1               5

<210> SEQ ID NO 190
<211> LENGTH: 9
<212> TYPE: PRT
<213> ORGANISM: Homo sapiens

<400> SEQUENCE: 190

His Ser Phe Lys His Glu Asp Pro Tyr
1               5

<210> SEQ ID NO 191
<211> LENGTH: 9
<212> TYPE: PRT
<213> ORGANISM: Homo sapiens

<400> SEQUENCE: 191

His Ser Phe Lys His Glu Asp Pro Lys
1               5

<210> SEQ ID NO 192
<211> LENGTH: 15
<212> TYPE: PRT
<213> ORGANISM: Homo sapiens

<400> SEQUENCE: 192

Lys Arg Pro Phe Met Cys Ala Tyr Pro Gly Cys Tyr Lys Arg Tyr
```

```
1               5                   10                  15
```

<210> SEQ ID NO 193
<211> LENGTH: 15
<212> TYPE: PRT
<213> ORGANISM: Homo sapiens

<400> SEQUENCE: 193

```
Ser Glu Lys Arg Pro Phe Met Cys Ala Tyr Pro Gly Cys Asn Lys
1               5                   10                  15
```

<210> SEQ ID NO 194
<211> LENGTH: 13
<212> TYPE: PRT
<213> ORGANISM: Homo sapiens

<400> SEQUENCE: 194

```
Lys Arg Pro Phe Met Cys Ala Tyr Pro Gly Cys Asn Lys
1               5                   10
```

<210> SEQ ID NO 195
<211> LENGTH: 9
<212> TYPE: PRT
<213> ORGANISM: Homo sapiens

<400> SEQUENCE: 195

```
Phe Met Cys Ala Tyr Pro Gly Cys Asn
1               5
```

<210> SEQ ID NO 196
<211> LENGTH: 9
<212> TYPE: PRT
<213> ORGANISM: Homo sapiens

<400> SEQUENCE: 196

```
Phe Met Cys Ala Tyr Pro Gly Cys Tyr
1               5
```

<210> SEQ ID NO 197
<211> LENGTH: 9
<212> TYPE: PRT
<213> ORGANISM: Homo sapiens

<400> SEQUENCE: 197

```
Phe Met Cys Ala Tyr Pro Gly Cys Lys
1               5
```

<210> SEQ ID NO 198
<211> LENGTH: 449
<212> TYPE: PRT
<213> ORGANISM: Homo sapiens

<400> SEQUENCE: 198

```
Met Gly Ser Asp Val Arg Asp Leu Asn Ala Leu Leu Pro Ala Val
1               5                   10                  15

Ser Leu Gly Gly Gly Gly Gly Cys Ala Leu Pro Val Ser Gly Ala Ala
                20                  25                  30

Gln Trp Ala Pro Val Leu Asp Phe Ala Pro Pro Gly Ala Ser Ala Tyr
            35                  40                  45

Gly Ser Leu Gly Gly Pro Ala Pro Pro Ala Pro Pro Pro Pro
        50                  55                  60

Pro Pro Pro Pro His Ser Phe Ile Lys Gln Glu Pro Ser Trp Gly Gly
65                  70                  75                  80
```

```
Ala Glu Pro His Glu Gln Cys Leu Ser Ala Phe Thr Val His Phe
                 85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Arg Val Pro
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
        435                 440                 445

Leu

<210> SEQ ID NO 199
<211> LENGTH: 453
<212> TYPE: PRT
<213> ORGANISM: Homo sapiens

<400> SEQUENCE: 199
```

```
Ala Ala Glu Ala Ser Ala Glu Arg Leu Gln Gly Arg Arg Ser Arg Gly
1               5                   10                  15
Ala Ser Gly Ser Glu Pro Gln Gln Met Gly Ser Asp Val Arg Asp Leu
            20                  25                  30
Asn Ala Leu Leu Pro Ala Val Pro Ser Leu Gly Gly Gly Gly Gly Cys
            35                  40                  45
Ala Leu Pro Val Ser Gly Ala Ala Gln Trp Ala Pro Val Leu Asp Phe
        50                  55                  60
Ala Pro Pro Gly Ala Ser Ala Tyr Gly Ser Leu Gly Gly Pro Ala Pro
65                  70                  75                  80
Pro Pro Ala Pro Pro Pro Pro Pro Pro Pro His Ser Phe Ile
                85                  90                  95
Lys Gln Glu Pro Ser Trp Gly Gly Ala Glu Pro His Glu Glu Gln Cys
                100                 105                 110
Leu Ser Ala Phe Thr Val His Phe Ser Gly Gln Phe Thr Gly Thr Ala
            115                 120                 125
Gly Ala Cys Arg Tyr Gly Pro Phe Gly Pro Pro Pro Ser Gln Ala
        130                 135                 140
Ser Ser Gly Gln Ala Arg Met Phe Pro Asn Ala Pro Tyr Leu Pro Ser
145                 150                 155                 160
Cys Leu Glu Ser Gln Pro Ala Ile Arg Asn Gln Gly Tyr Ser Thr Val
                165                 170                 175
Thr Phe Asp Gly Thr Pro Ser Tyr Gly His Thr Pro Ser His His Ala
            180                 185                 190
Ala Gln Phe Pro Asn His Ser Phe Lys His Glu Asp Pro Met Gly Gln
        195                 200                 205
Gln Gly Ser Leu Gly Glu Gln Gln Tyr Ser Val Pro Pro Pro Val Tyr
    210                 215                 220
Gly Cys His Thr Pro Thr Asp Ser Cys Thr Gly Ser Gln Ala Leu Leu
225                 230                 235                 240
Leu Arg Thr Pro Tyr Ser Ser Asp Asn Leu Tyr Gln Met Thr Ser Gln
                245                 250                 255
Leu Glu Cys Met Thr Trp Asn Gln Met Asn Leu Gly Ala Thr Leu Lys
            260                 265                 270
Gly His Ser Thr Gly Tyr Glu Ser Asp Asn His Thr Thr Pro Ile Leu
        275                 280                 285
Cys Gly Ala Gln Tyr Arg Ile His Thr His Gly Val Phe Arg Gly Ile
290                 295                 300
Gln Asp Val Arg Arg Val Pro Gly Val Ala Pro Thr Leu Val Arg Ser
305                 310                 315                 320
Ala Ser Glu Thr Ser Glu Lys Arg Pro Phe Met Cys Ala Tyr Pro Gly
                325                 330                 335
Cys Asn Lys Arg Tyr Phe Lys Leu Ser His Leu Gln Met His Ser Arg
            340                 345                 350
Lys His Thr Gly Glu Lys Pro Tyr Gln Cys Asp Phe Lys Asp Cys Glu
        355                 360                 365
Arg Arg Phe Ser Arg Ser Asp Gln Leu Lys Arg His Gln Arg Arg His
    370                 375                 380
Thr Gly Val Lys Pro Phe Gln Cys Lys Thr Cys Gln Arg Lys Phe Ser
385                 390                 395                 400
Arg Ser Asp His Leu Lys Thr His Thr Arg Thr His Thr Gly Glu Lys
                405                 410                 415
```

-continued

```
Pro Phe Ser Cys Arg Trp Pro Ser Cys Gln Lys Lys Phe Ala Arg Ser
            420                 425                 430

Asp Glu Leu Val Arg His His Asn Met His Gln Arg Asn Met Thr Lys
            435                 440                 445

Leu Gln Leu Ala Leu
        450

<210> SEQ ID NO 200
<211> LENGTH: 514
<212> TYPE: PRT
<213> ORGANISM: Homo sapiens

<400> SEQUENCE: 200

Met Gln Asp Pro Ala Ser Thr Cys Val Pro Glu Pro Ala Ser Gln His
1               5                   10                  15

Thr Leu Arg Ser Gly Pro Gly Cys Leu Gln Pro Glu Gln Gln Gly
            20                  25                  30

Val Arg Asp Pro Gly Gly Ile Trp Ala Lys Leu Gly Ala Ala Glu Ala
            35                  40                  45

Ser Ala Glu Arg Leu Gln Gly Arg Arg Ser Arg Gly Ala Ser Gly Ser
        50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Cys Ala Leu Pro Val
                85                  90                  95

Ser Gly Ala Ala Gln Trp Ala Pro Val Leu Asp Phe Ala Pro Pro Gly
            100                 105                 110

Ala Ser Ala Tyr Gly Ser Leu Gly Gly Pro Ala Pro Pro Pro Ala Pro
            115                 120                 125

Pro Pro Pro Pro Pro Pro His Ser Phe Ile Lys Gln Glu Pro
        130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Ser Gln Ala Ser Ser Gly Gln
            180                 185                 190

Ala Arg Met Phe Pro Asn Ala Pro Tyr Leu Pro Ser Cys Leu Glu Ser
            195                 200                 205

Gln Pro Ala Ile Arg Asn Gln Gly Tyr Ser Thr Val Thr Phe Asp Gly
        210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Val Tyr Gly Cys His Thr
            260                 265                 270

Pro Thr Asp Ser Cys Thr Gly Ser Gln Ala Leu Leu Leu Arg Thr Pro
            275                 280                 285

Tyr Ser Ser Asp Asn Leu Tyr Gln Met Thr Ser Gln Leu Glu Cys Met
        290                 295                 300

Thr Trp Asn Gln Met Asn Leu Gly Ala Thr Leu Lys Gly Val Ala Ala
305                 310                 315                 320

Gly Ser Ser Ser Ser Val Lys Trp Thr Glu Gly Gln Ser Asn His Ser
                325                 330                 335
```

```
Thr Gly Tyr Glu Ser Asp Asn His Thr Thr Pro Ile Leu Cys Gly Ala
            340                 345                 350

Gln Tyr Arg Ile His Thr His Gly Val Phe Arg Gly Ile Gln Asp Val
            355                 360                 365

Arg Arg Val Pro Gly Val Ala Pro Thr Leu Val Arg Ser Ala Ser Glu
        370                 375                 380

Thr Ser Glu Lys Arg Pro Phe Met Cys Ala Tyr Pro Gly Cys Asn Lys
385                 390                 395                 400

Arg Tyr Phe Lys Leu Ser His Leu Gln Met His Ser Arg Lys His Thr
                405                 410                 415

Gly Glu Lys Pro Tyr Gln Cys Asp Phe Lys Asp Cys Glu Arg Arg Phe
                420                 425                 430

Ser Arg Ser Asp Gln Leu Lys Arg His Gln Arg Arg His Thr Gly Val
            435                 440                 445

Lys Pro Phe Gln Cys Lys Thr Cys Gln Arg Lys Phe Ser Arg Ser Asp
        450                 455                 460

His Leu Lys Thr His Thr Arg Thr His Thr Gly Glu Lys Pro Phe Ser
465                 470                 475                 480

Cys Arg Trp Pro Ser Cys Gln Lys Lys Phe Ala Arg Ser Asp Glu Leu
                485                 490                 495

Val Arg His His Asn Met His Gln Arg Asn Met Thr Lys Leu Gln Leu
                500                 505                 510

Ala Leu

<210> SEQ ID NO 201
<211> LENGTH: 168
<212> TYPE: PRT
<213> ORGANISM: Homo sapiens

<400> SEQUENCE: 201

Met Gly His His His His His His His His Ser Ser Gly His
1               5                   10                  15

Ile Glu Gly Arg His Met Arg Arg Val Pro Gly Val Ala Pro Thr Leu
            20                  25                  30

Val Arg Ser Ala Ser Glu Thr Ser Glu Lys Arg Pro Phe Met Cys Ala
        35                  40                  45

Tyr Pro Gly Cys Asn Lys Arg Tyr Phe Lys Leu Ser His Leu Gln Met
    50                  55                  60

His Ser Arg Lys His Thr Gly Glu Lys Pro Tyr Gln Cys Asp Phe Lys
65                  70                  75                  80

Asp Cys Glu Arg Arg Phe Phe Arg Ser Asp Gln Leu Lys Arg His Gln
                85                  90                  95

Arg Arg His Thr Gly Val Lys Pro Phe Gln Cys Lys Thr Cys Gln Arg
            100                 105                 110

Lys Phe Ser Arg Ser Asp His Leu Lys Thr His Thr Arg Thr His Thr
        115                 120                 125

Gly Glu Lys Pro Phe Ser Cys Arg Trp Pro Ser Cys Gln Lys Lys Phe
    130                 135                 140

Ala Arg Ser Asp Glu Leu Val Arg His His Asn Met His Gln Arg Asn
145                 150                 155                 160

Met Thr Lys Leu Gln Leu Ala Leu
                165

<210> SEQ ID NO 202
```

```
<211> LENGTH: 18
<212> TYPE: PRT
<213> ORGANISM: Homo sapiens

<400> SEQUENCE: 202

Gly Ala Thr Leu Lys Gly Val Ala Ala Gly Ser Ser Ser Val Lys
1               5                  10                  15

Trp Thr

<210> SEQ ID NO 203
<211> LENGTH: 15
<212> TYPE: PRT
<213> ORGANISM: Homo sapiens

<400> SEQUENCE: 203

Leu Lys Gly Val Ala Ala Gly Ser Ser Ser Val Lys Trp Thr
1               5                  10                  15

<210> SEQ ID NO 204
<211> LENGTH: 9
<212> TYPE: PRT
<213> ORGANISM: Homo sapiens

<400> SEQUENCE: 204

Tyr Ala Leu Arg Asn Pro Thr Ala Cys
1               5
```

METHODS AND COMPOSITIONS FOR TREATING CANCER

CROSS-REFERENCE TO RELATED APPLICATIONS

This application is a National Phase Application of PCT International Application No. PCT/US16/62865, International Filing Date Nov. 18, 2016, claiming priority of U.S. Provisional Patent Application 62/258,134, filed Nov. 20, 2015, all of which are incorporated herein by reference in their entirety.

FIELD OF INVENTION

This invention provides methods of treating, reducing the incidence of, and inducing immune responses against a WT1-expressing cancer, and compositions useful for the same purposes.

SUMMARY OF THE INVENTION

This invention provides methods of treating, reducing the incidence of, and inducing immune responses against a WT1-expressing cancer, and compositions including immunogenic compositions useful for the same purposes. In one embodiment, the present invention provides methods for such use comprising administering to a subject in need thereof (a) one or more WT1 peptides, or cytotoxic T cells (CTLs) against a WT1-expressing cancer, and (b) one or more checkpoint inhibitors. The one or more WT1 peptides can be administered to the subject by administering one or more agents to the subject resulting in delivery of one or more WT1 peptides and induction of an immune response against the WT1-expressing cancer. Examples of these WT1 delivery agents that may be used include: (i) an isolated WT1 peptide, (ii) a nucleic acid encoding the at least one WT1 peptide, and (iii) an immune cell comprising or presenting the at least one WT1 peptide or nucleic acid encoding the at least one WT1 peptide.

The one or more WT1 peptides may be native peptides which are fragments of the WT1 protein, or they may be such peptides with one or more modifications that may enhance the immunogenicity thereof. Such modifications may be amino acid changes (e.g., heteroclitic peptides), or any other modification. CTLs include WT1-specific CTLs that are made in vitro or ex vivo or they may be obtained from a donor. The WT1 delivery agents or CTLs may be provided in a composition with a carrier, excipient or diluent, among which may be an adjuvant. Non-limiting selections of the peptide component used in the methods and compositions embodied herein are described herein below.

The one or more checkpoint inhibitor (also known as an immune checkpoint inhibitor) is a compound or agent that blocks or inhibits immune checkpoint proteins. Non-limiting examples of compounds or agents that are checkpoint inhibitors include small molecules, peptides, and antibodies. Non-limiting examples of antibodies include nivolumab (OPDIVO), pembrolizumab (KEYTRUDA), pidilizumab (CT-011), MEDI0680 (AMP-514), AMP-224, AUNP-12, BMS 936559, atezolizumab (MPDL3280A), durvalumab (MEDI4736), avelumab (MSB0010718C), BMS935559 (MDX-1105), rHIgM12B7, BMS-986016, GSK2831781, IMP321, lirilumab (BMS-986015), IPH2101 (1-7F9), Indoximod (NLG 9189), NLG 919, INCB024360, PF-05082566, Urelumab (BMS-663513), and MEDI6469.

In one embodiment, methods are embodied in which the one or more WT1 delivery agents or CTLs, and the one or more checkpoint inhibitor, are each administered to a subject according to a schedule that maximally benefits the subject. The one or more WT1 delivery agents or CTLs and the one or more checkpoint inhibitors are therefore not necessarily administered at the same time, or even in the same composition, or each for the same duration, or each by the same route. Each WT1 peptide may be administered in accordance with a particular schedule, as may be each checkpoint inhibitor. In one embodiment, the dosing schedules of the at least one WT1 peptide and the at least one checkpoint inhibitor are concurrent. In one embodiment, the dosing schedules of the at least one WT1 peptide and the at least one checkpoint inhibitor overlap. In one embodiment, at least one WT1 delivery agent or CTL and at least one checkpoint inhibitor are present in the same composition. In one embodiment, the methods embodied herein provide an enhanced or increased ability for treating, reducing the incidence of, and inducing immune responses against a WT1-expressing cancer, than the WT1 delivery agent(s) or CTLs and checkpoint inhibitor(s) alone. In one embodiment, the ability for treating, reducing the incidence of, and inducing immune responses against a WT1-expressing cancer provided by the methods described herein are greater than combination of the effect of the WT1 delivery agent(s) or CTLs alone and the checkpoint inhibitor(s) alone.

The dose level and dosing schedule of the WT1 delivery agent or CTLs and that of the checkpoint inhibitor, the route of administration, and other aspects of administration are optimized for maximal benefit to the subject. The embodiments herein provide improved methods of treating, reducing the incidence of, and inducing immune responses against a WT1-expressing cancer, and improved compositions useful for the same purposes.

Cancers amenable to the methods embodied herein are any cancers that express the WT1 protein or a fragment thereof. In one embodiment, the cancer is ovarian cancer. In another embodiment, the cancer is mesothelioma. In another embodiment, the cancer is leukemia. In other embodiments, the cancer is Wilms' tumor, acute myelogenous leukemia (AML), chronic myeloid leukemia (CML), myelodysplastic syndrome (MDS), melanoma, stomach cancer, prostate cancer, biliary cancer, urinary system cancer, glioblastoma, soft tissue sarcoma, osteosarcoma, or non-small cell lung cancer (NSCLC).

DETAILED DESCRIPTION OF THE INVENTION

This invention provides methods of treating, reducing the incidence of, and inducing immune responses against a WT1-expressing cancer, and compositions including immunogenic compositions useful for the same purposes. In one embodiment, the present invention provides methods for such use comprising administering to a subject in need thereof (a) one or more WT1 peptides or cytotoxic T cells (CTLs) thereto, and (b) one or more checkpoint inhibitors. The one or more WT1 peptides can be administered to the subject by administering one or more agents to the subject resulting in delivery of one or more WT1 peptides and induction of an immune response against the WT1-expressing cancer. Examples of these WT1 delivery agents that may be used include: (i) an isolated WT1 peptide, (ii) a nucleic acid encoding the at least one WT1 peptide, and (iii) an immune cell comprising or presenting the at least one WT1 peptide or nucleic acid encoding the at least one WT1 peptide.

Ovarian cancer is one of the most common gynecologic malignancies and the fifth most frequent cause of cancer death in women in the United States. Over 22,000 cases are diagnosed annually, and there are an estimated 15,500 deaths per year [1]. The majority of patients have widespread disease at presentation [2]. The 5-year survival for advanced-stage disease remains less than 30% [1]. Although a complete clinical remission following initial chemotherapy can be anticipated for many patients, a review of second-look laparotomy when it was often performed as a matter of routine care indicates that less than 50% of patients are actually free of disease [3]. Furthermore, nearly half of patients with a negative second look procedure relapse and require additional treatment [4]. Many patients will achieve a second complete clinical response with additional chemotherapy. However, almost all patients will relapse after a short remission interval of 9-11 months. [5]. Effective strategies to prolong remission or to prevent relapse are required, as subsequent remissions are of progressively shorter duration until chemotherapy resistance broadly develops [2].

Both antibody and T cell effectors have been shown to provide benefit in ovarian cancer models. Antibodies have been noted to curtail early tissue invasion [6]. Preclinical models have also demonstrated the clearance of circulating tumor cells and the elimination of systemic micro metastasis through the use of both passively administered and vaccine induced antibodies. With regards to T cell effectors, a globally activated immune response has been shown to be associated with improved clinical outcome in patients with advanced ovarian cancer. Zhang et al showed that the presence of tumor infiltrating T cells within tumor cell islets was associated with improvement in both progression free and overall survival [7]. Conversely, the infiltration of T-regulatory cells confers a worse prognosis [8].

Data in patients with ovarian cancer in second or greater remission confirms them to relapse in a predictable fashion [9]. In recent years, ovarian cancer has been targeted by a variety of novel immune based approaches. Antibody therapy has included oregovomab [10] which is a monoclonal antibody therapy targeting the CA125 antigen; abagovomab [11] which is an anti-idiotypic antibody targeting CA-125; and trastuzumab [12] which is a monoclonal humanized anti-HER2 antibody. Other strategies have included cytokine therapy such as Interferon-γ [13, 14] and IL-2 [15]. Active immunization with other antigens such as Lewis y [16], MUC1 [17], the HLA restricted peptide NY-ESO-1b [18] and the KH-1-KLH conjugate have also been evaluated. Previous strategies have been ineffective and new therapeutic modalities are needed to increase the efficacy of therapies for ovarian as well as numerous other cancers that are ineffectively treated with currently available therapies.

WT1 refers to Wilms' tumor 1 or the gene product of the WT1 gene. The Wilms' tumor suppressor gene, WT1, was first identified in childhood renal tumors, but WT1 is also highly expressed in multiple other hematologic malignancies and solid tumors including mesothelioma [19, 20]. WT1 was originally identified by cDNA mapping to a region of chromosome 11p13. The WT1 cDNA encodes a protein containing four Kruppel zinc fingers and contains a complex pattern of alternative splicing resulting in four different transcription factors. Each WT1 isoform has different DNA binding and transcriptional activities [21], and can positively or negatively regulate various genes involved in cellular proliferation, differentiation, apoptosis, organ development and sex determination. WT1 is normally expressed in tissues of the mesodermal origin during embryogenesis including the kidney, gonads, heart, mesothelium and spleen [22]. In normal adult tissues, WT1 expression is limited to low levels in the nuclei of normal CD34+ hematopoietic stem cells, myoepithelial progenitor cells, renal podocytes and some cells in the testis and ovary [23]. WT1 is highly homologous in mice and humans (96% at the amino acid level) and has similar tissue distribution and function [24, 25]. Although originally described as a tumor suppressor gene, the WT1 proteins appear to be involved in tumorigenesis.

The strong expression of WT1 protein in ovarian cancer coupled with its proposed mechanism of action makes it a rational target for immunotherapy, among many other cancers that also express WT1 protein, such as but not limited to mesothelioma, leukemia, Wilms' tumor, acute myelogenous leukemia (AML), chronic myeloid leukemia (CML), myelodysplastic syndrome (MDS), melanoma, stomach cancer, prostate cancer, biliary cancer, urinary system cancer, glioblastoma, soft tissue sarcoma, osteosarcoma, and non-small cell lung cancer (NSCLC). In ovarian cancer, the expression is so frequent that pathologists routinely use immunohistochemical stains for WT1 (with a standardized convention for describing expression and determining as "positive" or "negative" to help distinguish epithelial ovarian cancers from other tumors. WT1 is a particularly sensitive and specific marker for serous ovarian cancer [26]. Ovarian tissue microarrays suggest that 70-80% of serous ovarian cancers express WT1 such that the majority of patients will have the target and be eligible for study participation.

The one or more WT1 peptides useful for the purposes herein may be native peptides which are fragments of the WT1 protein. In one embodiment, the WT1 peptide is RSDELVRHHNMHQRNMTKL (SEQ ID NO:1), PGCNKRYFKLSHLQMHSRKHTG (SEQ ID NO:2), LVRHHNMHQRNMTKL (SEQ ID NO:3) or NKRYFKLSHLQMHSR (SEQ ID NO:4). In another embodiment the peptide is SGQARMFPNAPYLPSCLES (SEQ ID NO:5) or QARMFPNAPYLPSCL (SEQ ID NO:6). In another embodiment, the peptide is RMFPNAPYL (SEQ ID NO:7), SLGEQQYSV (SEQ ID NO:8), ALLPAVPSL (SEQ ID NO:9), NLGATLKGV (SEQ ID NO:10), DLNALLPAV (SEQ ID NO:11), GVFRGIQDV (SEQ ID NO:12), KRYFKLSHL (SEQ ID NO:13), ALLLRTPYS (SEQ ID NO:14), CMTWMQMNL (SEQ ID NO:15), NMHQRNMTK (SEQ ID NO:16), QMNLGATLK (SEQ ID NO:17), FMCAYPGCNK (SEQ ID NO:18), or KLSHLQMHSR (SEQ ID NO:19).

In another embodiment, the WT1 peptide is NQMNLGATL (SEQ ID NO:20), NLMNLGATL (SEQ ID NO:21), NYMNLGATL (SEQ ID NO:22), CMTWNQMNLGATLKG (SEQ ID NO:23), CMTWNLMNLGATLKG (SEQ ID NO:24), WNQMNLGATLKGVAA (SEQ ID NO:25), WNLMNLGATLKGVAA (SEQ ID NO:26), MTWNQMNLGATLKGV (SEQ ID NO:27), TWNQMNLGATLKGVA (SEQ ID NO:28), CMTWNLMNLGATLKG (SEQ ID NO:29), MTWNLMNLGATLKGV (SEQ ID NO:30), TWNLMNLGATLKGVA (SEQ ID NO:31), WNLMNLGATLKGVAA (SEQ ID NO:32), MTWNYMNLGATLKGV (SEQ ID NO:33), TWNYMNLGATLKGVA (SEQ ID NO:34), CMTWNQMNLGATLKGVA (SEQ ID NO:35), WNQMNLGAT (SEQ ID NO:36), TWNQMNLGA (SEQ ID NO:37), MTWNQMNLG (SEQ ID NO:38), CMTWNLMNLGATLKGVA (SEQ ID NO:39), WNLMNLGAT (SEQ ID NO:40), MNLGATLKG (SEQ ID NO:41), MTWNQMNLG (SEQ ID NO:42), CMTWNYMNLGATLKGVA (SEQ ID NO:43), MNLGATLKG (SEQ ID NO:44), MTWNQMNLG (SEQ ID NO:45), GALRNPTAC (SEQ ID NO:46), GYLRNPTAC (SEQ ID NO:47), GALRNPTAL (SEQ ID NO:48), YALRNPTAC (SEQ ID NO:49), GLLRNPTAC (SEQ ID NO:50), RQRPHPGAL (SEQ ID NO:51), RYRPHPGAL (SEQ ID NO:52), YQRPHPGAL (SEQ ID NO:53), RLRPHPGAL (SEQ ID NO:54), RIRPHPGAL (SEQ ID NO:55), GALRNPTAC (SEQ ID NO:56), GALRNPTAL (SEQ ID NO:57), RQRPHPGAL (SEQ ID NO:58), RLRPHPGAL (SEQ ID NO:59), RIRPHPGAL (SEQ ID NO:60), QFPNHSFKHEDPMGQ (SEQ ID NO:61), QFPNHSFKHEDPMGQ (SEQ ID NO:62), HSFKHEDPM (SEQ ID NO:63), HSFKHEDPY (SEQ ID NO:64), HSFKHEDPK (SEQ ID NO:65), KRPFMCAYPGCYKRY (SEQ ID NO:66), SEKRPFMCAYPGCNK (SEQ ID NO:67), KRPFMCAYPGCNK (SEQ ID NO:68), FMCAYPGCN (SEQ ID NO:69), FMCAYPGCY (SEQ ID NO:70), or FMCAYPGCK (SEQ ID NO:71).

In another embodiment, the WT1 peptide is from among RQRPHPGAL (SEQ ID NO:72), GALRNPTAC (SEQ ID NO:73), PLPHFPPSL (SEQ ID NO:74), HFPPSLPPT (SEQ ID NO:75), THSPTHPPR (SEQ ID NO:76), AILDFLLLQ (SEQ ID NO:77), PGCLQQPEQ (SEQ ID NO:78), PGCLQQPEQQG (SEQ ID NO:79), KLGAAEASA (SEQ ID NO:80), ASGSEPQQM (SEQ ID NO:81), RDLNALLPAV (SEQ ID NO:82), GGCALPVSGA (SEQ ID NO:83), GAAQWAPVL (SEQ ID NO:84), LDFAPPGAS (SEQ ID NO:85), LDFAPPGASAY (SEQ ID NO:86), SAYGSLGGP (SEQ ID NO:87), PAPPPPPPP (SEQ ID NO:88), ACRYGPFGP (SEQ ID NO:89), SGQARMFPN (SEQ ID NO:90), RMFPNAPYL (SEQ ID NO:91), PSCLESQPA (SEQ ID NO:92), NQGYSTVTF (SEQ ID NO:93), HHAAQFPNH (SEQ ID NO:94), HSFKHEDPM (SEQ ID NO:95), CHTPTDSCT (SEQ ID NO:96), CTGSQALLL (SEQ ID NO:97), TDSCTGSQA (SEQ ID NO:98), RTPYSSDNL (SEQ ID NO:99), NLYQMTSQLE (SEQ ID NO:100), WNQMNLGAT (SEQ ID NO:101), NQMNLGATL (SEQ ID NO:102), WNQMNLGATLK (SEQ ID NO:103), CMTWNQMNLGATLKG (SEQ ID NO:104), NLGATLKGV (SEQ ID NO:105), LGATLKGVAA (SEQ ID NO:106), TLGVAAGS (SEQ ID NO:107), GYESDNHTT (SEQ ID NO:108), FMCAYPGCNK (SEQ ID NO:109), KRPFMCAYPGC (SEQ ID NO:110), RKFSRSDHL (SEQ ID NO:111), LKTHTTRTHT (SEQ ID NO:112), NMHQRNHTKL (SEQ ID NO:113), LLAAILDFL (SEQ ID NO:114), CLQQPEQGV (SEQ ID NO:115), DLNALLPAV (SEQ ID NO:116), ALLPAVPSL (SEQ ID NO:117), VLDFAPPGA (SEQ ID NO:118), CMTWNQMNL (SEQ ID NO:119), QARMFPNAPY (SEQ ID NO:120), ALRNPTACPL (SEQ ID NO:121), YPGCNKRYF (SEQ ID NO:122) or APVLDFAPPGASAYG (SEQ ID NO:123).

In another embodiment, the WT1 peptide is any native WT1 peptide described in WO2005053618, WO2007047763, WO2007047764, WO2007120673, US20060084609, WO2014113490 and WO2013106834. The foregoing are incorporated herein by reference in their entireties.

In another embodiment, the WT1 peptide is any native WT1 peptide described in US20110070251A1, U.S. Pat. No. 7,063,854B1, U.S. Pat. Nos. 7,063,854, 7,901,693, 7,662,386, 7,063,854, 7,115,272, 7,368,119, 7,329,410, 7,144,581, 7,323,181, 7,655,249, 7,553,494, 7,608,685, 7,380,871, 7,030,212, 7,807,792, 7,517,950, US2010/0166738, US2011/0070251, US2009/0143291 and WO2003037060. The foregoing are incorporated herein by reference in their entireties.

In another embodiment, the WT1 peptide is any native WT1 peptide described in U.S. Pat. No. 7,666,985B2, US20080070835A1, US20070128207A1, U.S. Pat. No. 7,915,393B2, US20110136141A1, U.S. Pat. No. 7,598,221B2, US20100111986A1, US20100092522A1, US20030082194A1 and WO2001025273A2. The foregoing are incorporated herein by reference in their entireties.

The one or more WT1 peptides may be a modified WT1 peptide fragment, such as containing one or more heteroclitic modifications to enhance immunogenicity against the native peptide sequence. In one embodiment, the WT1 peptide is YMFPNAPYL (SEQ ID NO:124). In another embodiment the peptide is SGQAYMFPNAPYLPSCLES (SEQ ID NO:125). In another embodiment the peptide is QAYMFPNAPYLPSCL (SEQ ID NO:126). In another embodiment, the peptide is any of among YLGEQQYSV (SEQ ID NO:127), YLLPAVPSL (SEQ ID NO:128), YLGATLKGV (SEQ ID NO:129), YLNALLPAV (SEQ ID NO:130), GLRRGIQDV (SEQ ID NO:131), KLYFKLSHL (SEQ ID NO:132), ALLLRTPYV (SEQ ID NO:133), YMTWNQMNL (SEQ ID NO:134), NMYQRNMTK (SEQ ID NO:135), NMHQRVMTK (SEQ ID NO:136), NMYQRVMTK (SEQID NO: 137), QMYLGATLK (SEQ ID NO:138), QMNLGVTLK (SEQ ID NO:139), QMYLGVTLK (SEQ ID NO: 140), FMYAYPGCNK (SEQ ID NO:141), FMCAYPFCNK (SEQ ID NO:142), FMYAYPFCNK (SEQ ID NO:143), KLYHLQMHSR (SEQ ID NO:144), KLSHLQMHSK (SEQ ID NO:145), and KLYHLQMHSK (SEQ ID NO:146).

In another embodiment, the WT1 peptide is any modified WT1 peptide from among NQMNLGATL (SEQ ID NO:147), NLMNLGATL (SEQ ID NO:148), NYMNLGATL (SEQ ID NO:149), CMTWNQMNLGATLKG (SEQ ID NO:150), CMTWNLMNLGATLKG (SEQ ID NO:151), WNQMNLGATLKGVAA (SEQ ID NO:152), WNLMNLGATLKGVAA (SEQ ID NO:153), MTWNQMNLGATLKGV (SEQ ID NO:154), TWNQMNLGATLKGVA (SEQ ID NO:155), CMTWNLMNLGATLKG (SEQ ID NO:156), MTWNLMNLGATLKGV (SEQ ID NO:157), TWNLMNLGATLKGVA (SEQ ID NO:158), WNLMNLGATLKGVAA (SEQ ID NO:159), MTWNYMNLGATLKGV (SEQ ID NO:160), TWNYMNLGATLKGVA (SEQ ID NO:161), CMTWNQMNLGATLKGVA (SEQ ID NO:162), WNQMNLGAT (SEQ ID NO:163), TWNQMNLGA (SEQ ID NO:164), MTWNQMNLG (SEQ ID NO:165), CMTWNLMNLGATLKGVA (SEQ ID NO:166), WNLMNLGAT (SEQ ID NO:167), MNLGATLKG (SEQ ID NO:168), MTWNQMNLG (SEQ ID NO:169), CMTWNYMNLGATLKGVA (SEQ ID NO:170), MNLGATLKG (SEQ ID NO:171), MTWNQMNLG (SEQ ID NO:172), GALRNPTAC (SEQ ID NO:173), GYLRNPTAC (SEQ ID NO:174), GALRNPTAL (SEQ ID NO:175), YALRNPTAC (SEQ ID NO:176), GLLRNPTAC (SEQ ID NO:177), RQRPHPGAL (SEQ ID NO:178), RYRPHPGAL (SEQ ID NO:179), YQRPHPGAL (SEQ ID NO:180), RLRPHPGAL (SEQ ID NO:181), RIRPHPGAL (SEQ ID NO:182), GALRNPTAC (SEQ ID NO:183), GALRNPTAL (SEQ ID NO:184), RQRPHPGAL (SEQ ID NO:185), RLRPHPGAL (SEQ ID NO:186), RIRPHPGAL (SEQ ID NO:187), QFPNHSFKHEDPMGQ (SEQ ID NO:188), QFPNHSFKHEDPMGQ (SEQ ID NO:189), HSFKHEDPM (SEQ ID NO:190), HSFKHEDPY (SEQ ID NO:191), HSFKHEDPK (SEQ ID NO:192), KRPFMCAYPGCYKRY (SEQ ID NO:194), SEKRPFMCAYPGCNK (SEQ ID NO:194), KRPFMCAYPGCNK (SEQ ID NO:195), FMCAYPGCN (SEQ ID NO:196), FMCAYPGCY (SEQ ID NO:197), or FMCAYPGCK (SEQ ID NO:198).

In another embodiment, the WT1 peptide is any modified WT1 peptide described in WO2005053618, WO2007047763, WO2007047764, WO2007120673, US20060084609, WO2014113490 and WO2013106834. The foregoing are incorporated herein by reference in their entireties.

In another embodiment, the WT1 peptide is any modified WT1 peptide described in US20110070251A1, U.S. Pat. No. 7,063,854B1, U.S. Pat. Nos. 7,063,854, 7,901,693, 7,662,386, 7,063,854, 7,115,272, 7,368,119, 7,329,410, 7,144,581, 7,323,181, 7,655,249, 7,553,494, 7,608,685, 7,380,871, 7,030,212, 7,807,792, 7,517,950, US2010/0166738, US2011/0070251, US2009/0143291 and WO2003037060. The foregoing are incorporated herein by reference in their entireties.

In another embodiment, the WT1 peptide is any modified WT1 peptide described in U.S. Pat. No. 7,666,985B2, US20080070835A1, US20070128207A1, U.S. Pat. No. 7,915,393B2, US20110136141A1, U.S. Pat. No. 7,598,221B2, US20100111986A1, US20100092522A1, US20030082194A1 and US2001025273A2. The foregoing are incorporated herein by reference in their entireties.

The one or more WT1 peptides useful for the purposes described herein may be a single peptide or a combination of peptides. Each of the peptides may be a native WT1 peptide or a modified WT1 peptide. If two or more peptides are used, each may be administered individually (in separate formulations) or in a combination with another one or more peptides (in the same formulation). The one or more peptides may be administered in combination with a carrier, diluent or excipient. In one embodiment, the peptide is administered in combination with an adjuvant. Each peptide may be administered with a different adjuvant or combination of adjuvants, or peptides may be administered in a combination of two or more peptides, with an adjuvant of combination of adjuvants. The immunogen or composition containing the one or more peptides may be referred to herein as a vaccine, a peptide vaccine, a WT1 vaccine, and the like.

The adjuvant may be of any class such as alum salts and other mineral adjuvants, bacterial products or bacteria-derived adjuvants, tensoactive agents (e.g., saponins), oil-in-water (o/w) and water-in-oil (w/o) emulsions, liposome adjuvants, cytokines (e.g., IL-2, GM-CSF, IL-12, and IFN-gamma), and alpha-galactosylceramide analogs. Nonlimiting examples of adjuvants include Montanide emulsions, QS21, Freund's complete or incomplete adjuvant, aluminum phosphate, aluminum hydroxide, *Bacillus* Calmette-Guerin (BCG), and alum. In one embodiment, the adjuvant is an agent that enhances the immune system's CTL response against the WT1 peptide, such as the surfactant mannide monooleate containing vegetable-grade (VG) oleic acid derived from olive oil (Montanide ISA 51 VG w/o emulsion). The adjuvant may be administered in the same composition as the one or more WT1 peptides, or in the same composition as the one or more checkpoint inhibitors, or in the same composition as both the one or more WT1 peptides and the one or more checkpoint inhibitors, or in a composition separate from the one or more WT1 peptides and one or more checkpoint inhibitors.

In one embodiment, the one or more WT1 peptides useful for the purposes herein is a combination of any two peptides from among YMFPNAPYL (SEQ ID NO:124), RSDELVRHHNMHQRNMTKL (SEQ ID NO:1), PGCNK-RYFKLSHLQMHSRKHTG (SEQ ID NO: 2) and SGQAYMFPNAPYLPSCLES (SEQ ID NO:125). In one embodiment, the one or more WT1 peptides useful for the purposes herein is a combination of any three peptides from among YMFPNAPYL (SEQ ID NO:124), RSDELVRHHNMHQRNMTKL (SEQ ID NO:1), PGCNK-RYFKLSHLQMHSRKHTG (SEQ ID NO: 2) and SGQAYMFPNAPYLPSCLES (SEQ ID NO:125). In one embodiment, the one or more WT1 peptides useful for the purposes herein is a combination of the following four peptides: YMFPNAPYL (SEQ ID NO:124), RSDELVRHHNMHQRNMTKL (SEQ ID NO:1), PGCNK-RYFKLSHLQMHSRKHTG (SEQ ID NO: 2) and SGQAYMFPNAPYLPSCLES (SEQ ID NO:125). In one embodiment, any one or more peptides may be used together with any of the aforementioned combinations for the purposes herein.

In one embodiment, WT1 peptide comprises the amino acid sequence SGQAYMFPNAPYLPSCLES (SEQ ID NO:125), and wherein the peptide has one or more point mutations in a primary or secondary anchor residue of an HLA class I or class II binding motif. In one embodiment, the WT1 peptide has at least 83% sequence identity with the amino acid sequence SGQAYMFPNAPYLPSCLES (SEQ ID NO: 125). In one embodiment, the WT1 peptide is 20-26 amino acids in length and comprises the amino acid sequence SGQAYMFPNAPYLPSCLES (SEQ ID NO:125). In another embodiment, the WT1 peptide is 17 or 18 amino acids in length and comprises a fragment of the amino acid sequence SGQAYMFPNAPYLPSCLES (SEQ ID NO:125). In another embodiment, the WT1 peptide has at least 88% sequence identity, or at least 93% sequence identity, with the amino acid sequence SGQAYMFPNAPYLPSCLES (SEQ ID NO:125). In another embodiment, any of the aforementioned peptides has one or more point mutations in a primary or secondary anchor residue of the HLA class I binding motif. In one embodiment, the peptide has a point mutation at position 2 or 9 of the class I binding motif, or in secondary anchor residue position 1, 3, 4, 5, 6, 7 or 8 of the class I binding motif. In one embodiment, the peptide, position 1 of the HLA class I binding motif is changed to glycine, threonine or phenylalanine; in one embodiment, position 2 of the HLA class I binding motif is changed to leucine or isoleucine; in one embodiment, position 6 of the HLA class I binding motif is changed to valine, glutamine or histidine; or in one embodiment, position 9 of the HLA class I binding motif is changed to valine, alanine, threonine, isoleucine, or cysteine.

In one embodiment, the one or more WT1 peptides useful for purposes herein is a combination of two, three, or four peptides from among YMFPNAPYL (SEQ ID NO:124), RSDELVRHHNMHQRNMTKL (SEQ ID NO:1), PGCNK-RYFKLSHLQMHSRKHTG (SEQ ID NO:125) and SGQAYMFPNAPYLPSCLES (SEQ ID NO: 2), in combination with one or more native or modified WT1 peptides from among those disclosed in WO2014113490, such as NQMNLGATL (SEQ ID NO:147), NLMNLGATL (SEQ ID NO:148), NYMNLGATL (SEQ ID NO:149), CMTWNQMNLGATLKG (SEQ ID NO:150), CMTWNLMNLGATLKG (SEQ ID NO:151), WNQMNL-GATLKGVAA (SEQ ID NO:152), WNLMNL-GATLKGVAA (SEQ ID NO:153), MTWNQMNL-GATLKGV (SEQ ID NO:154), TWNQMNLGATLKGVA (SEQ ID NO:155), CMTWNLMNLGATLKG (SEQ ID NO:156), MTWNLMNLGATLKGV (SEQ ID NO:157), TWNLMNLGATLKGVA (SEQ ID NO:158), WNLMNL-GATLKGVAA (SEQ ID NO:159), MTWNYMNL- GATLKGV (SEQ ID NO:1260), TWNYMNLGATLKGVA (SEQ ID NO:161), CMTWNQMNLGATLKGVA (SEQ ID NO:162), WNQMNLGAT (SEQ ID NO:163), TWNQMNLGA (SEQ ID NO:164), MTWNQMNLG (SEQ ID NO:165), CMTWNLMNLGATLKGVA (SEQ ID NO:166), WNLMNLGAT (SEQ ID NO:167), MNLGATLKG (SEQ ID NO:168), MTWNQMNLG (SEQ ID NO:169), CMTWNYMNLGATLKGVA (SEQ ID NO:170), MNLGATLKG (SEQ ID NO:171), MTWNQMNLG (SEQ ID NO:172), GALRNPTAC (SEQ ID NO:173), GYLRNPTAC (SEQ ID NO:174), GALRNPTAL (SEQ ID NO:175), YALRNPTAC (SEQ ID NO:176), GLLRNPTAC (SEQ ID NO:177), RQRPHPGAL (SEQ ID NO:178), RYRPHPGAL (SEQ ID NO:179), YQRPHPGAL (SEQ ID NO:180), RLRPHPGAL (SEQ ID NO:181), RIRPHPGAL (SEQ ID NO:182), GALRNPTAC (SEQ ID NO:183), GALRNPTAL (SEQ ID NO:184), RQRPHPGAL (SEQ ID NO:185), RLRPHPGAL (SEQ ID NO:186), RIRPHPGAL (SEQ ID NO:187), QFPNHSFKHEDPMGQ (SEQ ID NO:188), QFPNHSFKHEDPMGQ (SEQ ID NO:189), HSFKHEDPM (SEQ ID NO:190), HSFKHEDPY (SEQ ID NO:191), HSFKHEDPK (SEQ ID NO:192), KRPFMCAYPGCYKRY (SEQ ID NO:194), SEKRPFMCAYPGCNK (SEQ ID NO:194), KRPFMCAYPGCNK (SEQ ID NO:195), FMCAYPGCN (SEQ ID NO:196), FMCAYPGCY (SEQ ID NO:197), or FMCAYPGCK (SEQ ID NO:198).

Each peptide of a combination may be administered separately within its own formulation, or two, three, four, five, or more peptides of a combination may be administered together within the same formulation.

The dose level or each peptide, the frequency of administration of each or combinations of peptides, the duration of administration and other aspects of the immunization with WT1 peptides may be optimized in accordance with the patient's clinical presentation, duration or course of the disease, comorbidities, and other aspects of clinical care. The invention is not so limiting with regard to the particular aspects of the immunization component of the methods embodied herein.

In one embodiment, the WT-1 vaccine comprises 280 mcg of each of the four aforementioned peptides (YMFPNAPYL (SEQ ID NO:124), RSDELVRHHNMHQRNMTKL (SEQ ID NO:1), PGCNKRYFKLSHLQMHSRKHTG (SEQ ID NO: 2) and SGQAYMFPNAPYLPSCLES (SEQ ID NO:125)) combined in a total volume of 0.7 ml (0.4 mg/ml of each peptide). In one embodiment, 200 mcg of each peptide is administered at each dose (0.5 ml). In one embodiment 100 to 2000 mcg of each peptide is administered at each dose. In one embodiment, the foregoing dose is administered every other week over a course of 10 weeks (i.e., 6 administrations). In one embodiment, administration is subcutaneous. In one embodiment, an adjuvant is mixed (emulsified) with the vaccine before dosing. In one embodiment 0.5 mL of vaccine (i.e., 200 mcg of each peptide) is emulsified with 1.0 mL of adjuvant before administration. In another embodiment, the adjuvant is injected at the same site as the vaccine, before or after the vaccine is injected. In one embodiment, the adjuvant is an emulsion. In one embodiment, the emulsion is a Montanide emulsion. In one embodiment, the Montanide emulsion is the immunologic adjuvant Montanide ISA 51 VG. In the practice of the invention, a checkpoint inhibitor is also administered to the subject with the WT1 vaccine, as described further below.

As noted above, the one or more WT1 peptides may be administered as an immunogenic composition to elicit an immune response against a WT1 expressing cancer, or in another embodiment, the one or more WT1 peptides may be used to prepare WT1-specific CTLs using in vitro or ex vivo methods, said CTLs upon administration to the patient will be directed against a WT1 expressing cancer. In one embodiment, one or more WT1 peptides are used to induce the production of CTLs in vitro, using cells from a cell line, for example. In another embodiment, the one or more WT1 peptides are used to induce the production of CTLs in a sample of cells taken from the patient, wherein the CTLs induced ex vivo are infused back into the same patient in need thereof. In another embodiment, the one or more WT1 peptides are used to induce the production of CTLs in a sample of cells taken from a donor, wherein the CTLs induced ex vivo are infused into a patient in need thereof who is not the donor. In another embodiment, a subject who is not the patient in need of therapy, is administered the one or more WT1 peptides described here in order to induce the formation of CTLs, which are then transferred from the donor to the patient. Each of these embodiments are other aspects of the invention, and sources of WT1 specific cells useful in treating cancer or reducing the incidence of cancer or its relapse as described herein.

In all of the foregoing methods, whether vaccination of the patient to induce a CTL response against a WT1 expressing cancer, or obtaining WT1 specific CTLs from a donor, from an in vitro or ex vivo method using immune cells from a cell line, the patient, or a donor who is not the patient, the combined use of a checkpoint inhibitor is embodied herein, whether the methods for treating, reducing the incidence of cancer or its relapse is by immunizing the subject in need thereof with one or more WT1 peptides, or producing CTLs in vitro ex vivo or in a donor subject. In all of these methods, the combined use of one or more checkpoint inhibitors is embodied herein. The one or more checkpoint inhibitor may be administered to the patient that is being immunized with the one or more WT1 peptides. The checkpoint inhibitor may be used in vitro or ex vivo to enhance the formation of WT1 specific CTLs that are subsequently infused into the patient. The one or more checkpoint inhibitors may be used in the donor subject to enhance the formation of WT1 specific CTLs that will then be transferred into the patient. The checkpoint inhibitor may be used in the patient receiving CTLs prepared in vitro, ex vivo, or in a donor, whether or not the in vitro, ex vivo, or donor was also administered a checkpoint inhibitor. In the latter embodiments, the same or different one or more checkpoint inhibitors may be used in the in vitro, ex vivo or donor subject, and in the patient.

Immune checkpoints regulate T cell function in the immune system. T cells play a central role in cell-mediated immunity. Checkpoint proteins interact with specific ligands which send a signal into the T cell and essentially switch off or inhibit T cell function. Cancer cells take advantage of this system by driving high levels of expression of checkpoint proteins on their surface which results in control of the T cells expressing checkpoint proteins on the surface of T cells that enter the tumor microenvironment, thus suppressing the anticancer immune response. As such, inhibition of checkpoint proteins would result in restoration of T cell function and an immune response to the cancer cells. An immune checkpoint inhibitor (or checkpoint inhibitor) is a compound or agent that blocks or inhibits immune checkpoint proteins (i.e., that blocks or inhibits checkpoint receptors or checkpoint receptor ligands). Examples of checkpoint proteins include, but are not limited to, CTLA-4, PD-L1, PD-L2, PD1, B7-H3, B7-H4, BTLA, HVEM, TIM3, GAL9, LAG3, VISTA, IDO, KIR, 2B4 (belongs to the CD2 family of molecules and is expressed on all NK cells, and memory $CD8^+$ T cells), CD160 (also referred to as BY55), CGEN- 15049, CHK 1 and CHK2 kinases, A2aR, and various B-7 family ligands. Programmed Death-1 (PD-1) is a member of the immunoglobulin superfamily (IGSF) of molecules involved in regulation of T cell activation. PD-1 acquired its name 'programmed death' when it was identified in 1992 as a gene upregulated in T cell hybridoma undergoing cell death. The structure of PD-1 is composed of one IGSF domain, a transmembrane domain, and an intracellular domain containing an immunoreceptor tyrosine-based inhibitory motif (ITIM) and an immunoreceptor tyrosine-based switch motif (ITSM) [38]. PD-1 has two binding partners: PD-L1 (B7-H1, CD274) and PD-L2 (B7-DC, CD273). PD-L1 is expressed broadly on both hematopoietic and non-hematopoietic lineages [39, 40]. It is found on T cell, B cells, macrophages, NK cells, DCs, and mast cells as well as in peripheral tissues. [41, 42]. PD-1 engagement represents one means by which tumors evade immunosurveillance and clearance [43]. Blockade of the PD-1 pathway has been demonstrated by nivolumab, which shows activity in immunocompetent mouse cancer models [44].

Non-limiting examples of checkpoint inhibitors include small molecules, peptides, and antibodies. Non-limiting examples of antibodies include nivolumab (OPDIVO), pembrolizumab (KEYTRUDA), pidilizumab (CT-011), MEDI0680 (AMP-514), AMP-224, AUNP-12, BMS 936559, atezolizumab (MPDL3280A), durvalumab (MEDI4736), avelumab (MSB0010718C), BMS935559 (MDX-1105), rHIgM12B7, BMS-986016, GSK2831781, IMP321, lirilumab (BMS-986015), IPH2101 (1-7F9), Indoximod (NLG 9189), NLG 919, INCB024360, PF-05082566, Urelumab (BMS-663513), and MEDI6469.

Nivolumab (OPDIVO) is a fully human IgG4 monoclonal antibody targeted against PD-1 receptor on activated T and B lymphocytes[47]. Pembrolizumab (KEYTRUDA) is another non-limiting example of an antibody that targets PD-1. Other compounds and agents that block, inhibit or target checkpoint proteins include compounds undergoing testing and not yet available on the market. The invention is not limited by the specific checkpoint inhibitor. Non-limiting examples of checkpoint inhibitors that may be used are listed in Table 1.

TABLE 1

Examples of Checkpoint Inhibitors

| Name | Class of Agent | Target |
|---|---|---|
| Ipilumumab (a.k.a. MDX-010; MDX-101; BMS-734016; marketed as Yervoy) | IgG1 human mAb | Cytotoxic T-lymphocyte antigen 4 (CTLA-4) |
| Tremelimumab (a.k.a. ticilimumab; CP-675-206) | IgG2 human mAb | CTLA-4 |
| Nivolumab (a.k.a. ONO-4538; BMS-936558; MDX1106; marketed as Opdivo) | IgG4 human mAb | Programmed death-1 (PD-1) |
| Pembrolizumab (a.k.a., MK-3475; lambrolizumab; marketed as Keytruda) | IgG4 humanized mAb | PD-1 |
| Pidlizumab (a.k.a. CT-011) | IgG1 humanized mAb | PD-1 |
| MEDI0680 (a.k.a. AMP-514) | IgG4 humanized mAb | PD-1 |
| AMP-224 | Fc-PD-L2 fusion Protein | PD-1 |
| AUNP-12 | Branched, 29-amino acid peptide | PD-1 |
| BMS-936559 | IgG4 human mAb | Programmed death ligand-1 (PD-L1) |
| Atezolizumab (a.k.a. MPDL3280A; RG7446) | IgG1 humanized mAb | PD-L1 |
| Durvalumab (a.k.a. MEDI4736) | IgG1 human mAb | PD-L1 |
| Avelumab (a.k.a. MSB0010718C) | IgG1 human mAb | PD-L1 |
| BMS935559 (a.k.a. MDX-1105) | IgG4 human mAb | PD-L1 |
| rHIgM12B7 | IgM human mAb | Programmed death ligand-2 (PD-L2) |
| BMS-986016 | mAB | Lymphocyte activation gene-3 (LAG-3; a.k.a. CD223) |
| GSK2831781 | Humanized afuscated mAb | LAG-3 |
| IMP321 | Soluble LAG-3 | LAG-3 |
| Lirilumab (a.k.a. BMS-986015) | IgG4 human mAb | Killer cell immunoglobulin-like receptor (KIR) |
| IPH2101 (a.k.a. 1-7F9) | Anti-inhibitor monoclonal Ab | KIR |
| Indoximod (a.k.a. NLG 9189; CAS # 110117-83-4) | Small molecule (D isomer of 1-methyl-tryptophan) | Indoleamine-2,3-dioxygenase 1 (IDO1) |
| NLG 919 (CAS # 1402836-58-1) | Small molecule | IDO1 |
| INCB024360 (CAS # 914471-09-3) | Small molecule | IDO1 |
| PF-05082566 | IgG2 human mAB | 4-1BB (a.k.a. CD137) |
| Urelumab (a.k.a. BMS-663513) | IgG4 humanized mAb | 4-1BB |
| MEDI6469 | IgG1 mouse anti-human Ab | OX40 (a.k.a. CD134) |

In one embodiment, a combination of two or more checkpoint inhibitors is administered to the subject. In one embodiment, the combination of checkpoint inhibitors is selected from among those in Table 1. The two or more checkpoint inhibitors can be administered simultaneously or consecutively with respect to one another and with respect to the one or more WT1 peptides. In a further embodiment, the combination of two or more checkpoint inhibitors target two different checkpoint proteins, such as PD-1 (e.g., nivolumab or other PD-1 inhibitor) and CTLA-4 (e.g., ipilumumab or other CTLA-4 inhibitor), are administered to the subject simultaneously or consecutively with respect to one another and with respect to the one or more WT1 peptides. In one embodiment, the combination of two or more checkpoint inhibitors target two or more different checkpoint proteins from among: CTLA-4, PD-L1, PD-L2, PD1, B7-H3, B7-H4, BTLA, HVEM, TIM3, GAL9, LAG3, VISTA, KIR, 2B4, CD160, CGEN-15049, CHK 1 kinase, CHK2 kinase, A2aR, and B-7 family ligands. In one embodiment, the combination of two or more checkpoint inhibitors targeting two or more different checkpoint proteins is selected from among those in Table 1.

The dose level, frequency of dosing, duration of dosing and other aspects of administration of the checkpoint inhibitor may be optimized in accordance with the patient's clinical presentation, duration or course of the disease, comorbidities, and other aspects of clinical care. The invention is not so limiting with regard to the particular aspects of the checkpoint inhibitor component of the methods embodied herein.

In one embodiment, a nivolumab dose and schedule selection of 3 mg/kg every 2 weeks over a course of 12 weeks. In one embodiment, administration is intravenous. In one embodiment, the course of checkpoint inhibitor administration is concurrent with that of the WT1 vaccine administration. In one embodiment the course of checkpoint inhibitor administration overlaps with that of the WT1 vaccine administration. In one embodiment the course of checkpoint inhibitor administration starts at about the same time as the course of the WT1 vaccine administration.

In one embodiment, the WT1 vaccine comprises 200 mcg of each of the peptides YMFPNAPYL (SEQ ID NO:124), RSDELVRHHNMHQRNMTKL (SEQ ID NO:1), PGCNKRYFKLSHLQMHSRKHTG (SEQ ID NO: 2) and SGQAYMFPNAPYLPSCLES (SEQ ID NO:125) combined in a total volume of 0.5 ml emulsified with 1.0 mL Montanide ISA 51 VG and administered subcutaneously every 2 weeks for 6 administrations; and nivolumab, 3 mg/kg, is administered intravenously by 60 minute infusion every two weeks for 7 administrations, starting at the same time as the WT1 vaccine.

In one embodiment, methods are embodied herein in which the one or more WT1 peptide and the one or more checkpoint inhibitor are each administered to a subject according to a schedule that maximally benefits the patient. The one or more WT1 peptide and the one or more checkpoint inhibitor are therefore not necessarily administered at the same time or even in the same composition or each for the same duration. Each WT1 peptide may be administered in accordance with a particular schedule, as may be each checkpoint inhibitor. In one non-limiting embodiment, the one or more WT1 peptide and one or more the checkpoint inhibitor are present in the same composition.

As noted herein, the dose level and dosing schedule including frequency and duration of the WT1 peptide or peptides (separately or administered together) and that of the one or more checkpoint inhibitors (administered separately or together), the route of administration, and other aspects of administration are optimized for maximal benefit to the patient subject. These same aspects are also considered when a donor subject is the recipient of the WT1 peptide or peptides and the checkpoint inhibitor or inhibitors for the purpose of generating WT1 specific CTLs to administer to the patient.

In one embodiment, compositions are provided containing at least one WT1 peptide and at least one checkpoint inhibitor. In one embodiment, the WT1 peptide or peptides in the composition are among those disclosed herein. In one embodiment, the checkpoint inhibitor is among those disclosed herein. In one embodiment, the composition comprises one, two, three peptides from among WT1 peptides YMFPNAPYL (SEQ ID NO:124), RSDELVRHHNMHQRNMTKL (SEQ ID NO:1), PGCNKRYFKLSHLQMHSRKHTG (SEQ ID NO: 2) and SGQAYMFPNAPYLPSCLES (SEQ ID NO:125). In one embodiment the composition comprises YMFPNAPYL (SEQ ID NO:124), RSDELVRHHNMHQRNMTKL (SEQ ID NO:1), PGCNKRYFKLSHLQMHSRKHTG (SEQ ID NO: 2) and SGQAYMFPNAPYLPSCLES (SEQ ID NO:125). In one embodiment the composition comprises the checkpoint inhibitor nivolumab, pembrolizumab, or the combination thereof. The composition may further comprise an excipient, diluent or carrier. The composition may also comprise one or more adjuvants.

The foregoing embodiments provide improved methods of treating, reducing the incidence of, and inducing immune responses against a WT1-expressing cancer, and compositions useful for the same purposes. Other aspects of the invention are described further below.

In one embodiment, a modified WT1 peptide has one or more altered amino acids, referred to herein as a mutated WT1 peptide. In one embodiment the mutated WT1 peptide comprise: (a) a binding motif of a human leukocyte antigen (HLA) Class II molecule; and (b) a binding motif of an HLA class I molecule comprising a point mutation in one or more anchor residues of the binding motif of an HLA class I molecule. In another embodiment, the peptide is 11 or more amino acids in length.

In certain other embodiments, the peptide is 11-22, 11-30, 16-22 or 16-30 amino acids in length. In another embodiment, the point mutation is in 1-3 anchor residues of the HLA class I molecule binding motif. In another embodiment, the point mutation is in 1 anchor residue of the HLA class I molecule binding motif. In another embodiment, the point mutation is in 2 anchor residues of the HLA class I molecule binding motif. In another embodiment, the point mutation is in 1-2 anchor residues of the HLA class I molecule binding motif. In another embodiment, the point mutation is in 2-3 anchor residues of the HLA class I molecule binding motif. In another embodiment, the point mutation is in 1-4 anchor residues of the HLA class I molecule binding motif. Each possibility represents a separate embodiment of the present invention.

In another embodiment, the present invention provides a method of treating a subject with a WT1-expressing cancer, the method comprising administering to the subject at least one WT1 peptide and at least one checkpoint inhibitor, thereby treating a subject with a WT1-expressing cancer.

In another embodiment, the present invention provides a method of reducing the incidence of a WT1-expressing cancer, or its relapse, in a subject, the method comprising administering to the subject at least one WT1 peptide and at least one checkpoint inhibitor, thereby reducing the incidence of a WT1-expressing cancer, or its relapse, in a subject.

In another embodiment, the present invention provides a method of inducing formation and proliferation of a WT1 protein-specific CTL, the method comprising contacting a lymphocyte population with at least one WT1 peptide and at least one checkpoint inhibitor, thereby inducing formation and proliferation of a WT1 protein-specific CTL.

In another embodiment, the present invention provides a method of inducing formation and proliferation of (a) a WT1 protein-specific CD8$^+$ lymphocyte; and (b) a CD4$^+$ lymphocyte specific for the WT1 protein, the method comprising contacting a lymphocyte population with at least one WT1 peptide and at least one checkpoint inhibitor, thereby inducing formation and proliferation of (a) a WT1 protein-specific CD8$^+$ lymphocyte; and (b) a CD4$^+$ lymphocyte specific for the WT1 protein.

In one embodiment, the aforementioned methods for treating a WT1 expressing cancer, reducing the incidence of a WT1 expressing cancer or inducing the formation and proliferation of a WT1 protein specific T cell response, are achieved with greater effect than if such methods employ only the WT1 peptide(s) alone or the checkpoint inhibitor(s) alone. In one embodiment, the course of administration of the WT1 vaccine and the course of administration of the one or more checkpoint inhibitors are concurrent, overlap, or are contemporaneous such that the biological response to the vaccine is enhanced by the administration of the one or more checkpoint inhibitors. Contemporaneous administration embraces a course of WT1 vaccination to induce WT1 specific CTLs, and administration of the one or more checkpoint inhibitor to enhance the activity of the CTLs against the cancer. In one embodiment, the course of WT1 vaccine administration can end before the course of checkpoint inhibitor therapy begins, insofar as the effectiveness of the CTLs elicited by the WT1 vaccine administration is enhanced by the checkpoint inhibitor therapy. In one embodiment, the first administration of checkpoint inhibitor therapy is on the same day as the last WT1 vaccine administration. In one embodiment the end of WT1 vaccination and the start of checkpoint inhibitor therapy is separated by from 1-7 days or from 1-4 weeks.

As noted herein, the WT1 peptide(s) may be native fragments, or contiguous amino acid sequences, of the WT1 protein, or they may have one or more modifications of the amino acid sequence to enhance immunogenicity or any other beneficial property to the peptide and the development of immunity to a WT1 expressing cancer. In certain embodiments, one or amino acids are changed to enhance immunogenicity. In one embodiment, the methods of use employ an isolated, mutated WT1 peptide, comprising: (a) a binding motif of a human leukocyte antigen (HLA) Class II molecule; and (b) a binding motif of an HLA class I molecule, having a point mutation in 1 or more anchor residues of the binding motif of an HLA class I molecule. In another embodiment, the peptide is 11 or more aa in length. Each possibility represents a separate embodiment of the present invention.

The "point mutation," in another embodiment, indicates that the fragment is mutated with respect to the native sequence of the protein, thus creating the HLA class I molecule binding motif. In another embodiment, the "point mutation" strengthens the binding capacity of an HLA class I molecule binding motif present in the native sequence. Each possibility represents a separate embodiment of the methods of use of present invention.

In another embodiment, the point mutation is in 1-3 anchor residues of the HLA class I molecule binding motif. In another embodiment, the point mutation is in 1 anchor residue of the HLA class I molecule binding motif. In another embodiment, the point mutation is in 2 anchor residues of the HLA class I molecule binding motif. In another embodiment, the point mutation is in 1-2 anchor residues of the HLA class I molecule binding motif. In another embodiment, the point mutation is in 2-3 anchor residues of the HLA class I molecule binding motif. In another embodiment, the point mutation is in 1-4 anchor residues of the HLA class I molecule binding motif. Each possibility represents a separate embodiment of the present invention.

In another embodiment, a peptide of the present invention is 11-453 amino acids (AA) in length. In another embodiment, the length is 12-453 AA. In another embodiment, the length is 13-453 AA. In another embodiment, the length is 14-453 AA. In another embodiment, the length is 15-453 AA. In another embodiment, the length is 16-453 AA. In another embodiment, the length is 17-453 AA. In another embodiment, the length is 18-453 AA. In another embodiment, the length is 19-453 AA. In another embodiment, the length is 20-453 AA.

In another embodiment, the length is 11-449 AA. In another embodiment, the length is 12-449 AA. In another embodiment, the length is 13-449 AA. In another embodiment, the length is 14-449 AA. In another embodiment, the length is 15-449 AA. In another embodiment, the length is 16-449 AA. In another embodiment, the length is 17-449 AA. In another embodiment, the length is 18-449 AA. In another embodiment, the length is 19-449 AA. In another embodiment, the length is 20-449 AA.

In another embodiment, the length is 11-30 AA. In another embodiment, the length is 16-22 AA. In another embodiment, the length is 19 AA. In another embodiment, the peptide is 15-23 AA in length. In another embodiment, the length is 15-24 AA. In another embodiment, the length is 15-25 AA. In another embodiment, the length is 15-26 AA. In another embodiment, the length is 15-27 AA. In another embodiment, the length is 15-28 AA. In another embodiment, the length is 14-30 AA. In another embodiment, the length is 14-29 AA. In another embodiment, the length is 14-28 AA. In another embodiment, the length is 14-26 AA. In another embodiment, the length is 14-24 AA. In another embodiment, the length is 14-22 AA. In another embodiment, the length is 14-20 AA. In another embodiment, the length is 16-30 AA. In another embodiment, the length is 16-28 AA. In another embodiment, the length is 16-26 AA. In another embodiment, the length is 16-24 AA. In another embodiment, the length is 16-22 AA. In another embodiment, the length is 18-30 AA. In another embodiment, the length is 18-28 AA. In another embodiment, the length is 18-26 AA. In another embodiment, the length is 18-24 AA. In another embodiment, the length is 18-22 AA. In another embodiment, the length is 18-20 AA. In another embodiment, the length is 20-30 AA. In another embodiment, the length is 20-28 AA. In another embodiment, the length is 20-26 AA. In another embodiment, the length is 20-24 AA. In another embodiment, the length is 22-30 AA. In another embodiment, the length is 22-28 AA. In another embodiment, the length is 22-26 AA. In another embodiment, the length is 24-30 AA. In another embodiment, the length is 24-28 AA. In another embodiment, the length is 24-26 AA.

In another embodiment, a peptide useful for the methods and compositions of the present invention is longer than the minimum length for binding to an HLA class II molecule, which is, in another embodiment, about 12 AA. In another embodiment, increasing the length of the HLA class II-binding peptide enables binding to more than one HLA class II molecule. In another embodiment, increasing the length enables binding to an HLA class II molecule whose binding motif is not known. In another embodiment, increasing the length enables binding to an HLA class I molecule. In another embodiment, the binding motif of the HLA class I molecule is known. In another embodiment, the binding motif of the HLA class I molecule is not known. Each possibility represents a separate embodiment of the present invention.

Each of the above peptide lengths represents a separate embodiment of the present invention.

HLA molecules, known in another embodiment as major histocompatibility complex (MHC) molecules, bind peptides and present them to immune cells. Thus, in another embodiment, the immunogenicity of a peptide is partially determined by its affinity for HLA molecules. HLA class I molecules interact with CD8 molecules, which are generally present on cytotoxic T lymphocytes (CTL). HLA class II molecules interact with CD4 molecules, which are generally present on helper T lymphocytes.

In another embodiment, a peptide of the present invention is immunogenic. In another embodiment, the term "immunogenic" refers to an ability to stimulate, elicit or participate in an immune response. In another embodiment, the immune response elicited is a cell-mediated immune response. In another embodiment, the immune response is a combination of cell-mediated and humoral responses.

In another embodiment, T cells that bind to the HLA molecule-peptide complex become activated and induced to proliferate and lyse cells expressing a protein comprising the peptide. T cells are typically initially activated by "professional" antigen presenting cells ("APC"; e.g. dendritic cells, monocytes, and macrophages), which present costimulatory molecules that encourage T cell activation rather than anergy or apoptosis. In another embodiment, the response is heteroclitic, as described herein, such that the CTL lyses a neoplastic cell expressing a protein which has an AA sequence homologous to a peptide of this invention, or a different peptide than that used to first stimulate the T cell.

In another embodiment, an encounter of a T cell with a peptide of this invention induces its differentiation into an effector and/or memory T cell. Subsequent encounters between the effector or memory T cell and the same peptide, or, in another embodiment, with a heteroclitic peptide of this invention, leads to a faster and more intense immune response. Such responses are gauged, in another embodiment, by measuring the degree of proliferation of the T cell population exposed to the peptide. In another embodiment, such responses are gauged by any of the methods enumerated herein below.

In another embodiment, as described herein, the subject is exposed to a peptide, or a composition/cell population comprising a peptide of this invention, which differs from the native protein expressed, wherein subsequently a host immune response cross-reactive with the native protein/antigen develops.

In another embodiment, peptides, compositions, and vaccines of this invention stimulate an immune response that results in tumor cell lysis. In all of the foregoing embodiments, the concurrent use of a checkpoint inhibitor enhances the immune response against the tumor.

In another embodiment, the HLA class I molecule binding motif of a peptide of the present invention is contained within the HLA class II molecule binding motif of the peptide. In another embodiment, the HLA class I molecule binding motif overlaps with the HLA class II molecule binding motif. In another embodiment, the HLA class I molecule binding motif does not overlap with the HLA class II molecule binding motif. Each possibility represents a separate embodiment of the present invention.

The HLA class II molecule whose binding motif is contained in a peptide of the present invention is, in another embodiment, an HLA-DR molecule. In another embodiment, the HLA class II molecule is an HLA-DP molecule. In another embodiment, the HLA class II molecule is an HLA-DQ molecule.

In another embodiment, the HLA class II molecule is an HLA-DRB molecule. In another embodiment, the HLA class II molecule is DRB101. In another embodiment, the HLA class II molecule is DRB301. In another embodiment, the HLA class II molecule is DRB401. In another embodiment, the HLA class II molecule is DRB701. In another embodiment, the HLA class II molecule is DRB1101. In another embodiment, the HLA class II molecule is DRB1501. In another embodiment, the HLA class II molecule is any other HLA-DRB molecule known in the art. In another embodiment, the HLA class II molecule is an HLA-DRA molecule. In another embodiment, the HLA class II molecule is an HLA-DQA1 molecule. In another embodiment, the HLA class II molecule is an HLA-DQB1 molecule. In another embodiment, the HLA class II molecule is an HLA-DPA1 molecule. In another embodiment, the HLA class II molecule is an HLA-DPB1 molecule. In another embodiment, the HLA class II molecule is an HLA-DMA molecule. In another embodiment, the HLA class II molecule is an HLA-DMB molecule. In another embodiment, the HLA class II molecule is an HLA-DOA molecule. In another embodiment, the HLA class II molecule is an HLA-DOB molecule. In another embodiment, the HLA class II molecule is any other HLA class II-molecule known in the art.

In another embodiment, a peptide of the present invention binds to 2 distinct HLA class II molecules. In another embodiment, the peptide binds to three distinct HLA class II molecules. In another embodiment, the peptide binds to four distinct HLA class II molecules. In another embodiment, the peptide binds to five distinct HLA class II molecules. In another embodiment, the peptide binds to six distinct HLA class II molecules. In another embodiment, the peptide binds to more than six distinct HLA class II molecules.

In another embodiment, the HLA class II molecules that are bound by a peptide of the present invention are encoded by two or more distinct alleles at a given HLA class II locus. In another embodiment, the HLA class II molecules are encoded by three distinct alleles at a locus. In another embodiment, the HLA class II molecules are encoded by four distinct alleles at a locus. In another embodiment, the HLA class II molecules are encoded by five distinct alleles at a locus. In another embodiment, the HLA class II molecules are encoded by six distinct alleles at a locus. In another embodiment, the HLA class II molecules are encoded by more than six distinct alleles at a locus.

In another embodiment, the HLA class II molecules bound by the peptide are encoded by HLA class II genes at two distinct loci. In another embodiment, the HLA class II molecules are encoded by HLA class II genes at 2 or more distinct loci. In another embodiment, the HLA class II molecules are encoded by HLA class II genes at 3 distinct loci. In another embodiment, the HLA class II molecules are encoded by HLA class II genes at 3 or more distinct loci. In another embodiment, the HLA class II molecules are encoded by HLA class II genes at 4 distinct loci. In another embodiment, the HLA class II molecules are encoded by HLA class II genes at 4 or more distinct loci. In another embodiment, the HLA class II molecules are encoded by HLA class II genes at 5 distinct loci. In another embodiment, the HLA class II molecules are encoded by HLA class II genes at 5 or more distinct loci. In another embodiment, the HLA class II molecules are encoded by HLA class II genes at 6 distinct loci. In another embodiment, the HLA class II molecules are encoded by HLA class II genes at 6 or more distinct loci. In another embodiment, the HLA class II molecules are encoded by HLA class II genes at more than 6 distinct loci. Each possibility represents a separate embodiment of the present invention.

In another embodiment, a peptide of the present invention binds to 2 distinct HLA-DRB molecules. In another embodiment, the peptide binds to three distinct HLA-DRB molecules. In another embodiment, the peptide binds to four distinct HLA-DRB molecules. In another embodiment, the peptide binds to five distinct HLA-DRB molecules. In another embodiment, the peptide binds to six distinct HLA-DRB molecules. In another embodiment, the peptide binds to more than six distinct HLA-DRB molecules.

In another embodiment, the HLA class II molecules bound by the WT1 peptide are encoded by HLA class II genes at 2 distinct loci. In another embodiment, the HLA molecules bound are encoded by HLA class II genes at 2 or more distinct loci. In another embodiment, the HLA molecules bound are encoded by HLA class II genes at 3 distinct loci. In another embodiment, the HLA molecules bound are encoded by HLA class II genes at 3 or more distinct loci. In another embodiment, the HLA molecules bound are encoded by HLA class II genes at 4 distinct loci. In another embodiment, the HLA molecules bound are encoded by HLA class II genes at 4 or more distinct loci. In another embodiment, the HLA molecules bound are encoded by HLA class II genes at more than 4 distinct loci. In other embodiments, the loci are selected from HLA-DRB loci. In another embodiment, the HLA class II-binding peptide is an HLA-DRA binding peptide. In another embodiment, the peptide is an HLA-DQA1 binding peptide. In another embodiment, the peptide is an HLA-DQB1 binding peptide. In another embodiment, the peptide is an HLA-DPA1 binding peptide. In another embodiment, the peptide is an HLA-DPB1 binding peptide. In another embodiment, the peptide is an HLA-DMA binding peptide. In another embodiment, the peptide is an HLA-DMB binding peptide. In another embodiment, the peptide is an HLA-DOA binding peptide. In another embodiment, the peptide is an HLA-DOB binding peptide. In another embodiment, the peptide binds to any other HLA class II molecule known in the art. Each possibility represents a separate embodiment of the present invention.

In another embodiment, a peptide of the present invention binds to HLA-DRB molecules that are encoded by 2 distinct HLA-DRB alleles selected from DRB101, DRB301, DRB401, DRB701, DRB1101, and DRB1501. In another embodiment, the peptide binds to HLA-DRB molecules encoded by 3 distinct HLA-DRB alleles selected from DRB101, DRB301, DRB401, DRB701, DRB 1101, and DRB1501. In another embodiment, the peptide binds to HLA-DRB molecules encoded by 4 distinct HLA-DRB alleles selected from DRB101, DRB301, DRB401, DRB701, DRB1101, and DRB1501. In another embodiment, the peptide binds to HLA-DRB molecules encoded by 5 distinct HLA-DRB alleles selected from DRB101, DRB301, DRB401, DRB701, DRB1101, and DRB 1501. In another embodiment, the peptide binds to HLA-DRB molecules encoded by each of the following HLA-DRB alleles: DRB101, DRB301, DRB401, DRB701, DRB1101, and DRB1501. Each possibility represents a separate embodiment of the present invention.

Each of the above HLA class II molecule, types, classes, and combinations thereof represents a separate embodiment of the present invention.

The HLA class I molecule whose binding motif is contained in a peptide of the present invention is, in another embodiment, an HLA-A molecule. In another embodiment, the HLA class I molecule is an HLA-B molecule. In another embodiment, the HLA class I molecule is an HLA-C molecule. In another embodiment, the HLA class I molecule is an HLA-A0201 molecule. In another embodiment, the molecule is HLA A1. In another embodiment, the HLA class I molecule is HLA A2. In another embodiment, the HLA class I molecule is HLA A2.1. In another embodiment, the HLA class I molecule is HLA A3. In another embodiment, the HLA class I molecule is HLA A3.2. In another embodiment, the HLA class I molecule is HLA A11. In another embodiment, the HLA class I molecule is HLA A24. In another embodiment, the HLA class I molecule is HLA B7. In another embodiment, the HLA class I molecule is HLA B27. In another embodiment, the HLA class I molecule is HLA B8. Each possibility represents a separate embodiment of the present invention.

In another embodiment, the HLA class I molecule-binding WT1 peptide of methods and compositions of the present invention binds to a superfamily of HLA class I molecules. In another embodiment, the superfamily is the A2 superfamily. In another embodiment, the superfamily is the A3 superfamily. In another embodiment, the superfamily is the A24 superfamily. In another embodiment, the superfamily is the B7 superfamily. In another embodiment, the superfamily is the B27 superfamily. In another embodiment, the superfamily is the B44 superfamily. In another embodiment, the superfamily is the C1 superfamily. In another embodiment, the superfamily is the C4 superfamily. In another embodiment, the superfamily is any other superfamily known in the art. Each possibility represents a separate embodiment of the present invention.

In another embodiment, an HLA class I molecule binding motif of a peptide of the present invention exhibits an increased affinity for the HLA class I molecule, relative to the unmutated counterpart of the peptide. In another embodiment, the point mutation increases the affinity of the isolated, mutated WT1 peptide for the HLA class I molecule. In another embodiment, the increase in affinity is relative to the affinity (for the same HLA class I molecule) of the isolated, unmutated WT1 peptide wherefrom the isolated, mutated WT1 peptide was derived. Each possibility represents a separate embodiment of the present invention.

In another embodiment, an HLA class I molecule-binding WT peptide of methods and compositions of the present invention has a length of 9-13 AA. In another embodiment, the length is 8-13 AA. In another embodiment, the peptide has any of the lengths of a peptide of the present invention enumerated herein.

In another embodiment, the HLA class I molecule-binding WT peptide has length of 8 AA. In another embodiment, the peptide has length of 9 AA. In another embodiment, the peptide has length of 10 AA. As provided herein, native and heteroclitic peptides of 9-10 AA exhibited substantial binding to HLA class I molecules and ability to elicit cytokine secretion and cytolysis by CTL.

In another embodiment, an HLA class I molecule-binding WT1 peptide embedded within a WT1 peptide of the present invention has 1 of the above lengths. Each possibility represents a separate embodiment of the present invention. In one embodiment, the WT1 peptide is a peptide of longer length than an HLA class I molecule-binding WT1 peptide.

The longer length peptide is degraded by cells to the appropriate length to be presented by a HLA class 1 molecule.

In another embodiment, the HLA class I molecule that is bound by the HLA class I molecule-binding WT1 peptide is an HLA-A molecule. In another embodiment, the HLA class I-molecule is an HLA-A2 molecule. In another embodiment, the HLA class I-molecule is an HLA-A3 molecule. In another embodiment, the HLA class I-molecule is an HLA-A11 molecule. In another embodiment, the HLA class I-molecule is an HLA-B8 molecule. In another embodiment, the HLA class I-molecule is an HLA-0201 molecule. In another embodiment, the HLA class I-molecule binds any other HLA class I molecule known in the art. Each possibility represents a separate embodiment of the present invention.

In another embodiment, a peptide of the present invention retains ability to bind multiple HLA class II molecules, as exhibited by the isolated WT1 peptide wherefrom the peptide of the present invention was derived.

In all of the aspects herein, the one or more WT1 peptides useful in the vaccine herein or for generating CTLs in vitro, ex vivo or in a donor, the selection of the peptide or peptides sequences, whether native or modified, to match the HLA type(s) of the patient or donor is embodied herein.

The WT1 molecule from which a peptide of the present invention is derived has, in another embodiment, the sequence:

MGSDVRDLNALLPAVPSLGGGGGCALPVSGAAQWAPVLDFAPPGASAYGS
LGGPAPPPAPPPPPPPPHSFIKQEPSWGGAEPHEEQCLSAFTVHFSGQF
TGTAGACRYGPFGPPPPSQASSGQARMFPNAPYLPSCLESQPAIRNQGYS
TVTFDGTPSYGHTPSHHAAQFPNHSFKHEDPMGQQGSLGEQQYSVPPPVY
GCHTPTDSCTGSQALLLRTPYSSDNLYQMTSQLECMTWNQMNLGATLKGV
AAGSSSSVKWTEGQSNHSTGYESDNHTTPILCGAQYRIHTHGVFRGIQDV
RRVPGVAPTLVRSASETSEKRPFMCAYPGCNKRYFKLSHLQMHSRKHTGE
KPYQCDFKDCERRFSRSDQLKRHQRRHTGVKPFQCKTCQRKFSRSDHLKT
HTRTHTGKTSEKPFSCRWPSCQKKFARSDELVRHHNMHQRNMTKLQLAL (SEQ ID NO: 199; GenBank Accession number

AY245105).

In another embodiment, the WT1 molecule has the sequence:

AAEASAERLQGRRSRGASGSEPQQMGSDVRDLNALLPAVPSLGGGGCAL
PVSGAAQWAPVLDFAPPGASAYGSLGGPAPPPAPPPPPPPPHSFIKQEP
SWGGAEPHEEQCLSAFTVHFSGQFTGTAGACRYGPFGPPPPSQASSGQAR
MFPNAPYLPSCLESQPAIRNQGYSTVTFDGTPSYGHTPSHHAAQFPNHSF
KHEDPMGQQGSLGEQQYSVPPPVYGCHTPTDSCTGSQALLLRTPYSSDNL
YQMTSQLECMTWNQMNLGATLKGHSTGYESDNHTTPILCGAQYRIHTHGV
FRGIQDVRRVPGVAPTLVRSASETSEKRPFMCAYPGCNKRYFKLSHLQMH
SRKHTGEKPYQCDFKDCERRFSRSDQLKRHQRRHTGVKPFQCKTCQRKFS
RSDHLKTHTRTHTGEKPFSCRWPSCQKKFARSDELVRHHNMHQRNMTKLQ
LAL (SEQ ID NO: 200; GenBank Accession number

NM_000378).

In another embodiment, the WT1 molecule has the sequence:

MQDPASTCVPEPASQHTLRSGPGCLQQPEQQGVRDPGGIWAKLGAAEASA
ERLQGRRSRGASGSEPQQMGSDVRDLNALLPAVPSLGGGGGCALPVSGAA
QWAPVLDFAPPGASAYGSLGGPAPPPAPPPPPPPPHSFIKQEPSWGGAE
PHEEQCLSAFTVHFSGQFTGTAGACRYGPFGPPPPSQASSGQARMFPNAP
YLPSCLESQPAIRNQGYSTVTFDGTPSYGHTPSHHAAQFPNHSFKHEDPM
GQQGSLGEQQYSVPPPVYGCHTPTDSCTGSQALLLRTPYSSDNLYQMTSQ
LECMTWNQMNLGATLKGVAAGSSSSVKWTEGQSNHSTGYESDNHTTPILC
GAQYRIHTHGVFRGIQDVRRVPGVAPTLVRSASETSEKRPFMCAYPGCNK
RYFKLSHLQMHSRKHTGEKPYQCDFKDCERRFSRSDQLKRHQRRHTGVKP
FQCKTCQRKFSRSDHLKTHTRTHTGEKPFSCRWPSCQKKFARSDELVRHH
NMHQRNMTKLQLAL (SEQ ID NO: 201; GenBank Accession number

NP_077742).

In another embodiment, the WT1 molecule comprises the sequence:

(SEQ ID NO: 202)
MGHHHHHHHHHHSSGHIEGRHMRRVPGVAPTLVRSASETSEKRPFMCAYP

GCNKRYFKLSHLQMHSRKHTGEKPYQCDFKDCERRFFRSDQLKRHQRRHT

GVKPFQCKTCQRKFSRSDHLKTHTRTHTGEKPFSCRWPSCQKKFARSDEL

VRHHNMHQRNMTKLQLAL.

In other embodiments, the WT1 protein comprises one of the sequences set forth in one of the following GenBank sequence entries: NM_024426, NM_024425, NM_024424, NM_000378, 595530, D13624, D12496, D12497, AH003034, or X77549. In other embodiments, the WT1 protein has one of the sequences set forth in one of the above GenBank sequence entries. In another embodiment, the WT1 protein is any WT1 protein known in the art. In another embodiment, the WT1 protein has any other WT1 sequence known in the art.

In another embodiment, a peptide useful for the purposes of the present invention is derived from a fragment of a WT1 protein. In another embodiment, the process of derivation comprises introduction of the point mutation in the anchor residues of the HLA class I molecule binding motif. In another embodiment, the process of derivation consists of introduction of the point mutation in the anchor residues of the HLA class I molecule binding motif. In another embodiment, a peptide of the present invention differs from the corresponding fragment of a WT1 protein only by the point mutation in the HLA class I molecule binding motif anchor residue. In another embodiment, an HLA class I molecule binding motif of a peptide of the present invention differs from the corresponding WT1 sequence only by the point mutation in the anchor residue. Each possibility represents a separate embodiment of the present invention.

In another embodiment, the process of derivation of a peptide of the present invention further comprises one or more modifications of an amino acid (AA) to an AA analogue. In another embodiment, the process of derivation further comprises a modification of one or more peptide bond connecting two or more of the AA. In another embodiment, the AA analogue or peptide bond modification is one of the AA analogues or peptide bond modifications enumerated below. Each possibility represents a separate embodiment of the present invention.

The unmutated fragment of a WT1 protein wherefrom a peptide of the present invention (the "counterpart" in the wild-type sequence) is derived, in another embodiment, has the sequence SGQARMFPNAPYLPSCLES (SEQ ID NO: 5). In another embodiment, the unmutated WT1 fragment has the sequence QARMFPNAPYLPSCL (SEQ ID NO:6). In another embodiment, the unmutated WT1 fragment has the sequence LVRHHNMHQRNMTKL (SEQ ID NO:3). In another embodiment, the unmutated WT1 fragment has the sequence RSDELVRHHNMHQRNMTKL (SEQ ID NO:1). In another embodiment, the unmutated WT1 fragment has the sequence NKRYFKLSHLQMHSR (SEQ ID NO:4). In another embodiment, the unmutated WT1 fragment has the sequence PGCNKRYFKLSHLQMHSRKHTG (SEQ ID NO:2). In another embodiment, the unmutated WT1 fragment is any other WT1 fragment that contains an HLA class II molecule binding motif. In another embodiment, the unmutated WT1 fragment is any other WT1 fragment that contains an HLA-DR molecule binding motif. In another embodiment, the unmutated WT1 fragment contains multiple HLA-DR molecule binding motifs. In another embodiment, the unmutated WT1 fragment is any other WT1 fragment that contains an HLA-DRB molecule binding motif. In another embodiment, the unmutated WT1 fragment contains multiple HLA-DRB molecule binding motifs. In another embodiment, a peptide of the present invention differs from its counterpart only in the point mutation that it contains. In another embodiment, a peptide of the present invention differs from its counterpart only in a mutation in HLA class I anchor residue(s). Each possibility represents a separate embodiment of the present invention.

In another embodiment, a peptide of the present invention retains the ability to bind an HLA class II molecule, as exhibited by the unmutated WT1 fragment wherefrom the peptide was derived. In another embodiment, a peptide of the present invention retains ability to bind multiple HLA class II molecules, as exhibited by the unmutated WT1 fragment. Each possibility represents a separate embodiment of the present invention.

In another embodiment, the present invention provides an isolated peptide comprising the AA sequence GATLKGVAAGSSSSVKWT (SEQ ID NO:203) and LKGVAAGSSSSVKWT (SEQ ID NO:204).

"Peptide," in another embodiment of methods and compositions of the present invention, refers to a compound of subunit AA connected by peptide bonds. In another embodiment, the peptide comprises an AA analogue. In another embodiment, the peptide is a peptidomimetic. In another embodiment, a peptide of the present invention comprises one of the AA analogues enumerated below. The subunits are, in another embodiment, linked by peptide bonds. In another embodiment, the subunit is linked by another type of bond, e.g. ester, ether, etc. In another embodiment, a peptide of the present invention is one of the types of peptidomimetics enumerated below. Each possibility represents a separate embodiment of the present invention.

In another embodiment, a peptide of methods and compositions of the present invention binds with high affinity to the HLA class I molecule whose binding motif is contained therein. In other embodiments, the HLA class I molecule is any HLA class I molecule enumerated herein. In another embodiment, the peptide binds to the HLA class I molecule with medium affinity. In another embodiment, the peptide binds to the HLA class I molecule with significant affinity. In another embodiment, the peptide binds to the HLA class I molecule with measurable affinity. In another embodiment, the peptide exhibits stable binding to the HLA class I molecule. Each possibility represents a separate embodiment of the present invention.

In another embodiment, a peptide of methods and compositions of the present invention binds with high affinity to the HLA class II molecule whose binding motif is contained therein. In other embodiments, the HLA class II molecule is any HLA class II molecule enumerated herein. In another embodiment, the peptide binds with high affinity to more than 1 HLA class II molecules. In another embodiment, the peptide binds to the HLA class II molecule with medium affinity. In another embodiment, the peptide binds with medium affinity to more than 1 HLA class II molecules. In another embodiment, the peptide binds to the HLA class II molecule with significant affinity. In another embodiment, the peptide binds with significant affinity to more than 1 HLA class II molecules. In another embodiment, the peptide binds to the HLA class II molecule with measurable affinity. In another embodiment, the peptide binds with measurable affinity to more than 1 HLA class II molecules. In another embodiment, the peptide exhibits stable binding to the HLA class II molecule. In another embodiment, the peptide exhibits stable binding to more than 1 HLA class II molecules. Each possibility represents a separate embodiment of the present invention.

In another embodiment, a peptide of methods and compositions of the present invention binds to both an HLA class I molecule and an HLA class II molecule with significant affinity. In another embodiment, the peptide binds to both an HLA class I molecule and an HLA class II molecule with high affinity. In another embodiment, the peptide binds to both an HLA class I molecule and an HLA class II molecule with medium affinity. In another embodiment, the peptide binds to both an HLA class I molecule and an HLA class II molecule with measurable affinity. Each possibility represents a separate embodiment of the present invention.

"Fragment," in another embodiment, refers to a peptide of 11 or more AA in length. In another embodiment, a peptide fragment of the present invention is 16 or more AA long. In another embodiment, the fragment is 12 or more AA long. In another embodiment, the fragment is 13 or more AA. In another embodiment, the fragment is 14 or more AA. In another embodiment, the fragment is 15 or more AA. In another embodiment, the fragment is 17 or more AA. In another embodiment, the fragment is 18 or more AA. In another embodiment, the fragment is 19 or more AA. In another embodiment, the fragment is 22 or more AA. In another embodiment, the fragment is 8-12 AA. In another embodiment, the fragment is about 8-12 AA. In another embodiment, the fragment is 16-19 AA. In another embodiment, the fragment is about 16-19 AA. In another embodiment, the fragment 10-25 AA. In another embodiment, the fragment is about 10-25 AA. In another embodiment, the fragment has any other length. Each possibility represents a separate embodiment of the present invention.

In another embodiment, the present invention provides a composition comprising an isolated peptide of the invention in combination with at least 1 additional WT1 peptide. In certain embodiments, a composition comprising at least 2 different isolated peptides of the present invention is provided. In certain embodiments, a composition comprising at least 3 or at least 4 different isolated peptides of the present invention is provided. Each possibility represents a separate embodiment of the present invention. In certain embodiments, the composition of the present invention is a vaccine.

In another embodiment, a peptide of methods and compositions of the present invention binds an HLA class II molecule with significant affinity, while a peptide derived from the original peptide binds an HLA class I molecule with significant affinity.

In another embodiment, "affinity" refers to the concentration of peptide necessary for inhibiting binding of a standard peptide to the indicated MHC molecule by 50%. In another embodiment, "high affinity" refers to an affinity is such that a concentration of about 500 nanomolar (nM) or less of the peptide is required for 50% inhibition of binding of a standard peptide. In another embodiment, a concentration of about 400 nM or less of the peptide is required. In another embodiment, the binding affinity is 300 nM. In another embodiment, the binding affinity is 200 nM. In another embodiment, the binding affinity is 150 nM. In another embodiment, the binding affinity is 100 nM. In another embodiment, the binding affinity is 80 nM. In another embodiment, the binding affinity is 60 nM. In another embodiment, the binding affinity is 40 nM. In another embodiment, the binding affinity is 30 nM. In another embodiment, the binding affinity is 20 nM. In another embodiment, the binding affinity is 15 nM. In another embodiment, the binding affinity is 10 nM. In another embodiment, the binding affinity is 8 nM. In another embodiment, the binding affinity is 6 nM. In another embodiment, the binding affinity is 4 nM. In another embodiment, the binding affinity is 3 nM. In another embodiment, the binding affinity is 2 nM. In another embodiment, the binding affinity is 1.5 nM. In another embodiment, the binding affinity is 1 nM. In another embodiment, the binding affinity is 0.8 nM. In another embodiment, the binding affinity is 0.6 nM. In another embodiment, the binding affinity is 0.5 nM. In another embodiment, the binding affinity is 0.4 nM. In another embodiment, the binding affinity is 0.3 nM. In another embodiment, the binding affinity is less than 0.3 nM.

In another embodiment, "affinity" refers to a measure of binding strength to the MHC molecule. In another embodiment, affinity is measured using a method known in the art to measure competitive binding affinities. In another embodiment, affinity is measured using a method known in the art to measure relative binding affinities. In another embodiment, the method is a competitive binding assay. In another embodiment, the method is radioimmunoassay or RIA. In another embodiment, the method is BiaCore analyses. In another embodiment, the method is any other method known in the art. In another embodiment, the method yields an IC50 in relation to an IC50 of a reference peptide of known affinity.

Each type of affinity and method of measuring affinity represents a separate embodiment of the present invention.

In another embodiment, "high affinity" refers to an IC50 of 0.5-100 nM. In another embodiment, the IC50 is 1-100 nM. In another embodiment, the IC50 is 1.5-200 nM. In another embodiment, the IC50 is 2-100 nM. In another embodiment, the IC50 is 3-100 nM. In another embodiment, the IC50 is 4-100 nM. In another embodiment, the IC50 is 6-100 nM. In another embodiment, the IC50 is 10-100 nM. In another embodiment, the IC50 is 30-100 nM. In another embodiment, the IC50 is 3-80 nM. In another embodiment, the IC50 is 4-60 nM. In another embodiment, the IC50 is 5-50 nM. In another embodiment, the IC50 is 6-50 nM. In another embodiment, the IC50 is 8-50 nM. In another embodiment, the IC50 is 10-50 nM. In another embodiment, the IC50 is 20-50 nM. In another embodiment, the IC50 is 6-40 nM. In another embodiment, the IC50 is 8-30 nM. In another embodiment, the IC50 is 10-25 nM. In another embodiment, the IC50 is 15-25 nM. Each affinity and range of affinities represents a separate embodiment of the present invention.

In another embodiment, "medium affinity" refers to an IC50 of 100-500 nM. In another embodiment, the IC50 is 100-300 nM. In another embodiment, the IC50 is 100-200 nM. In another embodiment, the IC50 is 50-100 nM. In another embodiment, the IC50 is 50-80 nM. In another embodiment, the IC50 is 50-60 nM. Each affinity and range of affinities represents a separate embodiment of the present invention.

"Significant affinity" refers, in another embodiment, to sufficient affinity to mediate recognition of a target cell by a T cell carrying a T cell receptor (TCR) that recognizes the MHC molecule-peptide complex. In another embodiment, the term refers to sufficient affinity to mediate recognition of a cancer cell by a T cell carrying a TCR that recognizes the MHC molecule-peptide complex. In another embodiment, the term refers to sufficient affinity to mediate activation of a naive T cell by a dendritic cell presenting the peptide. In another embodiment, the term refers to sufficient affinity to mediate activation of a naive T cell by an APC presenting the peptide. In another embodiment, the term refers to sufficient affinity to mediate re-activation of a memory T cell by a dendritic cell presenting the peptide. In another embodiment, the term refers to sufficient affinity to mediate re-activation of a memory T cell by an APC presenting the peptide. In another embodiment, the term refers to sufficient affinity to mediate re-activation of a memory T cell by a somatic cell presenting the peptide. Each possibility represents a separate embodiment of the present invention.

"Measurable affinity" refers, in another embodiment, to sufficient affinity to be measurable by an immunological assay. In another embodiment, the immunological assay is any assay enumerated herein. Each possibility represents a separate embodiment of the present invention.

In another embodiment, a peptide of methods and compositions of the present invention binds to a superfamily of HLA molecules. Superfamilies of HLA molecules share very similar or identical binding motifs. In another embodiment, the superfamily is a HLA class I superfamily. In another embodiment, the superfamily is a HLA class II superfamily. Each possibility represents a separate embodiment of the present invention.

The terms "HLA-binding peptide," "HLA class I molecule-binding peptide," and "HLA class II molecule-binding peptide" refer, in another embodiment, to a peptide that binds an HLA molecule with measurable affinity. In another embodiment, the terms refer to a peptide that binds an HLA molecule with high affinity. In another embodiment, the terms refer to a peptide that binds an HLA molecule with sufficient affinity to activate a T cell precursor. In another embodiment, the terms refer to a peptide that binds an HLA molecule with sufficient affinity to mediate recognition by a T cell. The HLA molecule is, in other embodiments, any of the HLA molecules enumerated herein. Each possibility represents a separate embodiment of the present invention.

In another embodiment, a peptide of methods and compositions of the present invention is heteroclitic. "Heteroclitic" refers, in another embodiment, to a peptide that generates an immune response that recognizes the original peptide from which the heteroclitic peptide was derived (e.g. the peptide not containing the anchor residue mutations). In another embodiment, "original peptide" refers to a fragment of WT1 protein. For example, a peptide termed "WT1 122A1," having the sequence SGQAYMFPNAPYLPSCLES (SEQ ID NO:124), was generated from the wild-type WT1 peptide SGQARMFPNAPYLPSCLES (SEQ ID NO:5) by mutation of residue 5 to arginine. The heteroclitic mutation introduced the CD8$^+$ WT1 peptide RMFPNAPYL (SEQ ID NO:7) peptide generated YMFPNAPYL (SEQ ID NO:124), the WT1A1 peptide. In another embodiment, "heteroclitic" refers to a peptide that generates an immune response that recognizes the original peptide from which the heteroclitic peptide was derived, wherein the immune response generated by vaccination with the heteroclitic peptide is greater than the immune response generated by vaccination with the original peptide. In another embodiment, a "heteroclitic" immune response refers to an immune response that recognizes the original peptide from which the improved peptide was derived (e.g. the peptide not containing the anchor residue mutations). In another embodiment, a "heteroclitic" immune response refers to an immune response that recognizes the original peptide from which the heteroclitic peptide was derived, wherein the immune response generated by vaccination with the heteroclitic peptide is greater than the immune response generated by vaccination with the original peptide. In another embodiment, the magnitude of the immune response generated by vaccination with the heteroclitic peptide is greater than the immune response substantially equal to the response to vaccination with the original peptide. In another embodiment, the magnitude of the immune response generated by vaccination with the heteroclitic peptide is greater than the immune response less than the response to vaccination with the original peptide. Each possibility represents a separate embodiment of the present invention.

In another embodiment, a heteroclitic peptide of the present invention induces an immune response that is increased at least 2-fold relative to the WT1 peptide from which the heteroclitic peptide was derived ("native peptide"). In another embodiment, the increase is 3-fold relative to the native peptide. In another embodiment, the increase is 5-fold relative to the native peptide. In another embodiment, the increase is 7-fold relative to the native peptide. In another embodiment, the increase is 10-fold relative to the native peptide. In another embodiment, the increase is 15-fold relative to the native peptide. In another embodiment, the increase is 20-fold relative to the native peptide. In another embodiment, the increase is 30-fold relative to the native peptide. In another embodiment, the increase is 50-fold relative to the native peptide. In another embodiment, the increase is 100-fold relative to the native peptide. In another embodiment, the increase is 150-fold relative to the native peptide. In another embodiment, the increase is 200-fold relative to the native peptide. In another embodiment, the increase is 300-fold relative to the native peptide. In another embodiment, the increase is 500-fold relative to the native peptide. In another embodiment, the increase is 1000-fold relative to the native peptide. In another embodiment, the increase is more than 1000-fold relative to the native peptide. Each possibility represents a separate embodiment of the present invention.

In another embodiment, a heteroclitic peptide of the present invention is an HLA class I heteroclitic peptide. In another embodiment, a heteroclitic peptide of the present invention is an HLA class II heteroclitic peptide. In another embodiment, a heteroclitic class II peptide of the present invention is mutated in a class II binding residue. In another embodiment, a heteroclitic class II peptide of the present invention is identified and tested in a manner analogous to identification and testing of HLA class I heteroclitic peptides, as exemplified herein. Each possibility represents a separate embodiment of the present invention.

"Anchor motifs" or "anchor residues" refers, in another embodiment, to one or a set of preferred residues at particular positions in an HLA-binding sequence. For example, residues at positions 1, 2, 3, 6, and 9 are used as anchor residues. In another embodiment, the HLA-binding sequence is an HLA class II-binding sequence. In another embodiment, the HLA-binding sequence is an HLA class I-binding sequence. In another embodiment, the positions corresponding to the anchor motifs are those that play a significant role in binding the HLA molecule. In another embodiment, the anchor residue is a primary anchor motif. In another embodiment, the anchor residue is a secondary anchor motif. Each possibility represents a separate embodiment of the present invention.

In another embodiment, "anchor residues" are residues in positions 1, 3, 6, and 9 of the HLA class I binding motif. In another embodiment, the term refers to positions 1, 2, 6, and 9 of the HLA class I binding motif. In another embodiment, the term refers to positions 1, 6, and 9 of the HLA class I binding motif. In another embodiment, the term refers to positions 1, 2, and 9 of the HLA class I binding motif. In another embodiment, the term refers to positions 1, 3, and 9 of the HLA class I binding motif. In another embodiment, the term refers to positions 2 and 9 of the HLA class I binding motif. In another embodiment, the term refers to positions 6 and 9 of the HLA class I binding motif.

Each possibility represents a separate embodiment of the present invention.

Methods for identifying MHC class II epitopes are well known in the art. In another embodiment, the MHC class II epitope is predicted using TEPITOPE (Meister G E, Roberts C G et al, Vaccine 1995 13: 581-91). In another embodiment, the MHC class II epitope is identified using EpiMatrix (De Groot A S, Jesdale B M et al, AIDS Res Hum Retroviruses 1997 13: 529-31). In another embodiment, the MHC class II epitope is identified using the Predict Method (Yu K, Petrovsky N et al, Mol Med. 2002 8: 137-48). In another embodiment, the MHC class II epitope is identified using the SYFPEITHI epitope prediction algorithm. SYFPEITHI is a database comprising more than 4500 peptide sequences known to bind class I and class II MHC molecules. SYFPEITHI provides a score based on the presence of certain amino acids in certain positions along the MHC-binding groove. Ideal amino acid anchors are valued at 10 points, unusual anchors are worth 6-8 points, auxiliary anchors are worth 4-6 points, preferred residues are worth 1-4 points; negative amino acid effect on the binding score between −1 and −3. The maximum score for HLA-A*0201 is 36.

In another embodiment, the MHC class II epitope is identified using Rankpep. Rankpep uses position specific scoring matrices (PSSMs) or profiles from sets of aligned peptides known to bind to a given MHC molecule as the predictor of MHC-peptide binding. Rankpep includes information on the score of the peptide and the % optimum or percentile score of the predicted peptide relative to that of a consensus sequence that yields the maximum score, with the selected profile. Rankpep includes a selection of 102 and 80 PSSMs for the prediction of peptide binding to MHC I and MHC II molecules, respectively. Several PSSMs for the prediction of peptide binders of different sizes are usually available for each MHC I molecule.

In another embodiment, the MHC class II epitope is identified using SVMHC (Donnes P, Elofsson A. Prediction of MHC class I binding peptides, using SVMHC. BMC Bioinformatics. 2002 Sep. 11; 3:25). In another embodiment, the MHC class II epitope is identified using any other method known in the art. The above methods are utilized, in another embodiment, to identify MHC class II binding will be perturbed by introduction of an MHC class I anchor residue mutation into the WT1 sequence. Each possibility represents a separate embodiment of the present invention.

Methods for identifying MHC class I epitopes are well known in the art. In another embodiment, the MHC class I epitope is predicted using BIMAS software. The BIMAS score is based on the calculation of the theoretical half-life of the MHC-I/$\beta_2$-microglobulin/peptide complex, which is a measure of peptide-binding affinity. The program uses information about HLA-I peptides of 8-10 amino acids in length. The higher the binding affinity of a peptide to the MHC, the higher the likelihood that this peptide represents an epitope. The BIMAS algorithm assumes that each amino acid in the peptide contributes independently to binding to the class I molecule. Dominant anchor residues, which are critical for binding, have coefficients in the tables that are significantly higher than 1. Unfavorable amino acids have positive coefficients that are less than 1. If an amino acid is not known to make either a favorable or unfavorable contribution to binding, then is assigned the value 1. All the values assigned to the amino acids are multiplied and the resulting running score is multiplied by a constant to yield an estimate of half-time of dissociation.

In another embodiment, the MHC class I epitope is identified using SYFPEITHI. In another embodiment, the MHC class I epitope is identified using SVMHC (Donnes P, Elofsson A. Prediction of MHC class I binding peptides, using SVMHC. BMC Bioinformatics. 2002 Sep. 11; 3:25). In another embodiment, the MHC class I epitope is identified using NetMHC-2.0 (Sensitive quantitative predictions of peptide-MHC binding by a 'Query by Committee' artificial neural network approach. Buus S, Lauemoller S L, Worning P, Kesmir C, Frimurer T, Corbet S, Fomsgaard A, Hilden J, Holm A, Brunak S. Tissue Antigens., 62:378-84, 2003). In another embodiment, the MHC class I epitope is identified using any other method known in the art. The above methods are utilized, in another embodiment, to identify MHC class I epitopes that can be created by introduction of an anchor residue mutation into the WT1 sequence. Each possibility represents a separate embodiment of the present invention.

In another embodiment, the mutation that enhances MHC binding is in the residue at position 1 of the HLA class I binding motif. In another embodiment, the residue is changed to tyrosine. In another embodiment, the residue is changed to glycine. In another embodiment, the residue is changed to threonine. In another embodiment, the residue is changed to phenylalanine. In another embodiment, the residue is changed to any other residue known in the art. In another embodiment, a substitution in position 1 (e.g. to tyrosine) stabilizes the binding of the position 2 anchor residue.

In another embodiment, the mutation is in position 2 of the HLA class I binding motif. In another embodiment, the residue is changed to leucine. In another embodiment, the residue is changed to valine. In another embodiment, the residue is changed to isoleucine. In another embodiment, the residue is changed to methionine. In another embodiment, the residue is changed to any other residue known in the art.

In another embodiment, the mutation is in position 6 of the HLA class I binding motif. In another embodiment, the residue is changed to valine. In another embodiment, the residue is changed to cysteine. In another embodiment, the residue is changed to glutamine. In another embodiment, the residue is changed to histidine. In another embodiment, the residue is changed to any other residue known in the art.

In another embodiment, the mutation is in position 9 of the HLA class I binding motif. In another embodiment, the mutation changes the residue at the C-terminal position thereof. In another embodiment, the residue is changed to valine. In another embodiment, the residue is changed to threonine. In another embodiment, the residue is changed to isoleucine. In another embodiment, the residue is changed to leucine. In another embodiment, the residue is changed to alanine. In another embodiment, the residue is changed to cysteine. In another embodiment, the residue is changed to any other residue known in the art.

In another embodiment, the point mutation is in a primary anchor residue. In another embodiment, the HLA class I primary anchor residues are positions 2 and 9. In another embodiment, the point mutation is in a secondary anchor residue. In another embodiment, the HLA class I secondary anchor residues are positions 1 and 8. In another embodiment, the HLA class I secondary anchor residues are positions 1, 3, 6, 7, and 8. In another embodiment, the point mutation is in a position selected from positions 4, 5, and 8. Each possibility represents a separate embodiment of the present invention.

In another embodiment, the point mutation is in 1 or more residues in positions selected from positions 1, 2, 8, and 9 of the HLA class I binding motif. In another embodiment, the point mutation is in 1 or more residues in positions selected from positions 1, 3, 6, and 9. In another embodiment, the point mutation is in 1 or more residues in positions selected from positions 1, 2, 6, and 9. In another embodiment, the point mutation is in 1 or more residues in positions selected from positions 1, 6, and 9. In another embodiment, the point mutation is in 1 or more residues in positions selected from positions 1, 2, and 9. In another embodiment, the point mutation is in 1 or more residues in positions selected from positions 1, 3, and 9. In another embodiment, the point mutation is in 1 or more residues in positions selected from positions 2 and 9. In another embodiment, the point mutation is in 1 or more residues in positions selected from positions 6 and 9. Each possibility represents a separate embodiment of the present invention.

In another embodiment, the mutation is in the 4 position of the HLA class I binding motif. In another embodiment, the mutation is in the 5 position of the HLA class I binding motif. In another embodiment, the mutation is in the 7 position of the HLA class I binding motif. In another embodiment, the mutation is in the 8 position of the HLA class I binding motif. Each possibility represents a separate embodiment of the present invention.

Each of the above anchor residues and substitutions represents a separate embodiment of the present invention.

In another embodiment, the HLA class II binding site in a peptide of the present invention is created or improved by mutation of an HLA class II motif anchor residue. In another embodiment, the anchor residue that is modified is in the P1 position. In another embodiment, the anchor residue is at the P2 position. In another embodiment, the anchor residue is at the P6 position. In another embodiment, the anchor residue is at the P9 position. In another embodiment, the anchor residue is selected from the P1, P2, P6, and P9 positions. In another embodiment, the anchor residue is at the P3 position. In another embodiment, the anchor residue is at the P4 position. In another embodiment, the anchor residue is at the P5 position. In another embodiment, the anchor residue is at the P6 position. In another embodiment, the anchor residue is at the P8 position. In another embodiment, the anchor residue is at the P10 position. In another embodiment, the anchor residue is at the P11 position. In another embodiment, the anchor residue is at the P12 position. In another embodiment, the anchor residue is at the P13 position. In another embodiment, the anchor residue is at any other anchor residue of an HLA class II molecule that is known in the art. In another embodiment, residues other than P1, P2, P6, and P9 serve as secondary anchor residues; therefore, mutating them can improve HLA class II binding. In another embodiment, any combination of the above residues is mutated. Each possibility represents a separate embodiment of the present invention.

In another embodiment, the present invention provides a method of inducing an anti-mesothelioma immune response in a subject, the method comprising the step of contacting the subject with an immunogenic composition comprising (a) a WT1 protein; (b) a fragment of a WT protein; (c) a nucleotide molecule encoding a WT1 protein; or (d) a nucleotide molecule encoding a fragment of a WT1 protein, and at least one checkpoint inhibitor, thereby inducing an anti-mesothelioma immune response in a subject.

In another embodiment, the present invention provides a method of treating a subject with a mesothelioma, the method comprising the step of administering to the subject an immunogenic composition comprising (a) a WT1 protein; (b) a fragment of a WT protein; (c) a nucleotide molecule encoding a WT1 protein; or (d) a nucleotide molecule encoding a fragment of a WT1 protein, and at least one checkpoint inhibitor, thereby treating a subject with a mesothelioma.

In another embodiment, the present invention provides a method of reducing an incidence of a mesothelioma, or its relapse, in a subject, the method comprising the step of administering to the subject an immunogenic composition comprising (a) a WT1 protein; (b) a fragment of a WT protein; (c) a nucleotide molecule encoding a WT1 protein; or (d) a nucleotide molecule encoding a fragment of a WT1 protein, and at least one checkpoint inhibitor, thereby reducing an incidence of a mesothelioma, or its relapse, in a subject.

The terms "homology," "homologous," etc., when in reference to any protein or peptide, refer, in another embodiment, to a percentage of AA residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

In another embodiment, the term "homology," when in reference to any nucleic acid sequence similarly indicates a percentage of nucleotides in a candidate sequence that are identical with the nucleotides of a corresponding native nucleic acid sequence.

Homology is, in another embodiment, determined by computer algorithm for sequence alignment, by methods well described in the art. In other embodiments, computer algorithm analysis of nucleic acid sequence homology includes the utilization of any number of software packages available, such as, for example, the BLAST, DOMAIN, BEAUTY (BLAST Enhanced Alignment Utility), GENPEPT and TREMBL packages.

The percent identity between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm in a sequence analysis software. Protein analysis software matches similar sequences using measures of similarity assigned to various substitutions, deletions and other modifications, including conservative amino acid substitutions.

The percent identity between two amino acid sequences can be determined, e.g., using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. Polypeptide sequences can also be compared using FASTA, applying default or recommended parameters. A program in GCG Version 6.1., FASTA (e.g., FASTA2 and FASTA3) provides alignments and percent sequence identity of the regions of the best overlap between the query and search sequences (Pearson, Methods Enzymol. 1990; 183: 63-98; Pearson, Methods Mol. Biol. 2000; 132:185-219). The percent identity between two amino acid sequences can also be determined using the algorithm of E. Meyers and W. Miller (Comput. Appl. Biosci., 1988; 11-17) which has been incorporated into the ALIGN program (version 2.0), using a PAM120 weight residue table, a gap length penalty of 12 and a gap penalty of 4.

Another algorithm for comparing a sequence to other sequences contained in a database is the computer program BLAST, especially blastp, using default parameters. See, e.g., Altschul et al., J. Mol. Biol. 1990; 215:403-410; Altschul et al., Nucleic Acids Res. 1997; 25:3389-402 (1997); each herein incorporated by reference. The protein sequences of the present invention can there be used as a "query sequence" to perform a search against public databases to, for example, identify related sequences. Such searches can be performed using the XBLAST program (version 2.0) of Altschul, et al. 1990 (supra). BLAST protein searches can be performed with the XBLAST program, score=50, wordlength=3 to obtain amino acid sequences homologous to WT1 peptides of the invention. To obtain gapped alignments for comparison purposes, Gapped BLAST can be utilized as described in Altschul et al., 1997 (supra). When utilizing BLAST and Gapped BLAST programs, the default parameters of the respective programs (e.g., XBLAST and NBLAST) can be used.

In another embodiment, "homology" with respect to a homologous sequence refers to percent identity to a sequence disclosed herein of greater than 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. Each possibility represents a separate embodiment of the present invention.

In another embodiment, the present invention provides a composition comprising a peptide and at least one checkpoint inhibitor. In another embodiment, the composition further comprises a pharmaceutically acceptable carrier. In another embodiment, the composition further comprises an adjuvant. In another embodiment, the composition comprises 2 or more peptides of the present invention. In another embodiment, the composition further comprises any of the additives, compounds, or excipients set forth herein below. In another embodiment, the adjuvant is an alum salt or other mineral adjuvant, bacterial product or bacteria-derived adjuvant, tensoactive agent (e.g., saponin), o/w or w/o emulsion, liposome adjuvant, cytokine (e.g., IL-2, GM-CSF, IL-12, and IFN-gamma), or alpha-galactosylceramide analog. In another embodiment, the adjuvant is QS21, Freund's complete or incomplete adjuvant, aluminum phosphate, aluminum hydroxide, BCG or alum. In other embodiments, the carrier is any carrier enumerated herein. In other embodiments, the adjuvant is any adjuvant enumerated herein. Each possibility represents a separate embodiment of the present invention.

In another embodiment, this invention provides a vaccine comprising a peptide of the present invention and at least one checkpoint inhibitor. In another embodiment, the vaccine further comprises a carrier. In another embodiment, the vaccine further comprises an adjuvant. In another embodiment, the vaccine further comprises a combination of a carrier and an adjuvant. In another embodiment, the vaccine further comprises an APC. In another embodiment, the vaccine further comprises a combination of an APC and a carrier or an adjuvant. In another embodiment, the vaccine is a cell-based composition. Each possibility represents a separate embodiment of the present invention.

In another embodiment, this invention provides an immunogenic composition comprising a peptide of the present invention and at least one checkpoint inhibitor. In another embodiment, the immunogenic composition further comprises a carrier. In another embodiment, the immunogenic composition further comprises an adjuvant. In another embodiment, the immunogenic composition further comprises a combination of a carrier and an adjuvant. Each possibility represents a separate embodiment of the present invention.

In another embodiment, the term "vaccine" refers to a material or composition that, when introduced into a subject, provides a prophylactic or therapeutic response for a particular disease, condition, or symptom of same. In another embodiment, this invention comprises peptide-based vaccines, wherein the peptide comprises any embodiment listed herein, optionally further including immunomodulating compounds such as cytokines, adjuvants, etc.

In other embodiments, a composition or vaccine of methods and compositions of the present invention further comprises an adjuvant. In another embodiment, the adjuvant is Montanide ISA 51. Montanide ISA 51 contains a natural metabolizable oil and a refined emulsifier. In another embodiment, the adjuvant is GM-CSF. In another embodiment, the adjuvant is keyhole limpet hemocyanin (KLH), which may be conjugated to the peptide antigen or may be administered together with the peptide. Recombinant GM-CSF is a human protein grown, in another embodiment, in a yeast (*S. cerevisiae*) vector. GM-CSF promotes clonal expansion and differentiation of hematopoietic progenitor cells, APC, and dendritic cells and T cells.

In another embodiment, the adjuvant is a cytokine. In another embodiment, the adjuvant is a growth factor. In another embodiment, the adjuvant is a cell population. In another embodiment, the adjuvant is QS21. In another embodiment, the adjuvant is Freund's incomplete adjuvant. In another embodiment, the adjuvant is aluminum phosphate. In another embodiment, the adjuvant is aluminum hydroxide. In another embodiment, the adjuvant is BCG. In another embodiment, the adjuvant is alum. In another embodiment, the adjuvant is an interleukin. In another embodiment, the adjuvant is a chemokine. In another embodiment, the adjuvant is any other type of adjuvant known in the art. In another embodiment, the WT1 vaccine comprises two of the above adjuvants. In another embodiment, the WT1 vaccine comprises more than two of the above adjuvants. Each possibility represents a separate embodiment of the present invention.

In another embodiment, the WT1 vaccine used in the methods of the present invention can be one or more nucleic acid molecules (DNA or RNA) encoding one or more WT1 peptides of the present invention. In the practice of this embodiment, a vaccine comprising nucleic acid molecules encoding the one or more WT1 peptides (a nucleic acid vaccine) is administered and one or more checkpoint inhibitors are administered to the patient. In all other embodiments of the invention, the nucleic acid vaccine can be used in place of the peptide vaccine. The nucleic acid may be introduced alone, as part of a viral carrier, or inside of a cell, possibly as a plasmid or integrated into the cell's nucleic acid. The cell carrier may be the patient's cells, removed from the patient, or a cell from a donor, or a cell line. The cell may be an antigen presenting cell such as a dendritic cell or monocyte/macrophage lineage cell. The cellular vector is selected from the group consisting of a cell, such as autologous cell, allogeneic cell, cell line, dendritic cell or antigen presenting cell, or fusion of any of the above cells into a hybrid cell.

The WT1 peptide or the nucleic acid encoding it, or its carrier in any of the forms herein described may be exposed to the CTL's ex vivo or in vivo. If in vitro or ex vivo, the cells may be grown or expanded and then introduced into the patient.

As used interchangeably herein, the terms "nucleic acid", "nucleic acid molecule", "oligonucleotide", and "polynucleotide" include RNA, DNA, or RNA/DNA hybrid sequences of more than one nucleotide in either single chain or duplex form. The terms encompass "modified nucleotides" which comprise at least one modification, including by way of example and not limitation: (a) an alternative linking group, (b) an analogous form of purine, (c) an analogous form of pyrimidine, or (d) an analogous sugar. For examples of analogous linking groups, purines, pyrimidines, and sugars see for example PCT publication No. WO 95/04064. The nucleic acid sequences of the invention may be prepared by any known method, including synthetic, recombinant, ex vivo generation, or a combination thereof, as well as utilizing any purification methods known in the art. As used herein, the term "nucleic acid vaccine" is inclusive of DNA vaccines and RNA vaccines, and vaccines comprising a viral or non-viral vector.

In another embodiment, the uses of the present invention provides a vector comprising a nucleic acid molecule (DNA or RNA). In other embodiments, a composition or vaccine used in the practice of the present invention can comprise any of the embodiments of WT1 peptides of the present invention and combinations thereof. Each possibility represents a separate embodiment of the present invention.

In another embodiment, a vaccine for use in the practice of the present invention or a composition of the present invention comprises two peptides that are derived from the same WT1 fragment, each containing a different HLA class I heteroclitic peptide. In another embodiment, the two HLA class I heteroclitic peptides contain mutations in different HLA class I molecule anchor residues. In another embodiment, the two HLA class I heteroclitic peptides contain different mutations in the same anchor residue(s). Each possibility represents a separate embodiment of the present invention.

In another embodiment, the peptides in a composition used in the present invention bind to two distinct HLA class II molecules. In another embodiment, the peptides bind to three distinct HLA class II molecules. In another embodiment, the peptides bind to four distinct HLA class II molecules. In another embodiment, the peptides bind to five distinct HLA class II molecules. In another embodiment, the peptides bind to more than five distinct HLA class II molecules. In another embodiment, the peptides in the composition bind to the same HLA class II molecules.

In another embodiment, each of the peptides in a composition or method of use of the present invention binds to a set of HLA class II molecules. In another embodiment, each of the peptides binds to a distinct set of HLA class II molecules. In another embodiment, the peptides in the composition bind to the same set of HLA class II molecules. In another embodiment, two of the peptides bind to a distinct but overlapping set of HLA class II molecules. In another embodiment, two or more of the peptides bind to the same set of HLA class II molecules, while another of the peptides binds to a distinct set. In another embodiment, two or more of the peptides bind to an overlapping set of HLA class II molecules, while another of the peptides binds to a distinct set.

In another embodiment, the peptides for use in the practice of the invention or in a composition of the present invention bind to two distinct HLA class I molecules. In another embodiment, the peptides bind to three distinct HLA class I molecules. In another embodiment, the peptides bind to four distinct HLA class I molecules. In another embodiment, the peptides bind to five distinct HLA class I molecules. In another embodiment, the peptides bind to more than five distinct HLA class I molecules. In another embodiment, the peptides in the composition bind to the same HLA class I molecules.

In another embodiment, each of the peptides for use in the practice of the invention or in a composition of the present invention binds to a set of HLA class I molecules. In another embodiment, each of the peptides binds to a distinct set of HLA class I molecules. In another embodiment, the peptides in the composition bind to the same set of HLA class I molecules. In another embodiment, two of the peptides bind to a distinct but overlapping set of HLA class I molecules. In another embodiment, two or more of the peptides bind to the same set of HLA class I molecules, while another of the peptides binds to a distinct set. In another embodiment, two or more of the peptides bind to an overlapping set of HLA class I molecules, while another of the peptides binds to a distinct set.

In another embodiment, a "set of HLA class II molecules" or "set of HLA class I molecules" refers to the HLA molecules encoded by different alleles at a particular locus. In another embodiment, the term refers to HLA molecules with a particular binding specificity. In another embodiment, the term refers to HLA molecules with a particular peptide consensus sequence. In another embodiment, the term refers to a superfamily of HLA class II molecules. Each possibility represents a separate embodiment of the present invention.

Each of the above compositions and types of compositions represents a separate embodiment of the present invention.

Any embodiments described herein regarding peptides, nucleic acids, compositions, and vaccines of this invention may be employed in any of the methods of this invention. Each combination of peptide, nucleic acid, composition, or vaccine with a method represents a separate embodiment thereof.

In another embodiment, the present invention provides a method of treating a subject with a WT1-expressing cancer, the method comprising administering to the subject a WT1 vaccine as described herein and a checkpoint inhibitor, thereby treating a subject with a WT1-expressing cancer. In another embodiment, the present invention provides a method of treating a subject with a WT1-expressing cancer, the method comprising administering to the subject a composition of the present invention comprising at least one WT1 peptide and at least one checkpoint inhibitor, thereby treating a subject with a WT1-expressing cancer. In another embodiment, the present invention provides a method of treating a subject with a WT1-expressing cancer, the method comprising administering to the subject an immunogenic composition such as a vaccine and a checkpoint inhibitor, thereby treating a subject with a WT1-expressing cancer.

In another embodiment, the present invention provides a method of suppressing or halting the progression of a WT1-expressing cancer in a subject, the method comprising administering to the subject at least one WT1 peptide and at least one checkpoint inhibitor, thereby suppressing or halting the progression of a WT1-expressing cancer. In another embodiment, the present invention provides a method of suppressing or halting the progression of a WT1-expressing cancer in a subject, the method comprising administering to the subject a composition comprising at least one WT1 peptide and at least one checkpoint inhibitor, thereby suppressing or halting the progression of a WT1-expressing cancer. In another embodiment, the present invention provides a method of suppressing or halting the progression of a WT1-expressing cancer in a subject, the method comprising administering to the subject an immunogenic composition such as a vaccine of the present invention, comprising at least one WT1 peptide and at least one checkpoint inhibitor, thereby suppressing or halting the progression of a WT1-expressing cancer In another embodiment, the present invention provides a method of reducing the incidence of a WT1-expressing cancer in a subject, the method comprising administering to the subject at least one WT1 peptide and at least one checkpoint inhibitor, thereby reducing the incidence of a WT1-expressing cancer in a subject. In another embodiment, the present invention provides a method of reducing the incidence of a WT1-expressing cancer in a subject, the method comprising administering to the subject a composition of the present invention comprising at least one WT1 peptide and at least one checkpoint inhibitor, thereby reducing the incidence of a WT1-expressing cancer in a subject. In another embodiment, the present invention provides a method of reducing the incidence of a WT1-expressing cancer in a subject, the method comprising administering to the subject an immunogenic composition such as a vaccine of the present invention comprising at least one WT1 peptide and at least one checkpoint inhibitor, thereby reducing the incidence of a WT1-expressing cancer in a subject.

In another embodiment, the present invention provides a method of reducing the incidence of relapse of a WT1-expressing cancer in a subject, the method comprising administering to the subject a composition comprising at least one WT1 peptide and at least one checkpoint inhibitor, thereby reducing the incidence of relapse of a WT1-expressing cancer in a subject. In another embodiment, the present invention provides a method of reducing the incidence of relapse of a WT1-expressing cancer in a subject, the method comprising administering to the subject a composition of the present invention comprising at least one WT1 peptide and at least one checkpoint inhibitor, thereby reducing the incidence of relapse of a WT1-expressing cancer in a subject. In another embodiment, the present invention provides a method of reducing the incidence of relapse of a WT1-expressing cancer in a subject, the method comprising administering to the subject an immunogenic composition such as a vaccine of the present invention comprising at least one WT1 peptide and at least one checkpoint inhibitor, thereby reducing the incidence of relapse of a WT1-expressing cancer in a subject In another embodiment, the present invention provides a method of overcoming a T cell tolerance of a subject to a WT1-expressing cancer, the method comprising administering to the subject at least one WT1 peptide and at least one checkpoint inhibitor, thereby overcoming a T cell tolerance to a WT1-expressing cancer. In another embodiment, the present invention provides a method of overcoming a T cell tolerance of a subject to a WT1-expressing cancer, the method comprising administering to the subject a composition of the present invention comprising at least one WT1 peptide and at least one checkpoint inhibitor, thereby overcoming a T cell tolerance to a WT1-expressing cancer. In another embodiment, the present invention provides a method of overcoming a T cell tolerance of a subject to a WT1-expressing cancer, the method comprising administering to the subject an immunogenic composition such as a vaccine of the present invention comprising at least one WT1 peptide and at least one checkpoint inhibitor, thereby overcoming a T cell tolerance to a WT1-expressing cancer In another embodiment, the present invention provides a method of treating a subject having a WT1-expressing cancer, comprising (a) inducing in a donor formation and proliferation of human cytotoxic T lymphocytes (CTL) that recognize a malignant cell of the cancer by a method of the present invention; and (b) infusing the human CTL into the subject, thereby treating a subject having a cancer. In one embodiment, the donor is administered at least one WT1 peptide, and the CTL from said donor are infused into the subject and the subject is administered a checkpoint inhibitor, thereby treating a subject having a cancer. In one embodiment, the donor is administered at least one WT1 peptide and at least one checkpoint inhibitor, and the CTL from said donor are infused into the subject and the subject, thereby treating a subject having a cancer. In one embodiment, the donor is administered at least one WT1 peptide and at least one checkpoint inhibitor, and the CTL from said donor are infused into the subject and the subject is administered a checkpoint inhibitor, thereby treating a subject having a cancer.

In another embodiment, the present invention provides a method of treating a subject having a WT1-expressing cancer, comprising (a) inducing ex vivo formation and proliferation of human CTL that recognize a malignant cell of the cancer by a method of the present invention, wherein the human immune cells are obtained from a donor; and (b) infusing the human CTL into the subject, thereby treating a subject having a cancer. In one embodiment, a checkpoint inhibitor is included in the ex vivo step. In another embodiment a checkpoint inhibitor is administered to the subject. In another embodiment both the ex vivo step includes a checkpoint inhibitor, and the subject is also administered a checkpoint inhibitor.

Methods for ex vivo immunotherapy are well known in the art and are described, for example, in Davis I D et al (Blood dendritic cells generated with Flt3 ligand and CD40 ligand prime CD8+ T cells efficiently in cancer patients. J Immunother. 2006 September-October; 29(5):499-511) and Mitchell M S et al (The cytotoxic T cell response to peptide analogs of the HLA-A*0201-restricted MUC1 signal sequence epitope, M1.2. Cancer Immunol Immunother. 2006 Jul. 28). Each method represents a separate embodiment of the present invention.

In another embodiment, the present invention provides a method of inducing formation and proliferation of a WT1 protein-specific CTL, the method comprising contacting a lymphocyte population with an immunogenic composition such as a vaccine of the present invention together with at least one checkpoint inhibitor, thereby inducing formation and proliferation of a WT1 protein-specific CTL. In another embodiment, the immunogenic composition comprises an antigen-presenting cell (APC) associated with a peptide of the present invention and a checkpoint inhibitor. In another embodiment, the present invention provides a method of inducing formation and proliferation of a WT1 protein-specific CTL, the method comprising contacting a lymphocyte population with a peptide or composition of the present invention, together with at least one checkpoint inhibitor, thereby inducing formation and proliferation of a WT1 protein-specific CTL. In another embodiment, the present invention provides a method of inducing formation and proliferation of a WT1 protein-specific CTL, the method comprising contacting a lymphocyte population with a vaccine of the present invention, together with at least one checkpoint inhibitor, thereby inducing formation and proliferation of a WT1 protein-specific CTL. In another embodiment, the CTL is specific for a WT1-expressing cell. In another embodiment, the target cell is a cell of a WT1-expressing cancer. Each possibility represents a separate embodiment of the present invention.

In another embodiment, the present invention provides a method of inducing in a subject formation and proliferation of a WT1 protein-specific CTL, the method comprising contacting the subject with an immunogenic composition such as a vaccine of the present invention, together with at least one checkpoint inhibitor, thereby inducing in a subject formation and proliferation of a WT1 protein-specific CTL. In another embodiment, the immunogenic composition comprises an APC associated with a mixture of peptides of the present invention, which is administered together with at least one checkpoint inhibitor. In another embodiment, the present invention provides a method of inducing in a subject formation and proliferation of a WT1 protein-specific CTL, the method comprising contacting the subject with a peptide together with at least one checkpoint inhibitor, or composition of the present invention, thereby inducing in a subject formation and proliferation of a WT1 protein-specific CTL. In another embodiment, the present invention provides a method of inducing in a subject formation and proliferation of a WT1 protein-specific CTL, the method comprising contacting the subject with a vaccine of the present invention, together with at least one checkpoint inhibitor, thereby inducing in a subject formation and proliferation of a WT1 protein-specific CTL. In another embodiment, the target cell is a cell of a WT1-expressing cancer. In another embodiment, the subject has the WT1-expressing cancer. In another embodiment, the CTL is specific for a WT1-expressing cell.

In another embodiment, this invention provides a method of generating a heteroclitic immune response in a subject, wherein the heteroclitic immune response is directed against a WT1-expressing cancer, the method comprising administering to the subject at least one heteroclitic WT1 peptide, together with at least one checkpoint inhibitor, or composition of the present invention, thereby generating a heteroclitic immune response. In another embodiment, this invention provides a method of generating a heteroclitic immune response in a subject, wherein the heteroclitic immune response is directed against a WT1-expressing cancer, the method comprising administering to the subject an immunogenic composition such as a vaccine of the present invention, together with at least one checkpoint inhibitor, thereby generating a heteroclitic immune response. In another embodiment, this invention provides a method of generating a heteroclitic immune response in a subject, wherein the heteroclitic immune response is directed against a WT1-expressing cancer, the method comprising administering to the subject a vaccine of the present invention, together with at least one checkpoint inhibitor, thereby generating a heteroclitic immune response.

Each method represents a separate embodiment of the present invention.

In another embodiment, the WT1-expressing cancer is an acute myelogenous leukemia (AML). In another embodiment, the WT1-expressing cancer is a chronic myelogenous leukemia (CML). In another embodiment, the WT1-expressing cancer is associated with a myelodysplastic syndrome (MDS). In another embodiment, the WT1-expressing cancer is an MDS. In another embodiment, the WT1-expressing cancer is a non-small cell lung cancer (NSCLC). In another embodiment, the WT1-expressing cancer is an esophageal squamous cell carcinoma. In another embodiment, the WT1-expressing cancer is an acute lymphoblastic leukemia (ALL). In another embodiment, the WT1-expressing cancer is a bone or soft tissue sarcoma. In another embodiment, the WT1-expressing cancer is a Wilms' tumor. In another embodiment, the WT1-expressing cancer is a leukemia. In another embodiment, the WT1-expressing cancer is a hematological cancer. In another embodiment, the WT1-expressing cancer is a lymphoma. In another embodiment, the WT1-expressing cancer is a desmoplastic small round cell tumor. In another embodiment, the WT1-expressing cancer is a mesothelioma. In another embodiment, the WT1-expressing cancer is a malignant mesothelioma. In another embodiment, the WT1-expressing cancer is a gastric cancer. In another embodiment, the WT1-expressing cancer is a colon cancer. In another embodiment, the WT1-expressing cancer is a lung cancer. In another embodiment, the WT1-expressing cancer is a breast cancer. In another embodiment, the WT1-expressing cancer is a germ cell tumor. In another embodiment, the WT1-expressing cancer is a malignant pleural mesothelioma. In another embodiment, the WT1-expressing cancer is multiple myeloma. In another embodiment, the WT1-expressing cancer is myeloid leukemia. In another embodiment, the WT1-expressing cancer is an astrocytic cancer. In another embodiment, the WT1-expressing cancer is a glioblastoma (e.g., glioblastoma multiforme). In another embodiment, the WT1-expressing cancer is a colorectal adenocarcinoma. In another embodiment, the WT1-expressing cancer is an ovarian cancer (e.g., serous, epithelial, or endometrial). In another embodiment, the WT1-expressing cancer is breast cancer. In another embodiment, the WT1-expressing cancer is melanoma. In another embodiment, the WT1-expressing cancer is head and neck squamous cell carcinoma. In another embodiment, the WT1-expressing cancer is pancreatic ductal cell carcinoma. In another embodiment, the WT1-expressing cancer is a neuroblastoma. In another embodiment, the WT1-expressing cancer is a uterine cancer. In another embodiment, the WT1-expressing cancer is a thyroid cancer. In another embodiment, the WT1-expressing cancer is a hepatocellular carcinoma. In another embodiment, the WT1-expressing cancer is a thyroid cancer. In another embodiment, the WT1-expressing cancer is a liver cancer. In another embodiment, the WT1-expressing cancer is a renal cancer (e.g., renal cell carcinoma). In another embodiment, the WT1-expressing cancer is a Kaposi's sarcoma. In another embodiment, the WT1-expressing cancer is a sarcoma. In another embodiment, the WT1-expressing cancer is any other carcinoma or sarcoma.

In another embodiment, the WT1-expressing cancer is a solid tumor. In another embodiment, the solid tumor is associated with a WT1-expressing cancer. In another embodiment, the solid tumor is associated with a myelodysplastic syndrome (MDS). In another embodiment, the solid tumor is associated with a non-small cell lung cancer (NSCLC). In another embodiment, the solid tumor is associated with a lung cancer. In another embodiment, the solid tumor is associated with a breast cancer. In another embodiment, the solid tumor is associated with a colorectal cancer. In another embodiment, the solid tumor is associated with a prostate cancer. In another embodiment, the solid tumor is associated with an ovarian cancer. In another embodiment, the solid tumor is associated with a renal cancer. In another embodiment, the solid tumor is associated with a pancreatic cancer. In another embodiment, the solid tumor is associated with a brain cancer. In another embodiment, the solid tumor is associated with a gastrointestinal cancer. In another embodiment, the solid tumor is associated with a skin cancer. In another embodiment, the solid tumor is associated with a melanoma.

In another embodiment, a cancer or tumor treated by a method of the present invention is suspected to express WT1. In another embodiment, WT1 expression has not been verified by testing of the actual tumor sample. In another embodiment, the cancer or tumor is of a type known to express WT1 in many cases. In another embodiment, the type expresses WT1 in the majority of cases.

Each type of WT1-expressing cancer or tumor, and cancer or tumor suspected to express WT1, represents a separate embodiment of the present invention.

A non-exhaustive list of cancer types that may be treated using the compositions and methods of the invention is provided in Table 2.

TABLE 2

| Examples of Cancer Types | |
|---|---|
| Acute Lymphoblastic Leukemia, Adult | Hairy Cell Leukemia |
| | Head and Neck Cancer |
| Acute Lymphoblastic Leukemia, Childhood | Hepatocellular (Liver) Cancer, Adult (Primary) |
| Acute Myeloid Leukemia, Adult | Hepatocellular (Liver) Cancer, Childhood (Primary) |
| Acute Myeloid Leukemia, Childhood | Hodgkin's Lymphoma, Adult |
| | Hodgkin's Lymphoma, Childhood |
| Adrenocortical Carcinoma | Hodgkin's Lymphoma During Pregnancy |
| Adrenocortical Carcinoma, Childhood | Hypopharyngeal Cancer |
| AIDS-Related Cancers | Hypothalamic and Visual Pathway Glioma, Childhood |
| AIDS-Related Lymphoma | |
| Anal Cancer | Intraocular Melanoma |
| Astrocytoma, Childhood | Islet Cell Carcinoma (Endocrine |

TABLE 2-continued

Examples of Cancer Types

Cerebellar Astrocytoma, Childhood
Cerebral Basal Cell Carcinoma
Bile Duct Cancer, Extrahepatic
Bladder Cancer
Bladder Cancer, Childhood
Bone Cancer, Osteosarcoma/Malignant Fibrous Histiocytoma
Brain Stem Glioma, Childhood
Brain Tumor, Adult
Brain Tumor, Brain Stem Glioma, Childhood
Brain Tumor, Cerebellar Astrocytoma, Childhood
Brain Tumor, Cerebral Astrocytoma/Malignant Glioma, Childhood
Brain Tumor, Ependymoma, Childhood
Brain Tumor, Medulloblastoma, Childhood
Brain Tumor, Supratentorial Primitive Neuroectodermal Tumors, Childhood
Brain Tumor, Visual Pathway and Hypothalamic Glioma, Childhood
Brain Tumor, Childhood
Breast Cancer
Breast Cancer, Childhood
Breast Cancer, Male
Bronchial Adenomas/Carcinoids, Childhood
Burkitt's Lymphoma
Carcinoid Tumor, Childhood
Carcinoid Tumor, Gastrointestinal
Carcinoma of Unknown Primary
Central Nervous System Lymphoma, Primary
Cerebellar Astrocytoma, Childhood
Cerebral Astrocytoma/Malignant Glioma, Childhood
Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see Mycosis Fungoides and Sézary Syndrome
Endometrial Cancer
Ependymoma, Childhood
Esophageal Cancer
Esophageal Cancer, Childhood
Ewing's Family of Tumors
Extracranial Germ Cell Tumor, Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid
Pancreas)
Kaposi's Sarcoma
Kidney (Renal Cell) Cancer
Kidney Cancer, Childhood
Laryngeal Cancer
Laryngeal Cancer, Childhood
Leukemia, Acute Lymphoblastic, Adult
Leukemia, Acute Lymphoblastic, Childhood
Leukemia, Acute Myeloid, Adult
Leukemia, Acute Myeloid, Childhood
Leukemia, Chronic Lymphocytic
Leukemia, Chronic Myelogenous
Leukemia, Hairy Cell
Lip and Oral Cavity Cancer
Liver Cancer, Adult (Primary)
Liver Cancer, Childhood (Primary)
Lung Cancer, Non-Small Cell
Lung Cancer, Small Cell
Lymphoma, AIDS-Related
Lymphoma, Burkitt's
Lymphoma, Cutaneous T-Cell, see Mycosis Fungoides and Sézary Syndrome
Lymphoma, Hodgkin's, Adult
Lymphoma, Hodgkin's, Childhood
Lymphoma, Hodgkin's During Pregnancy
Lymphoma, Non-Hodgkin's, Adult
Lymphoma, Non-Hodgkin's, Childhood
Lymphoma, Non-Hodgkin's During Pregnancy
Lymphoma, Primary Central Nervous System
Macroglobulinemia, Waldenström's
Malignant Fibrous Histiocytoma of Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with Occult Primary
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer
Nasopharyngeal Cancer, Childhood
Neuroblastoma
Non-Hodgkin's Lymphoma, Adult
Non-Hodgkin's Lymphoma, Childhood
Non-Hodgkin's Lymphoma During Pregnancy
Non-Small Cell Lung Cancer
Oral Cancer, Childhood
Oral Cavity Cancer, Lip and Oropharyngeal Cancer
Osteosarcoma/Malignant Fibrous Histiocytoma of Bone
Ovarian Cancer, Childhood
Ovarian Epithelial Cancer
Ovarian Germ Cell Tumor
Tumor
Germ Cell Tumor, Extracranial, Childhood
Germ Cell Tumor, Extragonadal
Germ Cell Tumor, Ovarian
Gestational Trophoblastic Tumor
Glioma, Adult
Glioma, Childhood Brain Stem
Glioma, Childhood Cerebral Astrocytoma
Glioma, Childhood Visual Pathway and Hypothalamic
Skin Cancer (Melanoma)
Skin Carcinoma, Merkel Cell
Small Cell Lung Cancer
Small Intestine Cancer
Soft Tissue Sarcoma, Adult
Soft Tissue Sarcoma, Childhood
Squamous Cell Carcinoma, see Skin Cancer (non-Melanoma)
Squamous Neck Cancer with Occult Primary, Metastatic
Stomach (Gastric) Cancer
Stomach (Gastric) Cancer, Childhood
Supratentorial Primitive Neuroectodermal Tumors, Childhood
T-Cell Lymphoma, Cutaneous, see Mycosis Fungoides and Sézary Syndrome
Testicular Cancer
Thymoma, Childhood
Thymoma and Thymic Carcinoma
Thyroid Cancer
Thyroid Cancer, Childhood
Transitional Cell Cancer of the Renal Pelvis and Ureter
Trophoblastic Tumor, Gestational
Unknown Primary Site, Carcinoma of, Adult
Unknown Primary Site, Cancer of, Childhood
Unusual Cancers of Childhood
Ureter and Renal Pelvis, Transitional Cell Cancer
Urethral Cancer
Uterine Cancer, Endometrial
Uterine Sarcoma
Vaginal Cancer
Visual Pathway and Hypothalamic Glioma, Childhood
Vulvar Cancer
Waldenström's Macroglobulinemia
Wilms' Tumor
Ovarian Low Malignant Potential Tumor
Pancreatic Cancer
Pancreatic Cancer, Childhood
Pancreatic Cancer, Islet Cell
Paranasal Sinus and Nasal Cavity Cancer
Parathyroid Cancer
Penile Cancer
Pheochromocytoma
Pineoblastoma and Supratentorial Primitive Neuroectodermal Tumors, Childhood
Pituitary Tumor
Plasma Cell Neoplasm/Multiple Myeloma
Pleuropulmonary Blastoma
Pregnancy and Breast Cancer
Pregnancy and Hodgkin's Lymphoma
Pregnancy and Non-Hodgkin's Lymphoma
Primary Central Nervous System Lymphoma
Prostate Cancer
Rectal Cancer
Renal Cell (Kidney) Cancer
Renal Cell (Kidney) Cancer, Childhood
Renal Pelvis and Ureter, Transitional Cell Cancer
Retinoblastoma
Rhabdomyosarcoma, Childhood
Salivary Gland Cancer
Salivary Gland Cancer, Childhood
Sarcoma, Ewing's Family of Tumors
Sarcoma, Kaposi's
Sarcoma, Soft Tissue, Adult
Sarcoma, Soft Tissue, Childhood
Sarcoma, Uterine
Sezary Syndrome
Skin Cancer (non-Melanoma)
Skin Cancer, Childhood
Stomach Cancer In another embodiment, multiple peptides of this invention together with at least one checkpoint inhibitor are used to stimulate an immune response in methods of the present invention.

As provided herein, heteroclitic peptides that elicit antigen-specific $CD8^+$ T cell responses can be created using methods of the present invention. WT1 peptides that elicit $CD4^+$ T cell responses to multiple HLA class II molecules can be identified. $CD4^+$ T cells recognize peptides bound to the HLA class II molecule on APC. In another embodiment, antigen-specific $CD4^+$ T cell responses assist in induction and maintenance of $CD8^+$ cytotoxic T cell (CTL) responses.

In another embodiment, peptides of the present invention administered together with at least one checkpoint inhibitor exhibit an enhanced ability to elicit CTL responses, due to their ability to bind both HLA class I and HLA class II molecules. In another embodiment, peptides of the present invention administered together with at least one checkpoint inhibitor exhibit an enhanced ability to elicit CTL responses, due to the ability of the checkpoint inhibitor to increase the survival and proliferation of WT1 specific CTLs. In another embodiment, vaccines of the present invention administered together with at least one checkpoint inhibitor have the advantage of activating or eliciting both $CD4^+$ and $CD8^+$ T cells that recognize WT1 antigens. In another embodiment, activation or eliciting both $CD4^+$ and $CD8^+$ T cells provides a synergistic anti-WT1 immune response, relative to activation of either population alone. In another embodiment, the enhanced immunogenicity of peptides of the present invention is exhibited in individuals of multiple HLA class II subtypes, due to the ability of peptides of the present invention to bind multiple HLA class II subtypes. Each possibility represents a separate embodiment of the present invention.

In another embodiment, activated $CD4^+$ cells enhance immunity by licensing dendritic cells, thereby sustaining the activation and survival of the cytotoxic T cells. In another embodiment, activated $CD4^+$ T cells induce tumor cell death by direct contact with the tumor cell or by activation of the apoptosis pathway. Mesothelioma tumor cells, for example, are able to process and present antigens in the context of HLA class I and class II molecules.

The methods disclosed herein will be understood by those in the art to enable design of other WT1-derived peptides that are capable of binding both HLA class I and HLA class II molecules. The methods further enable design of immunogenic compositions and vaccines combining WT1-derived peptides of the present invention. Each possibility represents a separate embodiment of the present invention.

In another embodiment, methods, peptides, vaccines, and/or immunogenic compositions administered together with at least one checkpoint inhibitor of the present invention have the advantage of activating or eliciting WT1-specific $CD4^+$ T cells containing multiple different HLA class II alleles. In another embodiment, the vaccines have the advantage of activating or eliciting WT1-specific $CD4^+$ T cells in a substantial proportion of the population. In another embodiment, the peptides activate WT1-specific $CD4^+$ T cells in 10% of the population. In another embodiment, the peptides activate WT1-specific $CD4^+$ T cells in 15% of the population. In another embodiment, the peptides activate WT1-specific $CD4^+$ T cells in 20% of the population. In another embodiment, the peptides activate WT1-specific $CD4^+$ T cells in 25% of the population. In another embodiment, the peptides activate WT1-specific $CD4^+$ T cells in 30% of the population. In another embodiment, the peptides activate WT1-specific $CD4^+$ T cells in 35% of the population. In another embodiment, the peptides activate WT1-specific $CD4^+$ T cells in 40% of the population. In another embodiment, the peptides activate WT1-specific $CD4^+$ T cells in 45% of the population. In another embodiment, the peptides activate WT1-specific $CD4^+$ T cells in 50% of the population. In another embodiment, the peptides activate WT1-specific $CD4^+$ T cells in 55% of the population. In another embodiment, the peptides activate WT1-specific $CD4^+$ T cells in 60% of the population. In another embodiment, the peptides activate WT1-specific $CD4^+$ T cells in 70% of the population. In another embodiment, the peptides activate WT1-specific $CD4^+$ T cells in 75% of the population. In another embodiment, the peptides activate WT1-specific $CD4^+$ T cells in 80% of the population. In another embodiment, the peptides activate WT1-specific $CD4^+$ T cells in 85% of the population. In another embodiment, the peptides activate WT1-specific $CD4^+$ T cells in 90% of the population. In another embodiment, the peptides activate WT1-specific $CD4^+$ T cells in 95% of the population. In another embodiment, the peptides activate WT1-specific $CD4^+$ T cells in greater than 95% of the population. In another embodiment, the vaccines activate or elicit WT1-specific $CD4^+$ T cells in a substantial proportion of a particular population (e.g. American Caucasians). Each possibility represents a separate embodiment of the present invention.

In another embodiment, methods of the present invention provide for an improvement in an immune response that has already been mounted by a subject. In another embodiment, methods of the present invention comprise administering the peptide, composition, or vaccine together with at least one checkpoint inhibitor one more time or two more times. In another embodiment, the peptides are varied in their composition, concentration, or a combination thereof. In another embodiment, the peptides administered together with at least one checkpoint inhibitor provide for the initiation of an immune response against an antigen of interest in a subject in which an immune response against the antigen of interest has not already been initiated. In another embodiment, the CTL that are induced proliferate in response to presentation of the peptide on the APC or cancer cell. In other embodiments, reference to modulation of the immune response involves, either or both the humoral and cell-mediated arms of the immune system, which is accompanied by the presence of Th2 and Th1 T helper cells, respectively, or in another embodiment, each arm individually.

In other embodiments, the methods affecting the growth of a tumor result in (1) the direct inhibition of tumor cell division, or (2) immune cell mediated tumor cell lysis, or both, which leads to a suppression in the net expansion of tumor cells. Each possibility represents a separate embodiment of the present invention. The use of the peptide or vaccine administered together with at least one checkpoint inhibitor increases the direct inhibition of tumor cell division, the immune cell mediated cell lysis, or both, greater than without the use of the checkpoint inhibitor.

Inhibition of tumor growth by either of these two mechanisms can be readily determined by one of ordinary skill in the art based upon a number of well-known methods. In another embodiment, tumor inhibition is determined by measuring the actual tumor size over a period of time. In another embodiment, tumor inhibition can be determined by estimating the size of a tumor (over a period of time) utilizing methods well known to those of skill in the art. More specifically, a variety of radiologic imaging methods (e.g., single photon and positron emission computerized tomography; see generally, "Nuclear Medicine in Clinical Oncology," Winkler, C. (ed.) Springer-Verilog, New York, 1986), can be utilized to estimate tumor size. Such methods can also utilize a variety of imaging agents, including for example, conventional imaging agents (e.g., Gallium-67 citrate), as well as specialized reagents for metabolite imaging, receptor imaging, or immunologic imaging (e.g., radiolabeled monoclonal antibody specific tumor markers). In addition, non-radioactive methods such as ultrasound (see, "Ultrasonic Differential Diagnosis of Tumors", Kossoff and Fukuda, (eds.), Igaku-Shoin, New York, 1984), can also be utilized to estimate the size of a tumor.

In addition to the in vivo methods for determining tumor inhibition discussed above, a variety of in vitro methods can be utilized in order to determine in vivo tumor inhibition. Representative examples include lymphocyte mediated antitumor cytolytic activity determined for example, by a $^{51}$Cr release assay, tumor dependent lymphocyte proliferation (Ioannides, et al., J. Immunol. 146(5):1700-1707, 1991), in vitro generation of tumor specific antibodies (Herlyn, et al., J. Immunol. Meth. 73:157-167, 1984), cell (e.g., CTL, helper T-cell) or humoral (e.g., antibody) mediated inhibition of cell growth in vitro (Gazit, et al., Cancer Immunol Immunother 35:135-144, 1992), and, for any of these assays, determination of cell precursor frequency (Vose, Int. J. Cancer 30:135-142 (1982), and others.

In another embodiment, methods of suppressing tumor growth indicate a growth state that is curtailed compared to growth without contact with, or exposure to a peptide administered together with at least one checkpoint inhibitor of this invention. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth refers, in other embodiments, to slowing, delaying, or stopping tumor growth, or to tumor shrinkage. Each possibility represents a separate embodiment of the present invention.

In another embodiment of methods and compositions of the present invention, WT1 expression is measured before administration of the treatment, after administration of the treatment, or both before and after administration of the treatment. In another embodiment, WT1 transcript expression is measured. In another embodiment, WT1 protein levels in the tumor or cancer cells are measured. In another embodiment, WT1 protein or peptides shed from cancer cells or tumor cells into circulation or other bodily fluids such as but not limited to urine are measured. Each possibility represents a separate embodiment of the present invention.

In another embodiment of methods and compositions of the invention, expression of the checkpoint protein(s) targeted by the one or more checkpoint inhibitors administered to the subject is measured (at the transcript level or protein level) in the tumor or cancer cells, or in whole blood, serum, or plasma, before administration of the treatment (baseline), after administration of the treat, or both before and after administration of the treatment. In one embodiment of methods and compositions of the invention, the one or more checkpoint proteins is selected from among: CTLA-4, PD-L1, PD-L2, PD1, B7-H3, B7-H4, BTLA, HVEM, TIM3, GAL9, LAG3, VISTA, KIR, 2B4, CD160, CGEN-15049, CHK 1 kinase, CHK2 kinase, A2aR, and B-7 family ligands. In one embodiment of methods and compositions of the invention, expression of PD1, PD2, CTLA4, or a combination of two or more of the foregoing are measured before administration of the treatment, after administration of the treatment, or both before and after administration of the treatment. In one embodiment, checkpoint protein expression is measured at a primary tumor site. In another embodiment, the cancer is metastatic and the checkpoint protein expression is measured at a metastatic site, or the primary tumor site, or both.

In another embodiment of methods and compositions of the invention, one or more of the following markers are measured before administration of the treatment (baseline), after administration of the treatment, or both before and after administration of the treatment: monocytic myeloid-derived suppressor cells (m-MDSCs), C-reactive protein (CRP), absolute lymphocytes, absolute lymphocytes, and lactate dehydrogenase (LDH). In another embodiment, use of one or more markers for predicting or identifying responsiveness to checkpoint modulation is embraced herein.

Methods of determining the presence and magnitude of an immune response are well known in the art. In another embodiment, lymphocyte proliferation assays, wherein T cell uptake of a radioactive substance, e.g. $^3$H-thymidine is measured as a function of cell proliferation. In other embodiments, detection of T cell proliferation is accomplished by measuring increases in interleukin-2 (IL-2) production, $Ca^{2+}$ flux, or dye uptake, such as 3-(4,5-dimethylthiazol-2-yl)-2, 5-diphenyl-tetrazolium. Each possibility represents a separate embodiment of the present invention.

In another embodiment, CTL stimulation is determined by means known to those skilled in the art, including detection of cell proliferation, cytokine production and others. Analysis of the types and quantities of cytokines secreted by T cells upon contacting ligand-pulsed targets can be a measure of functional activity. Cytokines can be measured by ELISA, ELISPOT assays or fluorescence-activated cell sorting (FACS) to determine the rate and total amount of cytokine production. (Fujihashi K. et al. (1993) J. Immunol. Meth. 160:181; Tanguay S. and Killion J. J. (1994) Lymphokine Cytokine Res. 13:259).

In another embodiment, CTL activity is determined by $^{51}$Cr-release lysis assay. Lysis of peptide-pulsed $^{51}$Cr-labeled targets by antigen-specific T cells can be compared for target cells pulsed with control peptide. In another embodiment, T cells are stimulated with a peptide of this invention, and lysis of target cells expressing the native peptide in the context of MHC can be determined. The kinetics of lysis as well as overall target lysis at a fixed timepoint (e.g., 4 hours) are used, in another embodiment, to evaluate ligand performance. (Ware C. F. et al. (1983) J Immunol 131: 1312).

Methods of determining affinity of a peptide for an HLA molecule are well known in the art. In another embodiment, affinity is determined by TAP stabilization assays.

In another embodiment, affinity is determined by competition radioimmunoassay. In another embodiment, the following protocol is utilized: Target cells are washed two times in PBS with 1% bovine serum albumin (BSA; Fisher Chemicals, Fairlawn, N.J.). Cells are resuspended at $10^7$/ml on ice, and the native cell surface bound peptides are stripped for 2 minutes at 0° C. using citrate-phosphate buffer in the presence of 3 mg/ml beta$_2$ microglobulin. The pellet is resuspended at $5 \times 10^6$ cells/ml in PBS/1% BSA in the presence of 3 mg/ml beta$_2$ microglobulin and 30 mg/ml deoxyribonuclease, and 200 ml aliquots are incubated in the presence or absence of HLA-specific peptides for 10 min at 20° C., then with $^{125}$I-labeled peptide for 30 min at 20° C. Total bound $^{125}$I is determined after two washes with PBS/2% BSA and one wash with PBS. Relative affinities are determined by comparison of escalating concentrations of the test peptide versus a known binding peptide.

In another embodiment, a specificity analysis of the binding of peptide to HLA on surface of live cells (e.g. SKLY-16 cells) is conducted to confirm that the binding is to the appropriate HLA molecule and to characterize its restriction. This includes, in another embodiment, competition with excess unlabeled peptides known to bind to the same or disparate HLA molecules and use of target cells which express the same or disparate HLA types. This assay is performed, in another embodiment, on live fresh or 0.25% paraformaldehyde-fixed human PBMC, leukemia cell lines and EBV-transformed T-cell lines of specific HLA types. The relative avidity of the peptides found to bind MHC molecules on the specific cells are assayed by competition assays as described above against $^{125}$I-labeled peptides of known high affinity for the relevant HLA molecule, e.g., tyrosinase or HBV peptide sequence.

In another embodiment, a WT1 peptide used in the methods and compositions of the present invention comprises one or more non-classical amino acids such as: 1,2,3,4-tetrahydroisoquinoline-3-carboxylate (Kazmierski et al. (1991) J. Am Chem. Soc. 113:2275-2283); (2S,3S)-methyl-phenylalanine, (2S,3R)-methyl-phenylalanine, (2R,3S)-methyl-phenylalanine and (2R,3R)-methyl-phenylalanine (Kazmierski and Hruby (1991) Tetrahedron Lett. 32(41): 5769-5772); 2-aminotetrahydronaphthalene-2-carboxylic acid (Landis (1989) Ph.D. Thesis, University of Arizona); hydroxy-1,2,3,4-tetrahydroisoquinoline-3-carboxylate (Miyake et al. (1984) J. Takeda Res. Labs. 43:53-76) histidine isoquinoline carboxylic acid (Zechel et al. (1991) Int. J. Pep. Protein Res. 38(2):131-138); and HIC (histidine cyclic urea), (Dharanipragada et al. (1993) Int. J. Pep. Protein Res. 42(1):68-77) and ((1992) Acta. Cryst., Crystal Struc. Comm. 48(IV):1239-124). Such non-classical amino acids are embodied in the modified peptides of the invention.

In another embodiment, a peptide used in the methods and compositions of the present invention comprises one or more AA analogs or is a peptidomimetic, which, in other embodiments, induces or favors specific secondary structures. Such peptides comprise, in other embodiments, the following: LL-Acp (LL-3-amino-2-propenidone-6-carboxylic acid), a ß-turn inducing dipeptide analog (Kemp et al. (1985) J. Org. Chem. 50:5834-5838); ß-sheet inducing analogs (Kemp et al. (1988) Tetrahedron Lett. 29:5081-5082); ß-turn inducing analogs (Kemp et al. (1988) Tetrahedron Left. 29:5057-5060); alpha-helix inducing analogs (Kemp et al. (1988) Tetrahedron Left. 29:4935-4938); gamma-turn inducing analogs (Kemp et al. (1989) J. Org. Chem. 54:109: 115); analogs provided by the following references: Nagai and Sato (1985) Tetrahedron Left. 26:647-650; and DiMaio et al. (1989) J. Chem. Soc. Perkin Trans. p. 1687; a Gly-Ala turn analog (Kahn et al. (1989) Tetrahedron Lett. 30:2317); amide bond isostere (Jones et al. (1988) Tetrahedron Left. 29(31):3853-3856); tretrazol (Zabrocki et al. (1988) J. Am. Chem. Soc. 110:5875-5880); DTC (Samanen et al. (1990) Int. J. Protein Pep. Res. 35:501:509); and analogs taught in Olson et al. (1990) J. Am. Chem. Sci. 112:323-333 and Garvey et al. (1990) J. Org. Chem. 55(3):936-940.

Conformationally restricted mimetics of beta turns and beta bulges, and peptides containing them, are described in U.S. Pat. No. 5,440,013, issued Aug. 8, 1995 to Kahn.

In other embodiments, a peptide used in a method of the invention is conjugated to one of various other molecules, as described hereinbelow, which can be via covalent or non-covalent linkage (complexed), the nature of which varies, in another embodiment, depending on the particular purpose.

In another embodiment, the peptide is covalently or non-covalently complexed to a macromolecular carrier, (e.g. an immunogenic carrier), including, but not limited to, natural and synthetic polymers, proteins, polysaccharides, polypeptides (amino acids), polyvinyl alcohol, polyvinyl pyrrolidone, and lipids. In another embodiment, a peptide of this invention is linked to a substrate. In another embodiment, the peptide is conjugated to a fatty acid, for introduction into a liposome (U.S. Pat. No. 5,837,249). In another embodiment, a peptide of the invention is complexed covalently or non-covalently with a solid support, a variety of which are known in the art. In another embodiment, linkage of the peptide to the carrier, substrate, fatty acid, or solid support serves to increase an elicited an immune response.

In other embodiments, the carrier is thyroglobulin, an albumin (e.g. human serum albumin), tetanus toxoid, polyamino acids such as poly (lysine: glutamic acid), an influenza protein, hepatitis B virus core protein, keyhole limpet hemocyanin, an albumin, or another carrier protein or carrier peptide; hepatitis B virus recombinant vaccine, or an APC. Each possibility represents a separate embodiment of the present invention.

In another embodiment, the term "amino acid" refers to a natural or, in another embodiment, an unnatural or synthetic AA, and can include, in other embodiments, glycine, D- or L optical isomers, AA analogs, peptidomimetics, or combinations thereof.

In another embodiment, the terms "cancer," "neoplasm," "neoplastic" or "tumor," are used interchangeably and refer to cells that have undergone a malignant transformation that makes them pathological to the host organism. The cancer may be of any stage within the numbered staging system (e.g., stage 0, stage 1, stage 2, stage 3, or stage 4), and any stage in the TNM staging system. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. In another embodiment, a tumor is detectable on the basis of tumor mass; e.g., by such procedures as CAT scan, magnetic resonance imaging (MRI), X-ray, ultrasound or palpation, and in another embodiment, is identified by biochemical or immunologic findings, the latter which is used to identify cancerous cells, as well, in other embodiments. A tumor may be a solid tumor or non-solid tumor.

Methods for synthesizing peptides are well known in the art. In another embodiment, the peptides of this invention are synthesized using an appropriate solid-state synthetic procedure (see for example, Steward and Young, *Solid Phase Peptide Synthesis*, Freemantle, San Francisco, Calif. (1968); Merrifield (1967) Recent Progress in Hormone Res 23: 451). The activity of these peptides is tested, in other embodiments, using assays as described herein.

In another embodiment, the peptides of this invention are purified by standard methods including chromatography (e.g., ion exchange, affinity, and sizing column chromatography), centrifugation, differential solubility, or by any other standard technique for protein purification. In another embodiment, immuno-affinity chromatography is used, whereby an epitope is isolated by binding it to an affinity column comprising antibodies that were raised against that peptide, or a related peptide of the invention, and were affixed to a stationary support.

In another embodiment, affinity tags such as hexa-His (Invitrogen), Maltose binding domain (New England Biolabs), influenza coat sequence (Kolodziej et al. (1991) Meth. Enzymol. 194:508-509), glutathione-S-transferase, or others, are attached to the peptides of this invention to allow easy purification by passage over an appropriate affinity column. Isolated peptides can also be physically characterized, in other embodiments, using such techniques as proteolysis, nuclear magnetic resonance, and x-ray crystallography.

In another embodiment, the peptides of this invention are produced by in vitro translation, through known techniques, as will be evident to one skilled in the art. In another embodiment, the peptides are differentially modified during or after translation, e.g., by phosphorylation, glycosylation, cross-linking, acylation, proteolytic cleavage, linkage to an antibody molecule, membrane molecule or other ligand, (Ferguson et al. (1988) Ann. Rev. Biochem. 57:285-320).

In another embodiment, the peptides of this invention further comprise a detectable label, which in another embodiment, is fluorescent, or in another embodiment, luminescent, or in another embodiment, radioactive, or in another embodiment, electron dense. In other embodiments, the dectectable label comprises, for example, green fluorescent protein (GFP), DS-Red (red fluorescent protein), secreted alkaline phosphatase (SEAP), beta-galactosidase, luciferase, $^{32}P$ $^{125}I$, $^{3}H$ and $^{14}C$, fluorescein and its derivatives, rhodamine and its derivatives, dansyl and umbelliferone, luciferin or any number of other such labels known to one skilled in the art. The particular label used will depend upon the type of immunoassay used.

In another embodiment, a peptide of this invention is linked to a substrate, which, in another embodiment, serves as a carrier. In another embodiment, linkage of the peptide to a substrate serves to increase an elicited an immune response.

In another embodiment, peptides of this invention are linked to other molecules, as described herein, using conventional cross-linking agents such as carbodimides. Examples of carbodimides are 1-cyclohexyl-3-(2-morpholinyl-(4-ethyl) carbodiimide (CMC), 1-ethyl-3-(3-dimethylaminopropyl) carbodiimide (EDC) and 1-ethyl-3-(4-azonia-44-dimethylpentyl) carbodiimide.

In other embodiments, the cross-linking agents comprise cyanogen bromide, glutaraldehyde and succinic anhydride. In general, any of a number of homo-bifunctional agents including a homo-bifunctional aldehyde, a homo-bifunctional epoxide, a homo-bifunctional imido-ester, a homo-bifunctional N-hydroxysuccinimide ester, a homo-bifunctional maleimide, a homo-bifunctional alkyl halide, a homo-bifunctional pyridyl disulfide, a homo-bifunctional aryl halide, a homo-bifunctional hydrazide, a homo-bifunctional diazonium derivative and a homo-bifunctional photoreactive compound can be used. Also envisioned, in other embodiments, are hetero-bifunctional compounds, for example, compounds having an amine-reactive and a sulfhydryl-reactive group, compounds with an amine-reactive and a photoreactive group and compounds with a carbonyl-reactive and a sulfhydryl-reactive group.

In other embodiments, the homo-bifunctional cross-linking agents include the bifunctional N-hydroxysuccinimide esters dithiobis(succinimidylpropionate), disuccinimidyl suberate, and disuccinimidyl tartarate; the bifunctional imido-esters dimethyl adipimidate, dimethyl pimelimidate, and dimethyl suberimidate; the bifunctional sulfhydryl-reactive crosslinkers 1,4-di-[3'-(2'-pyridyldithio)propionamido]butane, bismaleimidohexane, and bis-N-maleimido-1, 8-octane; the bifunctional aryl halides 1,5-difluoro-2,4-dinitrobenzene and 4,4'-difluoro-3,3'-dinitrophenylsulfone; bifunctional photoreactive agents such as bis-[b-(4-azidosalicylamido)ethyl]disulfide; the bifunctional aldehydes formaldehyde, malondialdehyde, succinaldehyde, glutaraldehyde, and adipaldehyde; a bifunctional epoxide such as 1,4-butaneodiol diglycidyl ether; the bifunctional hydrazides adipic acid dihydrazide, carbohydrazide, and succinic acid dihydrazide; the bifunctional diazoniums o-tolidine, diazotized and bis-diazotized benzidine; the bifunctional alkylhalides N1N'-ethylene-bis(iodoacetamide), N1N'-hexamethylene-bis(iodoacetamide), N1N'-undecamethylene-bis(iodoacetamide), as well as benzylhalides and halomustards, such as a1a'-diiodo-p-xylene sulfonic acid and tri(2-chloroethyl)amine, respectively.

In other embodiments, hetero-bifunctional cross-linking agents used to link the peptides to other molecules, as described herein, include, but are not limited to, SMCC (succinimidyl-4-(N-maleimidomethyl)cyclohexane-1-carboxylate), MBS (m-maleimidobenzoyl-N-hydroxysuccinimide ester), SIAB (N-succinimidyl(4-iodoacteyl)aminobenzoate), SMPB (succinimidyl-4-(p-maleimidophenyl) butyrate), GMBS (N-(.gamma.-maleimidobutyryloxy) succinimide ester), MPBH (4-(4-N-maleimidopohenyl) butyric acid hydrazide), M2C2H (4-(N-maleimidomethyl) cyclohexane-1-carboxyl-hydrazide), SMPT (succinimidyloxycarbonyl-a-methyl-a-(2-pyridyldithio)toluene), and SPDP (N-succinimidyl 3-(2-pyridyldithio)propionate).

In another embodiment, the peptides of the invention are formulated as non-covalent attachment of monomers through ionic, adsorptive, or biospecific interactions. Complexes of peptides with highly positively or negatively charged molecules can be accomplished, in another embodiment, through salt bridge formation under low ionic strength environments, such as in deionized water.

Large complexes can be created, in another embodiment, using charged polymers such as poly-(L-glutamic acid) or poly-(L-lysine), which contain numerous negative and positive charges, respectively. In another embodiment, peptides are adsorbed to surfaces such as microparticle latex beads or to other hydrophobic polymers, forming non-covalently associated peptide-superantigen complexes effectively mimicking cross-linked or chemically polymerized protein, in other embodiments. In another embodiment, peptides are non-covalently linked through the use of biospecific interactions between other molecules. For instance, utilization of the strong affinity of biotin for proteins such as avidin or streptavidin or their derivatives could be used to form peptide complexes. The peptides, according to this aspect, and in another embodiment, can be modified to possess biotin groups using common biotinylation reagents such as the N-hydroxysuccinimidyl ester of D-biotin (NHS-biotin), which reacts with available amine groups.

In another embodiment, a peptide of the present invention is linked to a carrier. In another embodiment, the carrier is KLH. In other embodiments, the carrier is any other carrier known in the art, including, for example, thyroglobulin, albumins such as human serum albumin, tetanus toxoid, polyamino acids such as poly (lysine:glutamic acid), influenza, hepatitis B virus core protein, hepatitis B virus recombinant vaccine and the like. Each possibility represents a separate embodiment of the present invention.

In another embodiment, the peptides of this invention are conjugated to a lipid, such as P3 CSS. In another embodiment, the peptides of this invention are conjugated to a bead.

In any of the foregoing embodiments, the peptide, cross-linked peptide, bound peptide or any other form of the peptide is used in a method of the invention together with at least one checkpoint inhibitor.

In another embodiment, in addition to the use of at least one checkpoint inhibitor, the methods and compositions of this invention further comprise immunomodulating compounds. In other embodiments, the immunomodulating compound is a cytokine, chemokine, or complement component that enhances expression of immune system accessory or adhesion molecules, their receptors, or combinations thereof. In some embodiments, the immunomodulating compound include interleukins, for example interleukins 1 to 15, interferons alpha, beta or gamma, tumor necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-1a and MIP-1b, complement components, or combinations thereof. In other embodiments, the immunomodulating compound stimulate expression, or enhanced expression of OX40, OX40L (gp34), lymphotactin, CD40, CD40L, B7.1, B7.2, TRAP, ICAM-1, 2 or 3, cytokine receptors, or combination thereof.

In another embodiment, the immunomodulatory compound induces or enhances expression of co-stimulatory molecules that participate in the immune response, which include, in some embodiments.

In one embodiment, patients administered the WT1 vaccine and the checkpoint inhibitor in accordance with the invention also are administered GM-CSF prior to or on the day of first vaccination, or the combination thereof. In one embodiment, a patient is administered 70 mcg of GM-CSF subcutaneously two days before and on the day of first vaccine administration.

In another embodiment, the composition comprises a solvent, including water, dispersion media, cell culture media, isotonic agents and the like. In another embodiment, the solvent is an aqueous isotonic buffered solution with a pH of around 7.0. In another embodiment, the composition comprises a diluent such as water, phosphate buffered saline, or saline. In another embodiment, the composition comprises a solvent, which is non-aqueous, such as propyl ethylene glycol, polyethylene glycol and vegetable oils.

In another embodiment, the composition is formulated for administration by any of the many techniques known to those of skill in the art. For example, this invention provides for administration of the pharmaceutical composition parenterally, intravenously, subcutaneously, intradermally, intramucosally, topically, orally, or by inhalation.

In another embodiment, in the uses of the vaccine comprising a peptide of this invention, the vaccine may further comprise a cell population, which, in another embodiment, comprises lymphocytes, monocytes, macrophages, dendritic cells, endothelial cells, stem cells or combinations thereof, which, in another embodiment are autologous, syngeneic or allogeneic, with respect to each other. In another embodiment, the cell population comprises a peptide of the present invention. In another embodiment, the cell population takes up the peptide. In one embodiment, the cell is an antigen presenting cell (APC). In a further embodiment, the APC is a professional APC. Each possibility represents a separate embodiment of the present invention.

In another embodiment, the cell populations of this invention are obtained from in vivo sources, such as, for example, peripheral blood, leukopheresis blood product, apheresis blood product, peripheral lymph nodes, gut associated lymphoid tissue, spleen, thymus, cord blood, mesenteric lymph nodes, liver, sites of immunologic lesions, e.g. synovial fluid, pancreas, cerebrospinal fluid, tumor samples, granulomatous tissue, or any other source where such cells can be obtained. In another embodiment, the cell populations are obtained from human sources, which are, in other embodiments, from human fetal, neonatal, child, or adult sources. In another embodiment, the cell populations of this invention are obtained from animal sources, such as, for example, porcine or simian, or any other animal of interest. In another embodiment, the cell populations of this invention are obtained from subjects that are normal, or in another embodiment, diseased, or in another embodiment, susceptible to a disease of interest.

In another embodiment, the cell populations of this invention are separated via affinity-based separation methods. Techniques for affinity separation include, in other embodiments, magnetic separation, using antibody-coated magnetic beads, affinity chromatography, cytotoxic agents joined to a monoclonal antibody or use in conjunction with a monoclonal antibody, for example, complement and cytotoxins, and "panning" with an antibody attached to a solid matrix, such as a plate, or any other convenient technique. In other embodiment, separation techniques include the use of fluorescence activated cell sorters, which can have varying degrees of sophistication, such as multiple color channels, low angle and obtuse light scattering detecting channels, impedance channels, etc. In other embodiments, any technique that enables separation of the cell populations of this invention can be employed, and is to be considered as part of this invention.

In another embodiment, the dendritic cells are from the diverse population of morphologically similar cell types found in a variety of lymphoid and non-lymphoid tissues, qualified as such (Steinman (1991) Ann. Rev. Immunol. 9:271-296). In another embodiment, the dendritic cells used in this invention are isolated from bone marrow, or in another embodiment, derived from bone marrow progenitor cells, or, in another embodiment, from isolated from/derived from peripheral blood, or in another embodiment, derived from, or are a cell line.

In another embodiment, the cell populations described herein are isolated from the white blood cell fraction of a mammal, such as a murine, simian or a human (See, e.g., WO 96/23060). The white blood cell fraction can be, in another embodiment, isolated from the peripheral blood of the mammal.

Methods of isolating dendritic cells are well known in the art. In another embodiment, the DC are isolated via a method which includes the following steps: (a) providing a white blood cell fraction obtained from a mammalian source by methods known in the art such as leukophoresis; (b) separating the white blood cell fraction of step (a) into four or more subfractions by countercurrent centrifugal elutriation; (c) stimulating conversion of monocytes in one or more fractions from step (b) to dendritic cells by contacting the cells with calcium ionophore, GM-CSF and IL-13 or GM-CSF and IL-4, (d) identifying the dendritic cell-enriched fraction from step (c); and (e) collecting the enriched fraction of step (d), preferably at about 4° C.

In another embodiment, the dendritic cell-enriched fraction is identified by fluorescence-activated cell sorting, which identifies, in another embodiment, at least one of the following markers: HLA-DR, HLA-DQ, or B7.2, and the simultaneous absence of the following markers: CD3, CD14, CD16, 56, 57, and CD 19, 20.

In another embodiment, the cell population comprises lymphocytes, which are, in another embodiment, T cells, or in another embodiment, B cells. The T cells are, in other embodiments, characterized as NK cells, helper T cells, cytotoxic T lymphocytes (CTL), TILs, naïve T cells, or combinations thereof. It is to be understood that T cells which are primary, or cell lines, clones, etc. are to be considered as part of this invention. In another embodiment, the T cells are CTL, or CTL lines, CTL clones, or CTLs isolated from tumor, inflammatory, or other infiltrates.

In another embodiment, hematopoietic stem or early progenitor cells comprise the cell populations used in this invention. In another embodiment, such populations are isolated or derived, by leukapheresis. In another embodiment, the leukapheresis follows cytokine administration, from bone marrow, peripheral blood (PB) or neonatal umbilical cord blood. In another embodiment the stem or progenitor cells are characterized by their surface expression of the surface antigen marker known as CD34$^+$, and exclusion of expression of the surface lineage antigen markers, Lin−.

In another embodiment, the subject is administered a peptide, composition or vaccine of this invention, in conjunction with bone marrow cells. In another embodiment, the administration together with bone marrow cells embodiment follows previous irradiation of the subject, as part of the course of therapy, in order to suppress, inhibit or treat cancer in the subject.

In another embodiment, the phrase "contacting a cell" or "contacting a population" refers to a method of exposure, which can be, in other embodiments, direct or indirect. In another embodiment, such contact comprises direct injection of the cell through any means well known in the art, such as microinjection. It is also envisaged, in another embodiment, that supply to the cell is indirect, such as via provision in a culture medium that surrounds the cell, or administration to a subject, via any route well known in the art, and as described herein.

In another embodiment, CTL generation of methods of the present invention is accomplished in vivo, and is effected by introducing into a subject an antigen presenting cell contacted in vitro with a peptide of this invention (See for example Paglia et al. (1996) J. Exp. Med. 183:317-322), administered together with at least one checkpoint inhibitor.

In another embodiment, the peptides of methods and compositions of the present invention are delivered to antigen-presenting cells (APC).

In another embodiment, the peptides are delivered to APC in the form of cDNA encoding the peptides. In another embodiment, the term "antigen-presenting cells" refers to dendritic cells (DC), monocytes/macrophages, B lymphocytes or other cell type(s) expressing the necessary MHC/co-stimulatory molecules, which effectively allow for T cell recognition of the presented peptide. In another embodiment, the APC is a cancer cell. Each possibility represents a separate embodiment of the present invention. In each embodiment, the vaccine or APC or any form of peptide delivery to the patient or subject is administered together with at least one checkpoint inhibitor. As noted herein, the administration of the at least one checkpoint inhibitor does not need to be in the same vaccine, formulation, administration site or time of administration of the WT1 vaccine or its alternate forms.

As embodied herein, the administration of the checkpoint inhibitor contemporaneously with the WT1 vaccine, in any of its various forms, enhances the formation of WT1-specific CTLs in the subject in need thereof.

In another embodiment, the CTL are contacted with two or more antigen-presenting cell populations, together with at least one checkpoint inhibitor. In another embodiment, the two or more antigen presenting cell populations present different peptides. Each possibility represents a separate embodiment of the present invention.

In another embodiment, techniques that lead to the expression of antigen in the cytosol of APC (e.g. DC) are used to deliver the peptides to the APC. Methods for expressing antigens on APC are well known in the art. In another embodiment, the techniques include (1) the introduction into the APC of naked DNA encoding a peptide of this invention, (2) infection of APC with recombinant vectors expressing a peptide of this invention, and (3) introduction of a peptide of this invention into the cytosol of an APC using liposomes. (See Boczkowski D. et al. (1996) J. Exp. Med. 184:465-472; Rouse et al. (1994) J. Virol. 68:5685-5689; and Nair et al. (1992) J. Exp. Med. 175:609-612).

In another embodiment, foster antigen presenting cells such as those derived from the human cell line 174× CEM.T2, referred to as T2, which contains a mutation in its antigen processing pathway that restricts the association of endogenous peptides with cell surface MHC class I molecules (Zweerink et al. (1993) J. Immunol. 150:1763-1771), are used, as exemplified herein.

In another embodiment, any of the methods described herein is used to elicit CTL, which are elicited in vitro. In another embodiment, the CTL are elicited ex-vivo. In another embodiment, the CTL are elicited in vitro. The resulting CTL, are, in another embodiment, administered to the subject, thereby treating the condition associated with the peptide, an expression product comprising the peptide, or a homologue thereof, administered together with at least one checkpoint inhibitor. Each possibility represents a separate embodiment of the present invention.

In another embodiment, the method entails introduction of the genetic sequence that encodes the peptides of this invention. In another embodiment, the method comprises administering to the subject a vector comprising a nucleotide sequence, which encodes a peptide of the present invention (Tindle, R. W. et al. Virology (1994) 200:54). In another embodiment, the method comprises administering to the subject naked nucleic acid (DNA or RNA) which encodes a peptide, or in another embodiment, two or more peptides of this invention (Nabel, et al. PNAS-USA (1990) 90: 11307). In another embodiment, multi-epitope, analogue-based cancer vaccines are utilized (Fikes et al, ibid).

Each possibility represents a separate embodiment of the present invention.

Nucleic acids (DNA or RNA) can be administered to a subject via any means as is known in the art, including parenteral or intravenous administration, or in another embodiment, by means of a gene gun. In another embodiment, the nucleic acids are administered in a composition, which correspond, in other embodiments, to any embodiment listed herein. DNA or RNA can be administered to a subject as a naked nucleic acid or carried by a vector.

Vectors for use according to methods of this invention can comprise, in another embodiment, any vector that facilitates or allows for the expression of a peptide of this invention (e.g., a WT1 peptide) in a cell in vitro or in a subject in vivo. The term "vector" is used to refer to any molecule (e.g., nucleic acid, plasmid, virus, particle) usable to transfer coding sequence information (e.g., nucleic acid sequence encoding a WT1 peptide) to a cell or subject. Nucleic acid vaccines for several cancers have entered clinical trials (Wahren B et al., "DNA Vaccines: Recent Developments and the Future," Vaccines, 2014, 2:785-796; Fioretti D. et al., "DNA Vaccines: Developing New Strategies Against Cancer, Journal of Biomedicine and Biotechnology, 2010, 2010 (938):174378). Strategies for expanding functional WT1-specific T cells using a DNA vaccine are known (Chaise C et al., "DNA vaccination induces WT1-specific T-cell responses with potential clinical relevance," Blood, 2008, 112(7):2956-2964). In one embodiment, the vector is a viral vector. In another embodiment, the vector is a non-viral vector. In one embodiment the non-viral vector is a nucleic acid vector such as plasmid DNA or mRNA vector (see, for example, Weide B. et al, "Plasmid DNA- and messenger RNA-based Anti-Cancer Vaccination," Immunol Lett, 2008, 115(1):33-42); Kim H. et al., "Self-Assembled Messenger RNA Nanoparticles (mRNA-NPs) for Efficient Gene Expression," Sci Rep, 2015, 5:12737); Ulmer J. B. et al. "RNA-based Vaccines", Vaccine, 2012, 30:4414-4418). In another embodiment, "vectors" includes attenuated viruses, such as vaccinia or fowlpox, such as described in, e.g., U.S. Pat. No. 4,722,848, incorporated herein by reference. In another embodiment, the vector is BCG (Bacille Calmette Guerin), such as described in Stover et al. (Nature 351:456-460 (1991)).

Other vectors useful for therapeutic administration or immunization of the peptides of the invention, e.g., *Salmonella typhi* vectors and the like, will be apparent to those skilled in the art from the description herein. Non-limiting examples of vectors that may be used to administer nucleic acid molecules to subjects in vivo and cells in vitro include adenovirus, adeno-associated virus, retrovirus, lentivirus, pox virus, herpes virus, virus-like particles (VLPs), plasmids, cationic lipids, liposomes, and nanoparticles.

A "coding sequence" is a nucleic acid sequence that is transcribed into mRNA and/or translated into a polypeptide. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences. Variants or analogs may be prepared by the deletion of a portion of the coding sequence, by insertion of a sequence, and/or by substitution of one or more nucleotides within the sequence. Techniques for modifying nucleic acid sequences, such as site-directed mutagenesis, are well known to those skilled in the art (See, e.g., Sambrook et al., Molecular Cloning: A Laboratory Manual, Second Edition, 1989; DNA Cloning, Vols. I and II, D. N. Glover ed., 1985). Optionally, the nucleic acid sequences of the present invention, and composition and methods of the invention that utilize such polynucleotides, can include non-coding sequences.

The term "operably-linked" is used herein to refer to an arrangement of flanking control sequences wherein the flanking sequences so described are configured or assembled so as to perform their usual function. Thus, a flanking control sequence operably-linked to a coding sequence may be capable of effecting the replication, transcription and/or translation of the coding sequence under conditions compatible with the control sequences. For example, a coding sequence is operably-linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably-linked" to the coding sequence. Each nucleic acid sequence coding for a polypeptide (e.g., a WT1 peptide) will typically have its own operably-linked promoter sequence.

In another embodiment, the vector further encodes for an immunomodulatory compound, as described herein. In another embodiment, the subject is administered an additional vector encoding same, concurrent, prior to or following administration of the vector encoding a peptide of this invention to the subject.

In another embodiment, the peptides, compositions and vaccines of this invention are administered to a subject, or utilized in the methods of this invention, in combination with other anti-cancer compounds and chemotherapeutics, including monoclonal antibodies directed against alternate cancer antigens, or, in another embodiment, epitopes that consist of an AA sequence which corresponds to, or in part to, that from which the peptides of this invention are derived. This is in addition to the use of at least one checkpoint inhibitor in the practice of the various embodiments of the invention.

In another embodiment, the present invention provides a method of detecting a WT1-specific CD4$^+$ T cell response in a subject, the method comprising administering to the subject a peptide, vaccine, or immunogenic composition of the present invention. In another embodiment, a delayed-type hypersensitivity test used to detect the WT1-specific CD4$^+$ T cell response. In another embodiment, a peptide of present invention is superior to its unmutated counterpart in inducing a CD4$^+$ T cell response in a subject. Each possibility represents a separate embodiment of the present invention.

As used herein, the terms "patient", "subject", and "individual" are used interchangeably and are intended to include human and non-human animal species. For example, the subject may be a human or non-human mammal. In some embodiments, the subject is a non-human animal model or veterinary patient. The subject may be any age or gender.

An immunogenic composition of methods and compositions of the present invention comprises, in another embodiment, an APC associated with a peptide of the present invention. In another embodiment, the immunogenic composition comprises an APC associated with a mixture of peptides of the present invention. In another embodiment, the immunogenic composition consists of an APC associated with a peptide of the present invention. In another embodiment, the immunogenic composition consists of an APC associated with a mixture of peptides of the present invention. Each possibility represents a separate embodiment of the present invention.

A composition of methods and compositions of the present invention is, in another embodiment, an immunogenic composition. In another embodiment, the composition is a pharmaceutical composition. In another embodiment, the composition is any other type of composition known in the art. Each possibility represents a separate embodiment of the present invention. Each composition further comprises at least one checkpoint inhibitor Various embodiments of dosage ranges are contemplated by this invention. In another embodiment, the dosage is 20 μg per peptide per day. In another embodiment, the dosage is 10 μg/peptide/day. In another embodiment, the dosage is 30 μg/peptide/day. In another embodiment, the dosage is 40 μg/peptide/day. In another embodiment, the dosage is 60 μg/peptide/day. In another embodiment, the dosage is 80 μg/peptide/day. In another embodiment, the dosage is 100 μg/peptide/day. In another embodiment, the dosage is 150 μg/peptide/day. In another embodiment, the dosage is 200 μg/peptide/day. In another embodiment, the dosage is 300 μg/peptide/day. In another embodiment, the dosage is 400 μg/peptide/day. In another embodiment, the dosage is 600 μg/peptide/day. In another embodiment, the dosage is 800 μg/peptide/day. In another embodiment, the dosage is 1000 μg/peptide/day.

In another embodiment, the dosage is 10 μg/peptide/dose. In another embodiment, the dosage is 30 μg/peptide/dose. In another embodiment, the dosage is 40 μg/peptide/dose. In another embodiment, the dosage is 60 μg/peptide/dose. In another embodiment, the dosage is 80 μg/peptide/dose. In another embodiment, the dosage is 100 μg/peptide/dose. In another embodiment, the dosage is 150 μg/peptide/dose. In another embodiment, the dosage is 200 μg/peptide/dose. In another embodiment, the dosage is 300 μg/peptide/dose. In another embodiment, the dosage is 400 μg/peptide/dose. In another embodiment, the dosage is 600 µg/peptide/dose. In another embodiment, the dosage is 800 µg/peptide/dose. In another embodiment, the dosage is 1000 µg/peptide/dose.

In another embodiment, the dosage is 10-20 µg/peptide/dose. In another embodiment, the dosage is 20-30 µg/peptide/dose. In another embodiment, the dosage is 20-40 µg/peptide/dose. In another embodiment, the dosage is 30-60 µg/peptide/dose. In another embodiment, the dosage is 40-80 µg/peptide/dose. In another embodiment, the dosage is 50-100 µg/peptide/dose. In another embodiment, the dosage is 50-150 µg/peptide/dose. In another embodiment, the dosage is 100-200 µg/peptide/dose. In another embodiment, the dosage is 200-300 µg/peptide/dose. In another embodiment, the dosage is 300-400 µg/peptide/dose. In another embodiment, the dosage is 400-600 µg/peptide/dose. In another embodiment, the dosage is 500-800 µg/peptide/dose. In another embodiment, the dosage is 800-1000 µg/peptide/dose.

In another embodiment, the total amount of peptide per dose or per day is one of the above amounts. In another embodiment, the total peptide dose per dose is one of the above amounts.

Each of the above doses represents a separate embodiment of the present invention.

In another embodiment, the present invention provides a kit comprising a peptide, composition or vaccine of the present invention, together with at least one checkpoint inhibitor. In another embodiment, the kit further comprises a label or packaging insert. In another embodiment, the kit is used for detecting a WT1-specific CD4 response through the use of a delayed-type hypersensitivity test. In another embodiment, the kit is used for any other method enumerated herein. In another embodiment, the kit is used for any other method known in the art. Each possibility represents a separate embodiment of the present invention.

EXAMPLE

Evaluation of Efficacy of WT1 Peptide Vaccine Administered Together with Nivolumab in Patients with Ovarian Cancer Eligible patients diagnosed with ovarian cancer will start the vaccination schedule within 4 months of completion of chemotherapy. Patients will initially receive 6 vaccinations of WT1 peptides over 12 weeks, and 7 infusions of the immune checkpoint inhibitor nivolumab over 14 weeks. Toxicity assessments will be performed with each dose of vaccine, and 3 weeks after the completion of therapy at week 15. Patients will be observed by the study staff for up to 30 minutes following treatment. No dose escalation is planned. Routine toxicity assessments will continue throughout the trial.

Patients who do not have disease progression at the week 15 evaluation are permitted to receive 4 additional vaccines administered approximately every 8 weeks. This maintenance vaccine course would begin at week 19.

Immune responses will be evaluated from 40 ml heparinized blood samples at 6 separate time-points: baseline (at consent and before first dose in order to determine baseline variations), before vaccines 5 and 6 as well as 3 weeks after the last nivolumab infusion. If feasible, an additional blood draw will be obtained at the 3-month follow-up.

Using ELISA, antibody levels generated against the 4 WT1 peptides in the vaccine will be measured. Antibodies are generally present by completion of the fourth vaccination. T-cell proliferative response assays will be performed on peripheral blood lymphocytes including: flow cytometry for phenotypic analysis with FACS including leukocyte subset analysis, T regulatory cell assay (including CD3, CD4, CD8, FOXP3, ICOS and PD1) and myeloid derived suppressor cells (MDSCs, CD14+HLA-DRlow cells) in peripheral blood and also in tumor (if optional biopsy obtained). WT1 T cell specific CD4 and CD8 proliferative response will be measured using polyfunctional intracellular cytokine staining (ICS) and flow cytometric based cytotoxicity assays using Meso Scale Discovery System with functionality measured by IFN-gamma production. Detailed procedures for blood sample processing, T cell monitoring, antibody ELISA and polyfunctional T cell assay, are described in [29].

Baseline values and T cell response results will be correlated with duration of clinical remission.

If a patient is removed from study prior to week 15, blood for post study immunologic studies will be obtained. A CT scan will be performed at baseline and week 15 (or sooner if deemed medically necessary) and every 3 months thereafter for up to 1 year until disease progression. MRI abdomen and pelvis may be used in lieu of the CT abdomen and pelvis. The reference radiologist will use immune-related response criteria to determine disease progression [57]. CA125 will be obtained at baseline, weeks 6 and 15 and then every 3 months thereafter for up to 1 year until disease progression. CA125 will not be used to determine disease progression due to the confounding possibility of inflammation in vaccinated patients. Patients will remain on study until the time of progression, development of unacceptable toxicity, completion of the vaccine sequence or patient withdrawal.

WT1 Vaccine: The vaccine that will be used in this study contains four separate WT1 peptides:
YMFPNAPYL (SEQ ID NO:124; WT1-A1): HLA class I peptide with a mutated amino acid R126Y to stimulate CD8+ responses.
SGQAYMFPNAPYLPSCLES (SEQ ID NO:125; WT1-122A1 long): HLA class II peptide containing an embedded WT1-A1 heteroclitic sequence within the longer peptide to stimulate both CD4+ and CD8+ responses according to data from preclinical and phase 1 studies.
RSDELVRHHNMHQRNMTKL (SEQ ID NO:1; WT1-427 long) and PGCNKRYFKLSHLQMHSRKHTG (SEQ ID NO:2; WT1-331 long): HLA class II peptides inducing CD4+ responses that could provide help for long lasting CD8+ T cell responses.

Drug Product: The four peptides are provided in a sterile solution with phosphate buffered saline to produce the vaccine product ("WT1 Vax"). Each vial contains 280 mcg of each peptide in a total volume of 0.7 ml (0.4 mg/ml of each peptide, overfill of 40%). Vialing under GMP conditions and sterility testing was performed. The vaccine emulsion will be individually prepared prior to use. This will require mixture of the peptide solution with the immunologic adjuvant Montanide ISA 51 VG.

Intended Dose: The 200 mcg dose for each peptide is chosen because it is within the range of safe and active doses used by others. Peptide vaccines have generated immune and clinical responses within a wide range of doses (100-2000 mcg injected) without clear evidence of dose-response relationships. Higher doses have the theoretical possibility of stimulating lower affinity TCRs on T cells and making a reduced response [30, 33, 34]. Vial Size: Each single-dose vial contains 0.7 ml Route of Administration: Subcutaneous
Nivolumab: Intended Dose: 3 mg/kg; Vial Size: 10 mL; Route of Administration: Intravenous. Nivolumab will be dosed at 3 mg/kg and administered intravenously as a 60-minute IV infusion once every 2 weeks. At the end of the infusion, flush the line with a sufficient quantity of normal saline. If the subject's weight differs >10% from the previous weight used to calculate the required dose, a required dose, a corrected dose should be calculated. There will be no dose escalations or reductions of nivolumab allowed. There are no premedications recommended for the first nivolumab treatment.

Subjects may be dosed no less than 12 days between nivolumab doses and no more than 3 days after the scheduled dosing date. Dose given after the 3 days window is considered a dose delay. Treatment may be delayed for up to a maximum of 6 weeks from the previous dose.

Tumor assessments by CT or MRI should continue as per protocol even if dosing is delayed.

Treatment/Intervention Plan

Patients will be treated as outpatients.

WT1 vaccines will be administered on weeks 0, 2, 4, 6, 8 and 10.

All injections will be administered subcutaneously with sites rotating between extremities.

All patients will receive Sargramostim (GM-CSF) 70 mcg injected subcutaneously on days 0 and −2. Patients may self administer the GM-CSF if they have been appropriately instructed on SQ injection administration. Patients will be informed of the expected reactions such as irritation at the injection site. Patients will keep a logbook noting the time and placement of the injection.

Patients will also receive 1.0 ml of emulsion of WT1 peptides with Montanide. It will be administered by a nurse (it may not be self-administered) subcutaneously at the same anatomical site as the GM-CSF.

Patients will be observed for approximately 30 minutes after vaccination.

Nivolumab will be administered intravenously as a 60-minute infusion on weeks 0, 2, 4, 6, 8, 10 and 12. Subjects may be dosed no less than 12 days between nivolumab doses and no more than 3 days after the scheduled dosing date. Dose given after the 3-day window is considered a dose delay. Treatment may be delayed for up to a maximum of 6 weeks from the previous dose.

Combination treatment of the WT1 vaccine and nivolumab is expected to increase the WT1 specific CTL population in the patient and afford increased activity against the WT1 expressing tumor, as compared to WT1 vaccination alone or nivolumab treatment alone.

REFERENCES

1. Siegel, R., D. Naishadham, and A. Jemal, Cancer statistics, 2012. CA Cancer J Clin, 2012. 62(1): p. 10-29.
2. Hoskins, W. J., C. A. Perez, and R. C. Young, Principles and practice of gynecologic oncology. 3rd ed. 2000, Philadelphia: Lippincott Williams & Wilkins. xxi, 1268 p.
3. Barnhill, D. R., et al., The second-look surgical reassessment for epithelial ovarian carcinoma. Gynecol Oncol, 1984. 19(2): p. 148-54.
4. Rubin, S. C., et al., Recurrence after negative second-look laparotomy for ovarian cancer:
    analysis of risk factors. Am J Obstet Gynecol, 1988. 159(5): p. 1094-8.
5. Markman, M., et al., Second-line platinum therapy in patients with ovarian cancer previously treated with cisplatin. J Clin Oncol, 1991. 9(3): p. 389-93.
6. Zhang, H., et al., Antibodies against GD2 ganglioside can eradicate syngeneic cancer micrometastases. Cancer Res, 1998. 58(13): p. 2844-9.
7. Zhang, L., et al., Intratumoral T cells, recurrence, and survival in epithelial ovarian cancer. N Engl J Med, 2003. 348(3): p. 203-13.
8. Curiel, T. J., et al., Specific recruitment of regulatory T cells in ovarian carcinoma fosters immune privilege and predicts reduced survival. Nat Med, 2004. 10(9): p. 942-9.
9. Iasonos, A., et al., Identifying clinical improvement in consolidation single-arm phase 2 trials in patients with ovarian cancer in second or greater clinical remission. Int J Gynecol Cancer, 2012. 22(1): p. 63-9.
10. Berek, J. S., et al., Randomized, placebo-controlled study of oregovomab for consolidation of clinical remission in patients with advanced ovarian cancer. J Clin Oncol, 2004. 22(17): p. 3507-16.
11. Reinartz, S., et al., Vaccination of patients with advanced ovarian carcinoma with the anti-idiotype ACA125: immunological response and survival (phase Ib/II). Clin Cancer Res, 2004. 10(5): p. 1580-7.
12. Bookman, M. A., et al., Evaluation of monoclonal humanized anti-HER2 antibody, trastuzumab, in patients with recurrent or refractory ovarian or primary peritoneal carcinoma with overexpression of HER2: a phase II trial of the Gynecologic Oncology Group. J Clin Oncol, 2003. 21(2): p. 283-90.
13. Allavena, P., et al., Intraperitoneal recombinant gamma-interferon in patients with recurrent ascitic ovarian carcinoma: modulation of cytotoxicity and cytokine production in tumor-associated effectors and of major histocompatibility antigen expression on tumor cells. Cancer Res, 1990. 50(22): p. 7318-23.
14. Pujade-Lauraine, E., et al., Intraperitoneal recombinant interferon gamma in ovarian cancer patients with residual disease at second-look laparotomy. J Clin Oncol, 1996. 14(2): p. 343-50.
15. Recchia, F., et al., Interleukin-2 and 13-cis retinoic acid as maintenance therapy in advanced ovarian cancer. Int J Oncol, 2005. 27(4): p. 1039-46.
16. Sabbatini, P. J., et al., Immunization of ovarian cancer patients with a synthetic Lewis(y)-protein conjugate vaccine: a phase 1 trial. Int J Cancer, 2000. 87(1): p. 79-85.
17. Nicholson, S., et al., A phase I trial of idiotypic vaccination with HMFG1 in ovarian cancer. Cancer Immunol Immunother, 2004. 53(9): p. 809-16.
18. Diefenbach, C. S., et al., Safety and immunogenicity study of NY-ESO-1b peptide and montanide ISA-51 vaccination of patients with epithelial ovarian cancer in high-risk first remission. Clin Cancer Res, 2008. 14(9): p. 2740-8.
19. Keilholz, U., et al., Wilms' tumour gene 1 (WT1) in human neoplasia. Leukemia, 2005. 19(8): p. 1318-23.
20. Oji, Y., et al., Expression of the Wilms' tumor gene WT1 in solid tumors and its involvement in tumor cell growth. Jpn J Cancer Res, 1999. 90(2): p. 194-204.
21. Scharnhorst, V., et al., Internal translation initiation generates novel WT1 protein isoforms with distinct biological properties. J Biol Chem, 1999. 274(33): p. 23456-62.
22. Haber, D. A., et al., Alternative splicing and genomic structure of the Wilms tumor gene WT1. Proc Natl Acad Sci USA, 1991. 88(21): p. 9618-22.
23. Mundlos, S., et al., Nuclear localization of the protein encoded by the Wilms' tumor gene WT1 in embryonic and adult tissues. Development, 1993. 119(4): p. 1329-41.

24. Buckler, A. J., et al., Isolation, characterization, and expression of the murine Wilms' tumor gene (WT1) during kidney development. Mol Cell Biol, 1991. 11(3): p. 1707-12.
25. Fraizer, G. C., et al., Expression of the tumor suppressor gene WT1 in both human and mouse bone marrow. Blood, 1995. 86(12): p. 4704-6.
26. Al-Hussaini, M., et al., WT1 assists in distinguishing ovarian from uterine serous carcinoma and in distinguishing between serous and endometrioid ovarian carcinoma. Histopathology, 2004. 44(2): p. 109-15.
27. Pinilla-Ibarz, J., et al., Improved human T-cell responses against synthetic HLA-0201 analog peptides derived from the WT1 oncoprotein. Leukemia, 2006. 20(11): p. 2025-33.
28. May, R. J., et al., Peptide epitopes from the Wilms' tumor 1 oncoprotein stimulate CD4+ and CD8+ T cells that recognize and kill human malignant mesothelioma tumor cells. Clin Cancer Res, 2007. 13(15 Pt 1): p. 4547-55.
29. Krug, L. M., et al., WT1 peptide vaccinations induce CD4 and CD8 T cell immune responses in patients with mesothelioma and non-small cell lung cancer. Cancer Immunol Immunother, 2010. 59(10): p. 1467-79.
30. Oka, Y., et al., Induction of WT1 (Wilms' tumor gene)-specific cytotoxic T lymphocytes by WT1 peptide vaccine and the resultant cancer regression. Proc Natl Acad Sci USA, 2004. 101(38): p. 13885-90.
31. Letsch, A., et al., Effect of vaccination of leukemia patients with a MHC class I peptide of Wilms tumor gene 1 (WT1) peptide with unspecific T helper stimulation on WT1-specific IgM responses and on IgG responses. J Clin Oncol, 2008. 26: p. Abstr 3054.
32. Ohno, S., et al., Wilms' tumor 1 (WT1) peptide immunotherapy for gynecological malignancy. Anticancer Res, 2009. 29(11): p. 4779-84.
33. Schaed, S. G., et al., T-cell responses against tyrosinase 368-376(370D) peptide in HLA*A0201+ melanoma patients: randomized trial comparing incomplete Freund's adjuvant, granulocyte macrophage colony-stimulating factor, and QS-21 as immunological adjuvants. Clin Cancer Res, 2002. 8(5): p. 967-72.
34. Slingluff, C. L., Jr., et al., Clinical and immunologic results of a randomized phase II trial of vaccination using four melanoma peptides either administered in granulocyte-macrophage colony-stimulating factor in adjuvant or pulsed on dendritic cells. J Clin Oncol, 2003. 21(21): p. 4016-26.
35. Faries, M. B., et al., Effect of granulocyte/macrophage colony-stimulating factor on vaccination with an allogeneic whole-cell melanoma vaccine. Clin Cancer Res, 2009. 15(22): p. 7029-35.
36. Keilholz, U., et al., A clinical and immunologic phase 2 trial of Wilms tumor gene product 1 (WT1) peptide vaccination in patients with AML and MDS. Blood, 2009. 113(26): p. 6541-8.
37. Weber, J., et al., Granulocyte-macrophage-colony-stimulating factor added to a multipeptide vaccine for resected Stage II melanoma. Cancer, 2003. 97(1): p. 186-200.
38. Keir, M. E., et al., PD-1 and its ligands in tolerance and immunity. Annu Rev Immunol, 2008. 26: p. 677-704.
39. Freeman, G. J., et al., Engagement of the PD-1 immunoinhibitory receptor by a novel B7 family member leads to negative regulation of lymphocyte activation. J Exp Med, 2000. 192(7): p. 1027-34.
40. Latchman, Y., et al., PD-L2 is a second ligand for PD-1 and inhibits T cell activation. Nat Immunol, 2001. 2(3): p. 261-8.
41. Hamanishi, J., et al., Programmed cell death 1 ligand 1 and tumor-infiltrating CD8+ T lymphocytes are prognostic factors of human ovarian cancer. Proc Natl Acad Sci USA, 2007. 104(9): p. 3360-5.
42. Mu, C. Y., et al., High expression of PD-L1 in lung cancer may contribute to poor prognosis and tumor cells immune escape through suppressing tumor infiltrating dendritic cells maturation. Med Oncol, 2011. 28(3): p. 682-8.
43. Pardoll, D. M., The blockade of immune checkpoints in cancer immunotherapy. Nat Rev Cancer, 2012. 12(4): p. 252-64.
44. Nivolumab (BMS-936558) Investigator Brochure, Version 12. 2013.
45. Hwang, W. T., et al., Prognostic significance of tumor-infiltrating T cells in ovarian cancer: a meta-analysis. Gynecol Oncol, 2012. 124(2): p. 192-8.
46. Matsuzaki, J., et al., Tumor-infiltrating NY-ESO-1-specific CD8+ T cells are negatively regulated by LAG-3 and PD-1 in human ovarian cancer. Proc Natl Acad Sci USA, 2010. 107(17): p. 7875-80.
47. Brahmer, J. R., et al., Safety and activity of anti-PD-L1 antibody in patients with advanced cancer. N Engl J Med, 2012. 366(26): p. 2455-65.
48. Page, D. B., et al., Immune modulation in cancer with antibodies. Annu Rev Med, 2014. 65: p. 185-202.
49. Harrison, M. L., et al., Duration of second or greater complete clinical remission in ovarian cancer: exploring potential endpoints for clinical trials. Gynecol Oncol, 2007. 106(3): p. 469-75.
50. Juretzka, M., et al., A phase 2 trial of oral imatinib in patients with epithelial ovarian, fallopian tube, or peritoneal carcinoma in second or greater remission. Eur J Gynaecol Oncol, 2008. 29(6): p. 568-72.
51. Levine, D., et al., A phase II evaluation of goserelin and bicalutamide in patients with ovarian cancer in second or higher complete clinical disease remission. Cancer, 2007. 110(11): p. 2448-56.
52. Walter, S., et al., Multipeptide immune response to cancer vaccine IMA901 after single-dose cyclophosphamide associates with longer patient survival. Nat Med, 2012.
53. Wolchok, J. D., et al., Development of ipilimumab: a novel immunotherapeutic approach for the treatment of advanced melanoma. Ann N Y Acad Sci, 2013. 1291(1): p. 1-13.
54. Hodi, F. S., et al., Immunologic and clinical effects of antibody blockade of cytotoxic T lymphocyte-associated antigen 4 in previously vaccinated cancer patients. Proc Natl Acad Sci USA, 2008. 105(8): p. 3005-10.
55. Quezada, S. A., et al., CTLA4 blockade and GM-CSF combination immunotherapy alters the intratumor balance of effector and regulatory T cells. J Clin Invest, 2006. 116(7): p. 1935-45.
56. Duraiswamy, J., et al., Dual blockade of PD-1 and CTLA-4 combined with tumor vaccine effectively restores T-cell rejection function in tumors. Cancer Res, 2013. 73(12): p. 3591-603.
57. Wolchok, J. D., et al., Guidelines for the evaluation of immune therapy activity in solid tumors: immune-related response criteria. Clin Cancer Res, 2009. 15(23): p. 7412-20.
58. Dupont, J., et al., Wilms Tumor Gene (WT1) and p53 expression in endometrial carcinomas: a study of 130 cases using a tissue microarray. Gynecol Oncol, 2004. 94(2): p. 449-55.
59. Eisenhauer, E. A., et al., New response evaluation criteria in solid tumours: revised RECIST guideline (version 1.1). Eur J Cancer, 2009. 45(2): p. 228-47.

What is claimed is:

1. A method for treating, reducing the incidence of, or inducing an immune response against a WT1-expressing cancer, comprising administering to a human subject in need thereof (a) at least one WT1 peptide against a WT1-expressing cancer, and (b) at least one antibody checkpoint inhibitor that blocks or inhibits PD-1, wherein the at least one WT1 peptide is a combination of YMFPNAPYL (SEQ ID NO:124), RSDELVRHHNMHQRNMTKL (SEQ ID NO:1), PGCNKRYFKLSHLQMHSRKHTG (SEQ ID NO: 2) and SGQAYMFPNAPYLPSCLES (SEQ ID NO:125).

2. The method of claim 1 wherein (a) is administered with an adjuvant.

3. The method of claim 1 wherein the antibody checkpoint inhibitor is nivolumab, pembrolizumab, pidilizumab, MEDI0680 (AMP-514), or a combination of any of the foregoing.

4. The method of claim 1 wherein the cancer is ovarian cancer, mesothelioma, leukemia, Wilms' tumor, acute myelogenous leukemia (AML), chronic myeloid leukemia (CML), myelodysplastic syndrome (MDS), melanoma, stomach cancer, prostate cancer, biliary cancer, urinary system cancer, glioblastoma, soft tissue sarcoma, osteosarcoma, or non-small cell lung cancer (NSCLC).

5. The method of claim 2 wherein the adjuvant is QS21, Montanide, Freund's complete or incomplete adjuvant, aluminum phosphate, aluminum hydroxide, BCG, a cytokine, or alum.

6. The method of claim 1 wherein 200 mcg of each peptide is emulsified with Montanide ISA 51 VG and administered subcutaneously on weeks 0, 2, 4, 6, 8 and 10.

7. The method of claim 3 wherein the antibody checkpoint inhibitor is nivolumab.

8. The method of claim 6 wherein 3 mg/kg of nivolumab is administered intravenously on weeks 0, 2, 4, 6, 8, 10 and 12.

9. The method of claim 1 wherein the treating, reducing the incidence of, or inducing an immune response against a WT1-expressing cancer is greater than achieved by administering the at least one WT1 peptide alone or the antibody checkpoint inhibitor that blocks or inhibits PD-1 alone.

10. The method of claim 1, wherein the cancer is ovarian cancer and (a) and (b) are administered after completion of chemotherapy.

11. The method of claim 1, wherein the subject is in remission.

12. The method of claim 1, wherein the cancer is ovarian cancer and the antibody checkpoint inhibitor is nivolumab.

* * * * *